US011330806B2

(12) United States Patent
Li et al.

(10) Patent No.: US 11,330,806 B2
(45) Date of Patent: May 17, 2022

(54) ANDROGENETIC HAPLOID EMBRYONIC STEM CELL (AG-HAESC), AND PREPARATION METHOD AND USE THEREOF

(71) Applicant: CENTER FOR EXCELLENCE IN MOLECULAR CELL SCIENCE, CHINESE ACADEMY OF SCIENCES, Shanghai (CN)

(72) Inventors: Jinsong Li, Shanghai (CN); Yuxuan Wu, Shanghai (CN); Cuiqing Zhong, Shanghai (CN); Qi Yin, Shanghai (CN); Zhenfei Xie, Shanghai (CN); Meizhu Bai, Shanghai (CN)

(73) Assignee: CENTER FOR EXCELLENCE IN MOLECULAR CELL SCIENCE, CHINESE ACADEMY OF SCIENCES, Shanghai (CN)

(*) Notice: Subject to any disclaimer, the term of this patent is extended or adjusted under 35 U.S.C. 154(b) by 630 days.

(21) Appl. No.: 15/740,974

(22) PCT Filed: Jul. 2, 2015

(86) PCT No.: PCT/CN2015/083165
§ 371 (c)(1),
(2) Date: May 15, 2018

(87) PCT Pub. No.: WO2017/000302
PCT Pub. Date: Jan. 5, 2017

(65) Prior Publication Data
US 2018/0251728 A1    Sep. 6, 2018

(51) Int. Cl.
| | | |
|---|---|---|
| A01K 67/00 | (2006.01) | |
| A01K 67/027 | (2006.01) | |
| C12N 15/85 | (2006.01) | |
| C12N 15/113 | (2010.01) | |
| C12N 15/877 | (2010.01) | |
| C12N 5/0735 | (2010.01) | |
| C12N 15/873 | (2010.01) | |

(52) U.S. Cl.
CPC ........ *A01K 67/0276* (2013.01); *C12N 5/0606* (2013.01); *C12N 15/113* (2013.01); *C12N 15/85* (2013.01); *C12N 15/873* (2013.01); *C12N 15/8775* (2013.01); *A01K 2217/075* (2013.01); *A01K 2217/15* (2013.01); *A01K 2227/105* (2013.01); *C12N 2500/10* (2013.01); *C12N 2500/50* (2013.01); *C12N 2501/065* (2013.01); *C12N 2501/235* (2013.01); *C12N 2501/727* (2013.01); *C12N 2502/99* (2013.01); *C12N 2740/16043* (2013.01)

(58) Field of Classification Search
CPC .......... A01K 67/0276; A01K 2217/075; A01K 2217/15; A01K 2227/105
See application file for complete search history.

(56) References Cited

FOREIGN PATENT DOCUMENTS

| CN | 103361304 A | 10/2013 |
|---|---|---|
| WO | WO 2013/150313 A1 | 10/2013 |

OTHER PUBLICATIONS

Wutz Development 141; 1432-1426, 2014 (Year: 2014).*
Bai et al. Journal of Internal Medicine, doi: 10.1111/joim.12503, pp. 236-245, 2016 (Year: 2016).*
Lee & Kim. Nature Biotechnology 36, 703-704 (Year: 2018).*
Yang, H. et al., "Generation of Genetically Modified Mice by Oocyte Injection of Androgenetic Haploid Embryonic Stem Cells", Cell, vol. 149, Apr. 27, 2012 (Apr. 27, 2012), pp. 605-617, and SI-S6.
Kawahara, M. et al., "High-frequency generation of viable mice from engineered bi-maternal embryos", Nature Biotechnology, vol. 25, No. 9, Aug. 19, 2007 (Aug. 19, 2007), pp. 1045-1050.
Li, W. et al., "Genetic Modification and Screening in Rat Using Haploid Embryonic Stem Cells", Cell Stem Cell, vol. 14,Mar. 6, 2014 (Mar. 6, 2014), pp. 404-414.
Chen, S.D. et al., "Genome-wide CRISPR Screen in a Mouse Model of Tumor Growth and Metastasis", Cell, vol. 160, Mar. 12, 2015 (Mar. 12, 2015), pp. 1246-1260.
Liang, Dan et al., "Progress of CRISPR-Cas9 in stem cell research", Chinese Bulletin of Life Sciences, vol. 27, No. 1, Jan. 31, 2015 (Jan. 31, 2015), pp. 93-98, abstract only.
Lin, S. P. et al., "Asymmetric regulation of imprinting on the maternal and paternal chromosomes at the Dlk1-Gtl2 imprinted cluster on mouse chromosome 12", Nature Genetics, vol. 35, No. 1, Aug. 24, 2003 (Aug. 24, 2003), pp. 97-102.
Thorvaldsen, J.L. et al., "Analysis of Sequence Upstream of the Endogenous H19 Sene Reveals Elements Both Essential and Dispensable for Imprinting", Molecular and Cellular Biology, vol. 22, No. 8, Apr. 30, 2002 (Apr. 30, 2002), pp. 2450-2462.

\* cited by examiner

*Primary Examiner* — Marcia S Noble
(74) *Attorney, Agent, or Firm* — Tianhua Gu; Global IP Services

(57) ABSTRACT

The present invention relates to an AG-haESCs in which H19 DMR and IG-DMR are knocked out, a method for preparing the AG-haESCs, and use of the AG-haESCs in constructing a genetically modified semi-cloned animal and a library of a genetically modified semi-cloned animal. The AG-haESCs is capable of obtaining characteristics resembling a round spermatid, and upon injection into an oocyte, a viable SC mouse is stably obtained. The present invention is capable of being effectively used in multi-gene genetic manipulation, advancing the acquisition of animals with multiple genetic modifications.

6 Claims, 21 Drawing Sheets
Specification includes a Sequence Listing.

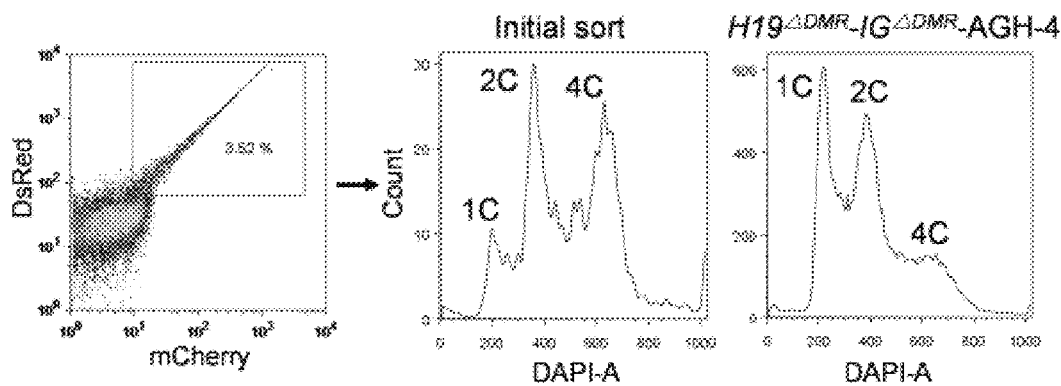
FIG.1G
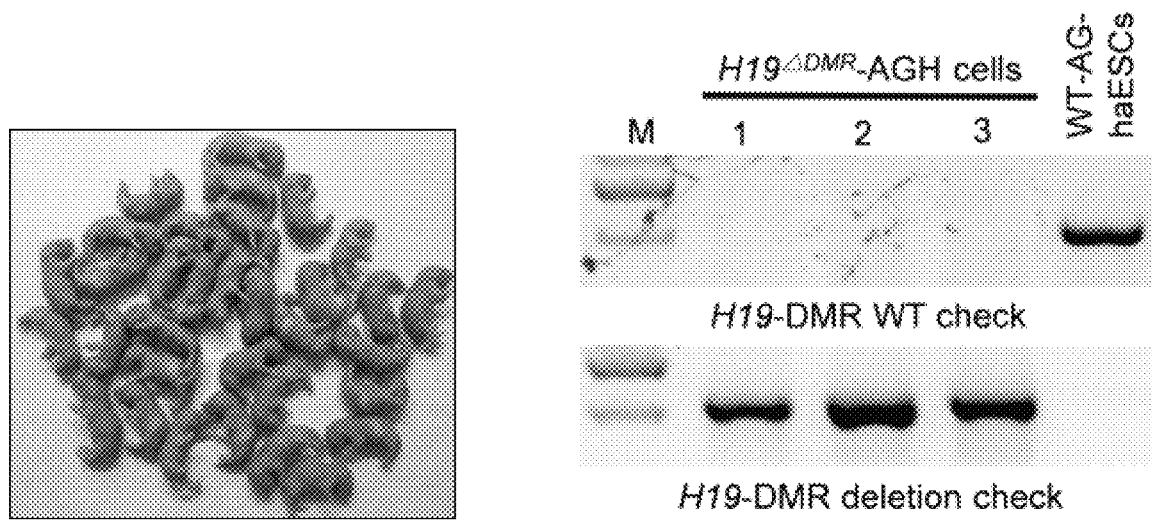
FIG.1H
FIG.1I
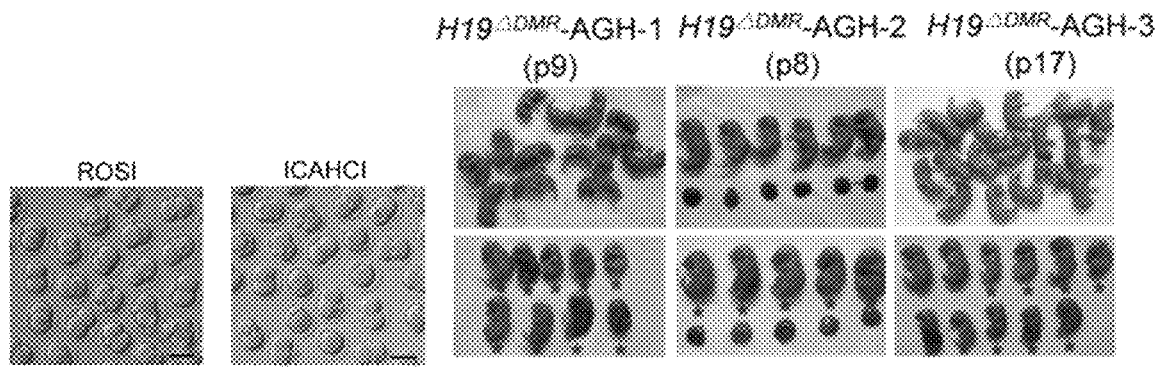
FIG.1J
FIG.1K

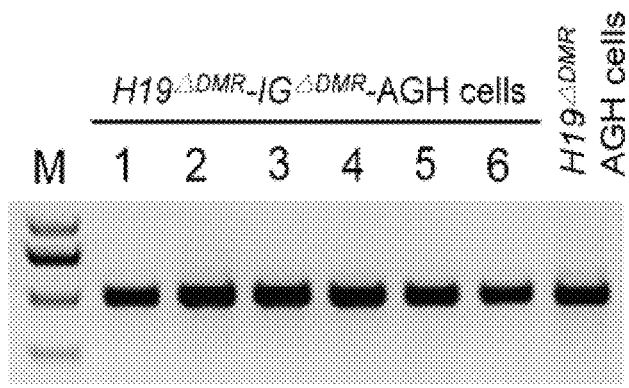
FIG.2I
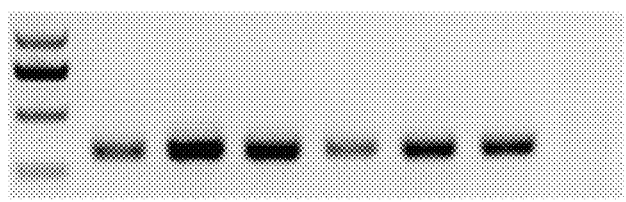
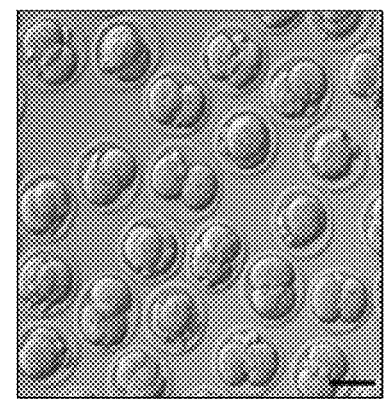
FIG.2K
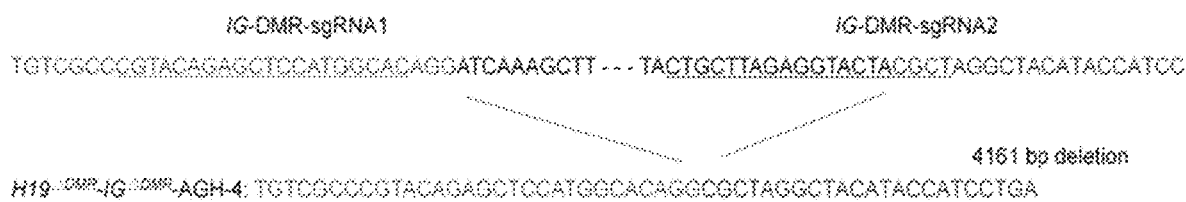
FIG.2J
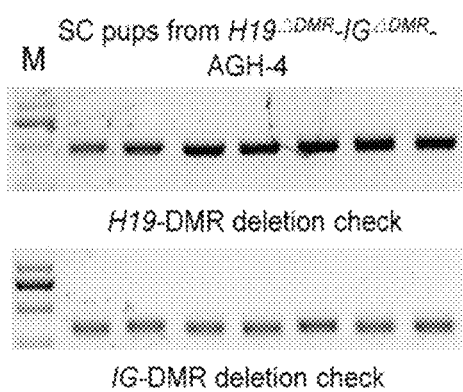
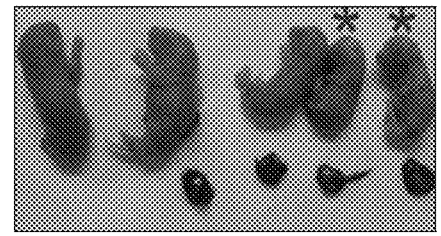
FIG.2L
FIG.2M

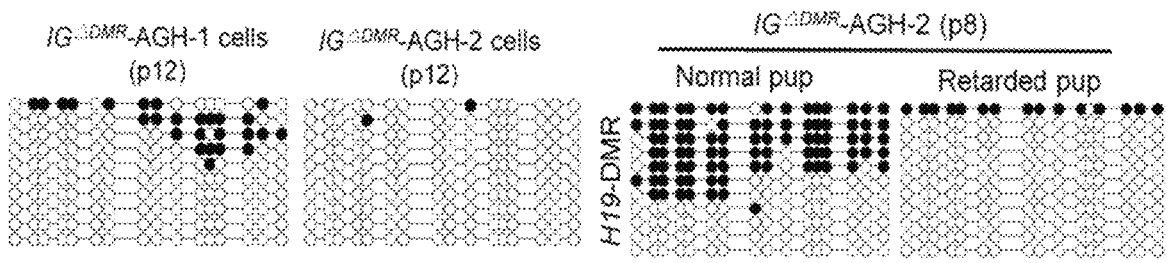
FIG.2N  FIG.2O
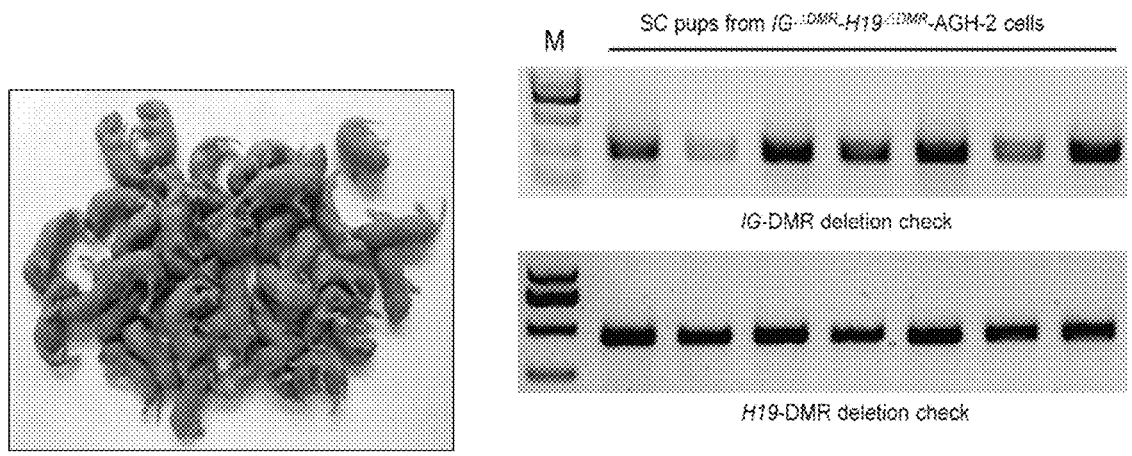
FIG.2P
FIG.2Q  FIG.2R
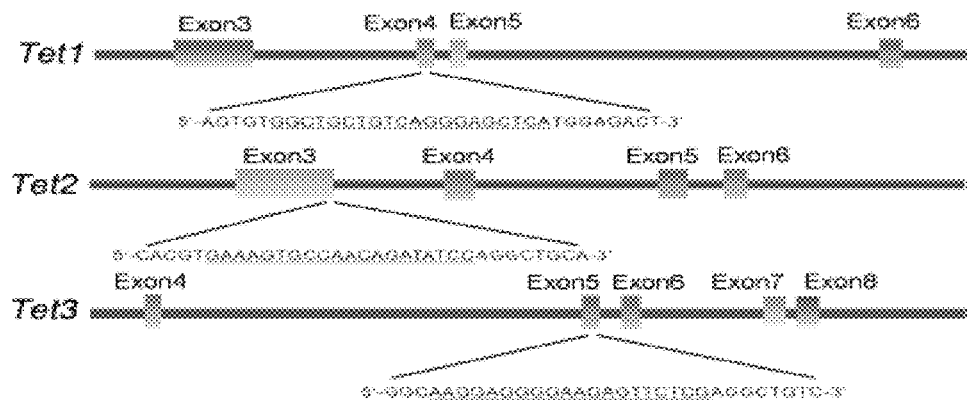
FIG.3A

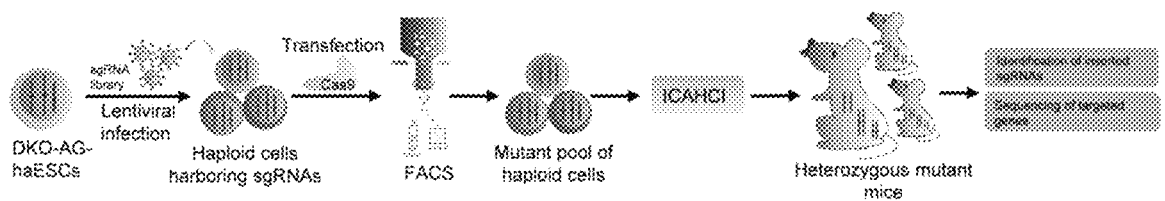
FIG.4A
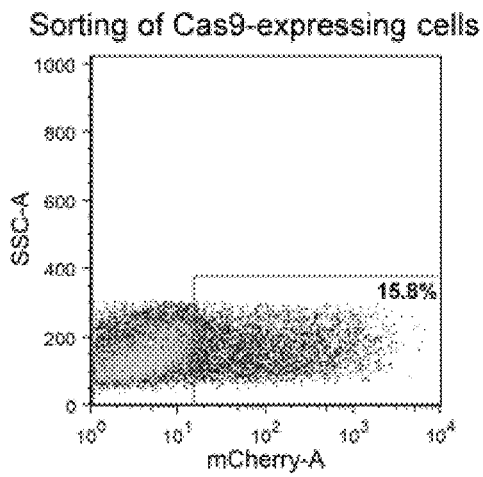
FIG.4B
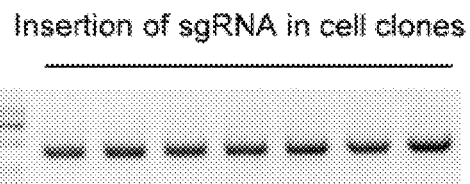
FIG.4C
FIG.4D
FIG.4E
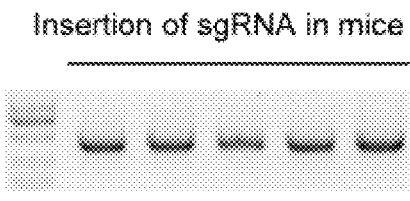
FIG.4F Mutant genes in mice

```
Fibp    TGCGAGTACGCTCCGGAATCTTGGAGCAGACGGGAGCC   WT
        TGCGAGTACGCTCCGGA--CTTGGAGCAGACGGGAGCC   -2
Csf2    GAGTTCTCCTTCAAGGTAAGCTGCTTCTCTTTGCTCT    WT
        GAGTTCTCCTTCAAG--------CTTCTCTTTGCTCT    -8
Vav3    TTGAAGAACATCGGACATTCCTGGCCGCCTGCTGCGA    WT
        TTGAAGAACATCGGACAT-CCTGGCCGCCTGCTGCGA    -1
Lrrc61  GTCCACTCAGGAGAATTTGCCCTGGATTCCATCCTGT    WT
        GTCCACTCAGGAGAATT--------------------    -38
```

FIG.4G

Tet-TKO-DAH-3

```
Tet1    CTGCTGTCAGGGAGCCTCATGGAGACTAGGT   +1
        CTGCTGTCAGGGAGC TCATGGAGACTAGGT   WT

Tet2    AAGTGCCAACAGATA--CAGGCTGCAGAATCG  -2
        AAGTGCCAACAGATATCCAGGCTGCAGAATCG  WT

Tet3    GGAAGAGTTCTTCGAGGCTGTCCCATCGCCAAG +1
        GGAAGAGTTCT CGAGGCTGTCCCATCGCCAAG WT
```

FIG.4H

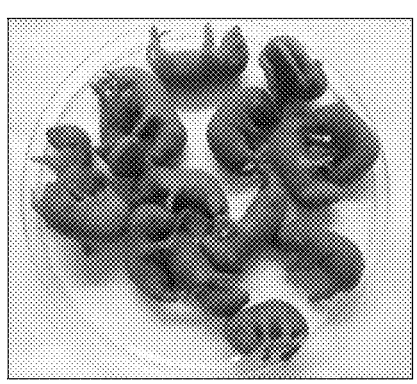

FIG.4I

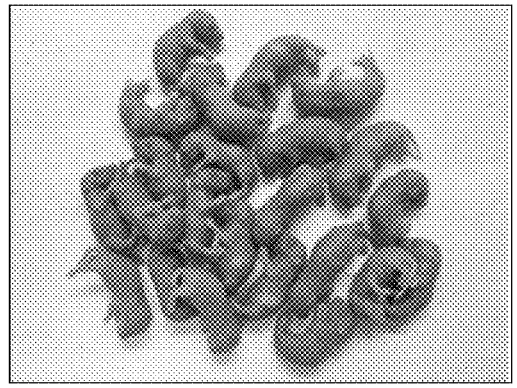

FIG.4K p53-TKO-DAH-1
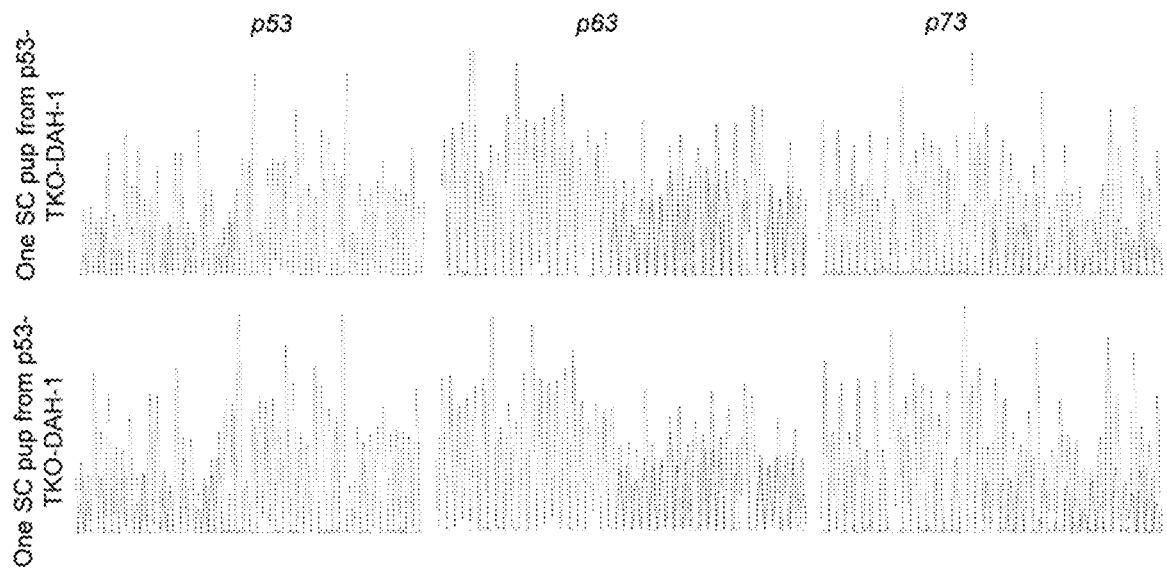
FIG.4J
FIG.4L
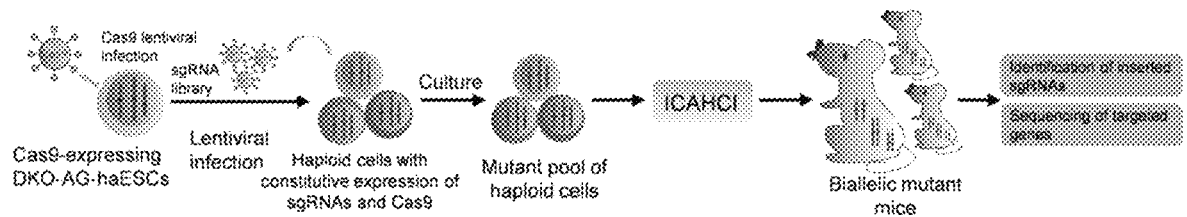
FIG.5A

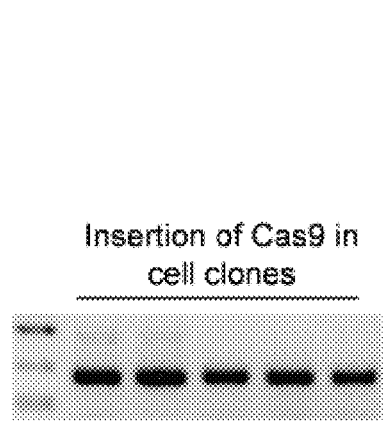
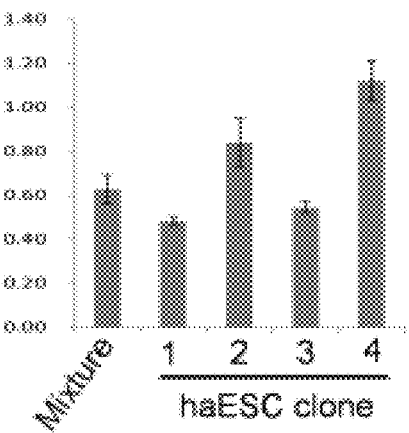
FIG.5B
FIG.5C
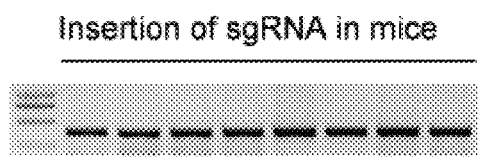
FIG.5D
FIG.5F
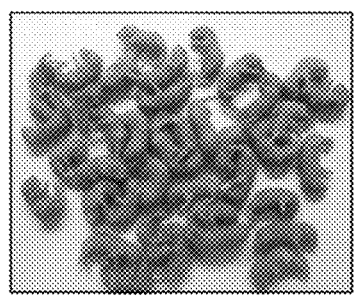
FIG.5E
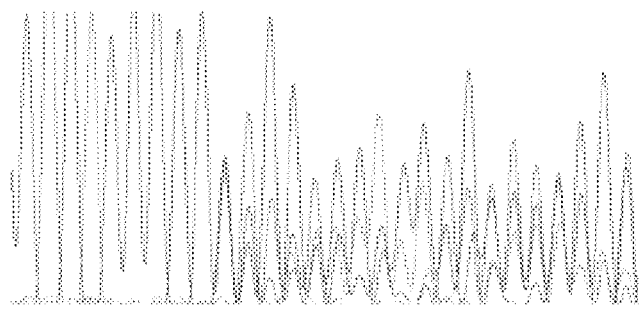
FIG.5G

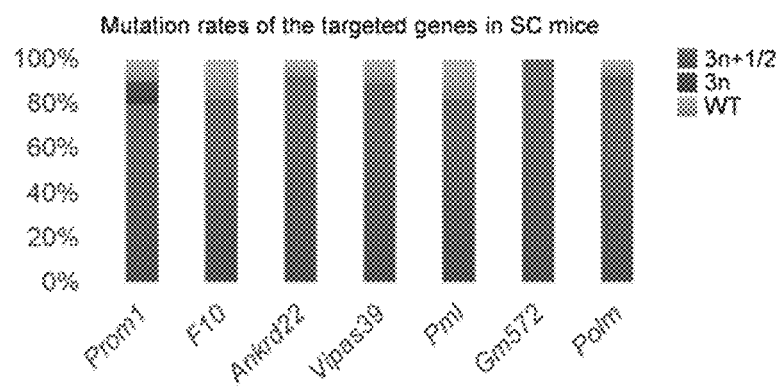
FIG.5H
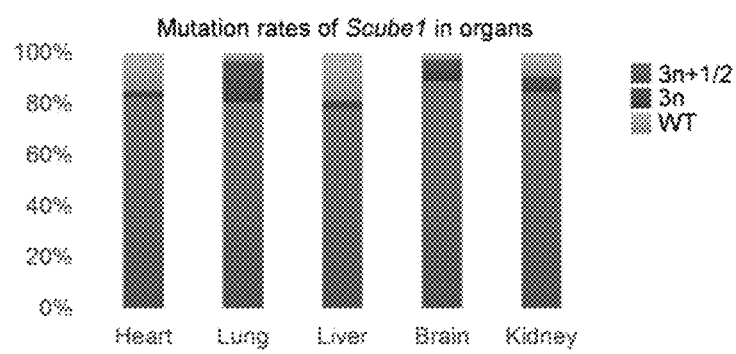
FIG.5I
FIG.5J
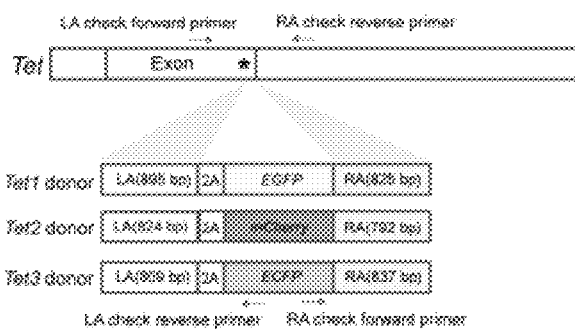
FIG.5K
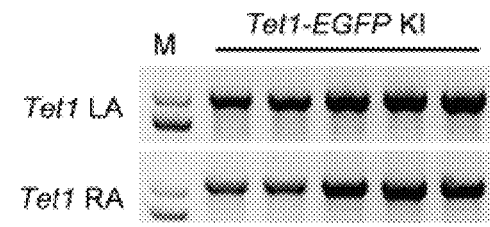
FIG.5L

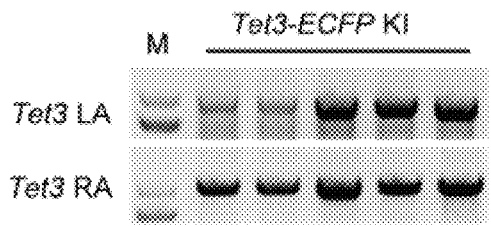

FIG.5M

FIG.5N

Sequencing of Tet1-EGFP

TGTGTCTATGAACTACCAGTGAGATAGTTTTTTGTTTTTTGTTTTTTGTTTTGTTTTTC
AAGGTTCACACAACACTAAGAGCTTTTCATCAGCCTCATCTACTTCTCACCTAGTGAA
 . . . . . . . . . . . . . . . . . . . . . . . . . . .
GCATCAACCTTAACCCGAGACAATGTTGTTACCGTGTCCCATACTCTCTCACTCATG
TTGCGGGACCCTACAATCGTTGGGTCGCGTCGACGATT............ 
............GTGAGCAAGGGCGAGGAGCTGTTCACCGGGG
TGGTGCCCATCCTGGTCGAGCTGGACGGCGACGTAAACGGCCACAAGTTCAGCGT
 . . . . . . . . . . . . . . . . . . . . . . . . . . .
CCGACAACCACTACCTGAGCACCCAGTCCGCCCTGAGCAAAGACCCCAACGAGAAG
CGCGATCACATGGTCCTGCTGGAGTTCGTGACCGCCGCCGGGATCACTCTCGGCAT
GGACGAGCTGTACAAGAATCTCTAGAGCTAAAGGCTTCTGTCATGTAATGGCTTTGCT
AATGTGGTGTAGTGGGTATTTTTGTTTGTTTGTTGGTTTCTTTTGTTTTTTGTTTTT
CCGGGTGCTGTTAAAAAGAAAGTCATTCTGTTGTTACTGTAGCTTTGTTTCCGCCATT
 . . . . . . . . . . . . . . . . . . . . . . . . . . .
GTTCTTGCTCTGTAGAGTCCCATCCCGTTAACCTCAGCCTGTACTCAAATAACACACG
GCTTCTGTTGTTTACTTATAGAATACAGGGTCTCTAAAAAAAAAATTTAAATACAAGAT
GCTACCAATATCAATTTTCGCTCTTTAACTAGAAAAAAATATTGTCTTGTGAAGTCACCTG

Sequencing of Tet3-ECFP

GCTTCGAGGCAAGCCATGGAGCCCCTGCAAGTTTGGGAACGGCACCTCTGCCTTGA
CTGGTGCCGAGCCTAACTGACAAGCCATGGGGGATGGGAACGGCGGGATTTCAACCCCC
 . . . . . . . . . . . . . . . . . . . . . . . . . . .
GGAGGCGGTGGGCATGCCGCACAGACTCCGCCGGTCAGCGGTGTCCTCTTACGCCTACA
CAAAGGTCACTGGCCCCTACAGCCGCTGGATCGCGTCGACGATT..........
............GTGAGCAAGGGCGAGGAGCTGTTCA
CCGGGGTGGTGCCCATCCTGGTCGAGCTGGACGGCGACGTAAACGGCCACAAGTT
 . . . . . . . . . . . . . . . . . . . . . . . . . . .
GAGAAGCGCGATCACATGGTCCTGCTGGAGTTCGTGACCGCCGCCGGGATCACTCT
CGGCATGGACGAGCTGTACAAGAATCTCTAGAGCTAGGTGCCAGGAGCCAGCCGTAC
CTCGGGCCCGGCCCGAGCTCCTCTGTGGTGCTTTTGCCCTCATGCCCGGGGGCGG
 . . . . . . . . . . . . . . . . . . . . . . . . . . .
TGGTTCGCTAGGGCAGACCTCAAGCTGGAGCAGGAGTCGAGAGGCTCCGAGCAGC
TCTTCTCCTCCCGTTGATAAAGCCGGTGAGTACTGGGCCGAAAGGAAGCTTAGTGG
CAGTTTTCTTAAAAATCGCCCCAAAGTTTGTCGATACTGAAAAAGGGCTACTGTATCTA

FIG.5O

FIG.5P

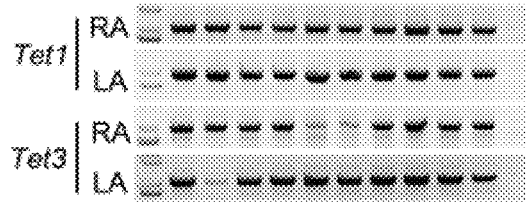

FIG.5Q

Sequencing of Tet2-mCherry

AGATGCCTTCACTACTAACTCCACCCTAAAACCAAATGTACACCACCTAGCAACGTTT
TCTCCTTACCCCACCCCCAAGATGGATAGTCATTTCATGGGAGCTGCCTCCAGATCA-
. . . . . . . . . . . . . . . . . . . . . . . . . . . . . . . . . . . . . . . . . . . . . . . . . . . . . .
ACAGGGTCTGTGACTACGGATTCTACCGTGACTACATCACCATATGCTTTCACTCAG
TCACAGGGCGTTACAACAGATTTGTAGCCGTCGACGATT . . . . . . . . . . . . . . . . . . . . .
. . . . . . . . . . . . . . . . . . . . . GTGAGCAAGGGCGAGGAGGATAACATGGCCAT
CATCAAGGAGTTCATGCGCTTCAAGGTGCACATGGAGGGCTCCGTGAACGGCCACG
. . . . . . . . . . . . . . . . . . . . . . . . . . . . . . . . . . . . . . . . . . . . . . . . . . . . . .
CGCCTACAACGTCAACATCAAGTTGGACATCACCTCCCACAACGAGGACTACACCAT
CGTGGAACAGTACGAACGCGCCGAGGGCCGCCACTCCACCGGCGGCATGGACGA
GCTGTACAAGAATCTCTAGAGCTGACCCTGCGCATTAGGCCAGACCACCAAGGACCG
ACCTGTGAGCAGTATGTCTTTCATGGCATGGGCCGTAGGGACAGGTCACAGCATCT
. . . . . . . . . . . . . . . . . . . . . . . . . . . . . . . . . . . . . . . . . . . . . . . . . . . . . .
ATCTTAATTATTCAGCTTAGTTTTTAAAATGTGGACATTTCAAAGGCGTGTGGATTGTAG
TTATCCACCGATGTCCTTGTAGGACTATAATGTATAGATATGCACACTTACACATGTGTA
CTGAAATATTTTAAGTTGTGTCTTAGAAAAGCACTTTGCCTACC

FIG.5R

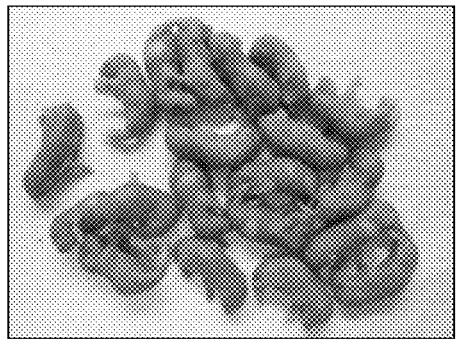

FIG.5S

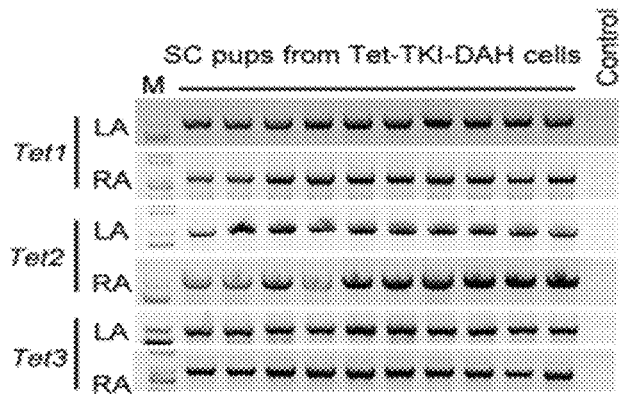

FIG.5T

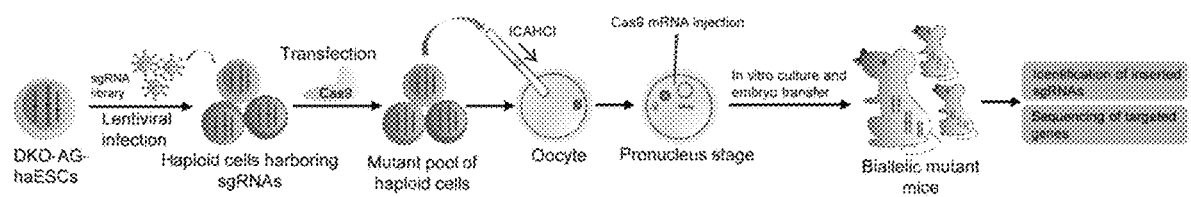
FIG.6A
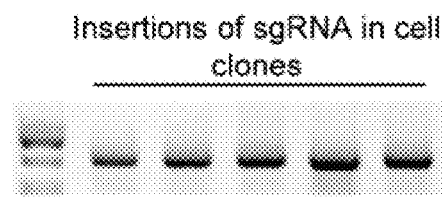
FIG.6B
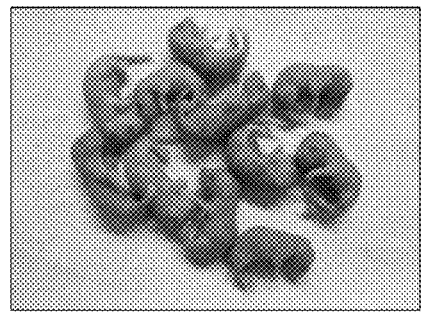
FIG.6C
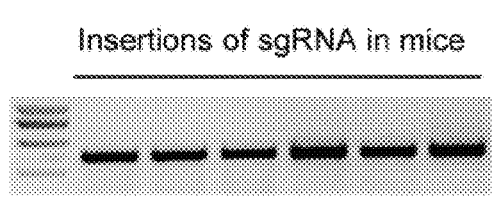
FIG.6D
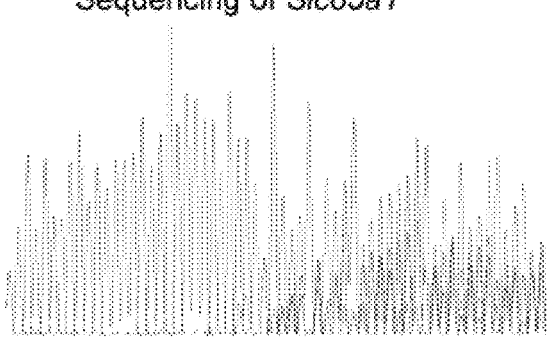
FIG.6E
FIG.6F

```
                        SEQUENCE LISTING

<160> NUMBER OF SEQ ID NOS: 136

<210> SEQ ID NO 1
<211> LENGTH: 20
<212> TYPE: DNA
<213> ORGANISM: Artificial Sequence
<220> FEATURE:
<223> OTHER INFORMATION: IG-DMR-sgRNA1 sequence

<400> SEQUENCE: 1
cgtacagagc tccatggcac                                                 20

<210> SEQ ID NO 2
<211> LENGTH: 20
<212> TYPE: DNA
<213> ORGANISM: Artificial Sequence
<220> FEATURE:
<223> OTHER INFORMATION: IG-DMR-sgRNA2 sequence

<400> SEQUENCE: 2
ctgcttagag gtactacgct                                                 20

<210> SEQ ID NO 3
<211> LENGTH: 20
<212> TYPE: DNA
<213> ORGANISM: Artificial Sequence
<220> FEATURE:
<223> OTHER INFORMATION: H19-3.8K sgRNA-1 sequence

<400> SEQUENCE: 3
catgaactca gaagagactg                                                 20

<210> SEQ ID NO 4
<211> LENGTH: 20
<212> TYPE: DNA
<213> ORGANISM: Artificial Sequence
<220> FEATURE:
```

<223> OTHER INFORMATION: H19-3.8K sgRNA-2 sequence

<400> SEQUENCE: 4
aggtgagaac cactgctgag                                                  20

<210> SEQ ID NO 5
<211> LENGTH: 20
<212> TYPE: DNA
<213> ORGANISM: Artificial Sequence
<220> FEATURE:
<223> OTHER INFORMATION: Tet1 sgRNA sequence

<400> SEQUENCE: 5
ggctgctgtc agggagctca                                                  20

<210> SEQ ID NO 6
<211> LENGTH: 20
<212> TYPE: DNA
<213> ORGANISM: Artificial Sequence
<220> FEATURE:
<223> OTHER INFORMATION: Tet2 sgRNA sequence

<400> SEQUENCE: 6
gaaagtgcca acagatatcc                                                  20

<210> SEQ ID NO 7
<211> LENGTH: 20
<212> TYPE: DNA
<213> ORGANISM: Artificial Sequence
<220> FEATURE:
<223> OTHER INFORMATION: Tet3 sgRNA sequence

<400> SEQUENCE: 7
aaggagggga agagttctcg                                                  20

<210> SEQ ID NO 8
<211> LENGTH: 20
<212> TYPE: DNA
<213> ORGANISM: Artificial Sequence
<220> FEATURE:
<223> OTHER INFORMATION: p53 sgRNA sequence

<400> SEQUENCE: 8
cacctgggct tcctgcagtc                                                  20

<210> SEQ ID NO 9
<211> LENGTH: 20
<212> TYPE: DNA
<213> ORGANISM: Artificial Sequence
<220> FEATURE:
<223> OTHER INFORMATION: p63 sgRNA sequence

<400> SEQUENCE: 9
tgggcccggg taatctgtgt                                                  20

<210> SEQ ID NO 10
<211> LENGTH: 20
<212> TYPE: DNA
<213> ORGANISM: Artificial Sequence
<220> FEATURE:
<223> OTHER INFORMATION: p73 sgRNA sequence

<400> SEQUENCE: 10
tgtcgatagg agtcaaccaa                                                  20

<210> SEQ ID NO 11
<211> LENGTH: 895
<212> TYPE: DNA
<213> ORGANISM: Artificial Sequence
<220> FEATURE:
<223> OTHER INFORMATION: sequence of TET1 LA left homologous arm

<400> SEQUENCE: 11

| | | | | | |
|---|---|---|---|---|---|
| aagcttaagg | ttcacacaac | actaagagct | tttcatcagc | ctcatctact | tctcacctag | 60 |
| tgaaagacga | atctcagac | ttctgtcccc | tgcaggcttc | ctccgcagaa | acatctacct | 120 |
| gtacgtacag | taaaacagcc | tcaggtgggt | ttgcagaaac | aagtagtatt | ctccactgca | 180 |
| caatgccttc | tggagcacac | agtggtgcta | atgcagctgc | tggggaatgt | actggaacgg | 240 |
| tgcagcctgc | cgaggtggct | gctcatcctc | accagtctct | tcccacagcc | gattctcccg | 300 |
| ttcatgctga | gcctctcact | agtccatctg | agcagctaac | ttctaaccag | tcaaaccagc | 360 |
| agctccctct | cctcagcaat | tctcagaaac | tggcttcctg | tcaggtggaa | gatgagcggc | 420 |
| accctgaagc | ggatgagcct | cagcaccccg | aggacgataa | cttgcctcaa | cttgatgaat | 480 |
| tctggtcaga | cagtgaggag | atctacgccg | atccttcctt | tggtggcgtg | gcgatagcac | 540 |
| ccattcacgg | ctcggtgctc | attgagtgcg | ctcggaagga | gcttcatgct | accacctctt | 600 |
| tgcgctcccc | caaacgaggg | gtcccttttc | gtgtgtccct | tgtattctac | cagcacaaaa | 660 |
| gcctaaacaa | gcctaatcat | ggttttgata | tcaacaaaat | taagtgtaaa | tgcaaaaaag | 720 |
| taacgaaaaa | aaagcccgca | gaccgggagt | gtcctgatgt | atcccccgaa | gccaatttat | 780 |
| cacaccaaat | tccttctcga | gttgcatcaa | ccttaacccg | agacaatgtt | gttaccgtgt | 840 |
| ccccatactc | tctcactcat | gttgcgggac | cctacaatcg | ttgggtcgcg | tcgac | 895 |

<210> SEQ ID NO 12
<211> LENGTH: 803
<212> TYPE: DNA
<213> ORGANISM: Artificial Sequence
<220> FEATURE:
<223> OTHER INFORMATION: sequence of TET1 RA right homologous arm

<400> SEQUENCE: 12

| | | | | | |
|---|---|---|---|---|---|
| taaaggcttc | tctcatgtaa | tgcctttgct | aatgtggtgt | agtgggtatt | tttgtttgtt | 60 |
| tgtttgtttt | ctttttgtttt | tttgtttttt | ccggtgctgt | taaaagaaa | gtcattctgt | 120 |
| tgtttactgt | agctttgttt | cgcccatttc | aactccgacg | taaatattaa | aaaaaaaaa | 180 |
| agggtgaata | cttaactgtg | attacatttt | gagaattggt | agaaggtgaa | cattttcagc | 240 |
| aaaaataaac | ttttatagt | tttaaatact | taaaggaaca | tcttggttag | gtgttggcca | 300 |
| tgctagaacc | atagagtctg | gtgctttccc | ccgggtttgt | ttactattca | gagggtttat | 360 |
| aacaggttcc | tgcaataaga | agtaaagacc | aagatgtagt | gttaactcta | cacagttcct | 420 |
| ggtgctttaa | ccacatcaac | acacggagtg | atgagctgag | tgattgtttt | ctggtgccat | 480 |
| tgctcaagcc | tcttccaatc | attgccatcg | tgtctgcaca | tttctttgaa | gtaaaccaat | 540 |
| gaaatgcttt | ttctcttaaa | acatttctcc | tatataaagt | agttctctat | tctcatgatg | 600 |
| gttggaagct | gttcgctaac | tataaatgta | tatattttaa | aaagcacttt | ctactttaa | 660 |
| gagtaacttg | aaatagtata | gtagcagaat | cctattgtct | attatgtgtg | catatttgaa | 720 |
| taccagagaa | gtcatttgtt | cttgctctgt | agagtcccat | cccgttaacc | tcagcctgta | 780 |
| ctcaaataac | acacggcttc | tgt | | | | 803 |

<210> SEQ ID NO 13

```
<211> LENGTH: 809
<212> TYPE: DNA
<213> ORGANISM: Artificial Sequence
<220> FEATURE:
<223> OTHER INFORMATION: sequence of TET3 LA left homologous arm

<400> SEQUENCE: 13
ctggtcccag cctaactgag aagccatggg ggatgggaac cggggatttc aaccccgccc    60
tgaaaggtgg acctgggttc caagacaagt tgtggaatcc tgtgaaggtg gaggagggca   120
ggattcccac accgggggcc aacccgctag acaaagcctg gcaagccttt ggcatgccct   180
tgagctccaa cgagaagcta tttggggccc tgaagtcaga ggagaaactg tgggatccct   240
tcagcctgga ggagggggaca gctgaggagc cccccagcaa gggggtggtg aaggaagaga   300
agagtggacc cacagtggaa gaggacgagg aggaactgtg gtcggacagt gaacacaact   360
tcctggatga gaacataggc ggggtggccg tggcccccgc ccattgctcc atcctcatcg   420
agtgtgcccg gcgagagctg catgccacca ctccactcaa aaaacccaac cgctgccacc   480
ccacccgcat ctcgctggtc ttctaccaac acaagaacct caaccagccc aaccacgggc   540
tggcgctctg ggaggccaag atgaagcagc tggcggaacg ggcgcggcag cggcaagagg   600
aggccgcacg cctgggcctg ggccagcagg aggccaagct ctacgggaag aagcgaaaat   660 ggggggggtgc tatggtggct gagccccagc acaaagaaaa aagggggct atccctaccc   720 ggcaggcgct ggccatgccc acagactccg cggtcaccgt gtcctcttac gcctacacaa   780
aggtcactgg cccctacagc cgctggatc                                    809

<210> SEQ ID NO 14
<211> LENGTH: 837
<212> TYPE: DNA
<213> ORGANISM: Artificial Sequence
<220> FEATURE:
<223> OTHER INFORMATION: sequence of TET3 RA right homologous arm

<400> SEQUENCE: 14
taggtgccag gagccagcgt acctcagcgt cgggcccggc ccgagctgct ctgtggtgct    60
tttgccctca tgcccggggg cgggttgggg gtgcagaagt ctctctatat ctacatatat   120
ggatatgctt atcatatata tgtatttatg gtccaaacct cagaactgac ccgccctccc   180
tcctcttctt ccccagcact ttgaagaaac tacggctgtc gggtgatttt ttttttttt    240 tgatcttaat atttatatct ccacgtttta ttttcccct tgttttgagg gggcttttat    300
tttccttttg tttttaaaac tttatccttg tatatcacaa taatgaaaag aaagtttata   360
gtgtcctttc acaaaggagc gtagttttaa aattccattt aaaatatgta tttattgggt   420
ttttttaaag caacaatagt aatgggttac aggtgggcag gaaaggccgg cagtgcttcc   480
tgcctggcaa gcccagcctc ctggggctg caggctctct cagccatctg ccccacaaac    540
caaggttagc atgtagccct ggtctatccc tccttcccac aggctgggga gcctttggg    600 accaccccgt tctcctctgt ggaatggggg aagctgcaga catctggggg cctggcctgg   660
aaatgctggt gttagatatc cccagaaacc aggttggaag tagacagctt caagcttgct   720
agtctccaca ctgaatcctc tctgtccgtt atttaccaag tcatatgatg tcctggttcg   780
ctaggcagca cctcaagctg gagcaggagt cgagaggctc cgaggagctc ttctcgt      837

<210> SEQ ID NO 15
<211> LENGTH: 824
<212> TYPE: DNA
<213> ORGANISM: Artificial Sequence
```

<220> FEATURE:
<223> OTHER INFORMATION: sequence of TET2 LA left homologous arm

<400> SEQUENCE: 15

```
caaatgtaca ccacctagca acgttttctc cttaccccac ccccaagatg gatagtcatt    60
tcatgggagc tgcctccaga tcaccataca gccacccaca cactgactac aaaaccagtg   120
agcatcatct accctctcac acgatctaca gctacacggc agcagcttcg gggagcagtt   180
ccagccacgc cttccacaac aaggagaatg acaacatagc caatgggctc tcaagagtgc   240
ttccagggtt taatcatgat agaactgctt ctgcccaaga actattatac agtctgactg   300
gcagcagtca ggagaagcag cctgaggtgt caggccagga tgcagctgct gtgcaggaaa   360
ttgagtattg gtcagatagt gagcacaact ttcaggatcc ttgcattgga ggggtggcta   420
tagctccaac tcatgggtca attcttattg agtgtgcaaa gtgtgaggtt catgccacaa   480
ccaaagtaaa cgatcccgac cggaatcacc ccaccaggat ctcacttgta ctgtataggc   540
ataagaattt gtttctacca aaacattgtt tggctctctg ggaagccaaa atggctgaaa   600
aggcccggaa agaggaagag tgcggaaaga atggatcaga ccacgtgtct cagaaaaatc   660
atggcaaaca ggaaaagcgt gagcccacag ggccacagga acccagttac ctgcgtttca   720
tccagtctct tgctgagaac acagggtctg tgactacgga ttctaccgtg actacatcac   780
catatgcttt cactcaggtc acagggcctt acaacacatt tgta                    824
```

<210> SEQ ID NO 16
<211> LENGTH: 792
<212> TYPE: DNA
<213> ORGANISM: Artificial Sequence
<220> FEATURE:
<223> OTHER INFORMATION: sequence of TET2 RA right homologous arm

<400> SEQUENCE: 16

```
tgacgctggc cattaggcca gaccaccaag gacgacctgt gagcagtatg tctttcatgg    60
catgggccgt agggacaggt cacagcatct gtgacaaatg cagtgtgtgt ttgtgtgtat   120
gtttattggg gggggctgt cagctcacca gcaaaatagt ttattttatc attatatttta   180
atctctcccg tggtccatgg tggcattcag gaagagcatc ctatgcaagg gcacagtggg   240
aaggaagcgc tggacatttg tcttgaaaac cactggttct cttattggct gaggtcatgc   300
gtgtgccatg cccctcagca ctctacacgt aactgcttct agtactcagc gtgtgtaacc   360
gtgggacaca gcgctgtagt agagcagttg caggatcatc tggtgctgac gtatgatgta   420
ctgaagaaat actggaacta agacttttta acatgcaggt tttttactgt aatcttaata   480
acttatttat caaagtagct acagaaagct taagtgaata atggcaaaac actgaatctg   540
tttgggtgtt aacattaaat ggtgctacaa atggtgtttt taatagctga aaaatcaatg   600
ccttctatca tctagccagt gtggtcgagg gccctggagg cactggggta cctctgattt   660
tacatttcta tcttaattat tcagcttagt ttttaaaatg tggacatttc aaaggcctct   720
ggattgtagt tatccaccga tgtccttgta ggactataat gtatagatat gcacacttac   780
acatgtgtac tg                                                       792
```

<210> SEQ ID NO 17
<211> LENGTH: 53
<212> TYPE: DNA
<213> ORGANISM: Artificial Sequence
<220> FEATURE:
<223> OTHER INFORMATION: H19!wDMR-IG!wDMR-AGH-4:

<400> SEQUENCE: 17
tgtcgcccgt acagagctcc atggcacagg cgctaggcta cataccatcc tga        53

<210> SEQ ID NO 18
<211> LENGTH: 56
<212> TYPE: DNA
<213> ORGANISM: Artificial Sequence
<220> FEATURE:
<223> OTHER INFORMATION: IG!wDMR-H19!wDMR-AGH-2

<400> SEQUENCE: 18
gacataagtc ttggccatga actcagaaca atggtatacg cacgcacgtg gctgga     56

<210> SEQ ID NO 19
<211> LENGTH: 33
<212> TYPE: DNA
<213> ORGANISM: Artificial Sequence
<220> FEATURE:
<223> OTHER INFORMATION: Tet1 wild-type sequence

<400> SEQUENCE: 19
ggctgctgtc agggagctca tggagactag gtg                              33

<210> SEQ ID NO 20
<211> LENGTH: 32
<212> TYPE: DNA
<213> ORGANISM: Artificial Sequence
<220> FEATURE:
<223> OTHER INFORMATION: Gene mutation of Tet1 in Tet-TKO-DAH-1

<400> SEQUENCE: 20
ggctgctgtc agggagtcat ggagactagg tg                               32

<210> SEQ ID NO 21
<211> LENGTH: 32
<212> TYPE: DNA
<213> ORGANISM: Artificial Sequence
<220> FEATURE:
<223> OTHER INFORMATION: Tet2 wild-type sequence

<400> SEQUENCE: 21
gtgccaacag atatccaggc tgcagaatcg ga                               32

<210> SEQ ID NO 22
<211> LENGTH: 28
<212> TYPE: DNA
<213> ORGANISM: Artificial Sequence
<220> FEATURE:
<223> OTHER INFORMATION: Gene mutation of Tet2 in Tet-TKO-DAH-1

<400> SEQUENCE: 22
gtgccaacag atagtctgca gaatcgga                                    28

<210> SEQ ID NO 23
<211> LENGTH: 32
<212> TYPE: DNA
<213> ORGANISM: Artificial Sequence
<220> FEATURE:
<223> OTHER INFORMATION: Tet3 wild-type sequence

<400> SEQUENCE: 23
aggaggggaa gagttctcga ggctgtccca tc                               32

<210> SEQ ID NO 24
<211> LENGTH: 30

```
<212> TYPE: DNA
<213> ORGANISM: Artificial Sequence
<220> FEATURE:
<223> OTHER INFORMATION: Gene mutation of Tet3 in Tet-TKO-DAH-1

<400> SEQUENCE: 24
aggaggggaa gagttcgagg ctgtcccatc                                     30

<210> SEQ ID NO 25
<211> LENGTH: 33
<212> TYPE: DNA
<213> ORGANISM: Artificial Sequence
<220> FEATURE:
<223> OTHER INFORMATION: P53 wild-type sequence

<400> SEQUENCE: 25
cctgggcttc ctgcagtctg ggacagccaa gtc                                 33

<210> SEQ ID NO 26
<211> LENGTH: 26
<212> TYPE: DNA
<213> ORGANISM: Artificial Sequence
<220> FEATURE:
<223> OTHER INFORMATION: Gene mutation of P53 in P53-TKO-DAH-2

<400> SEQUENCE: 26
cctgggcttc ctgggacagc caagtc                                         26

<210> SEQ ID NO 27
<211> LENGTH: 33
<212> TYPE: DNA
<213> ORGANISM: Artificial Sequence
<220> FEATURE:
<223> OTHER INFORMATION: P63 wild-type sequence

<400> SEQUENCE: 27
ttccctccaa cacagattac ccgggcccac aca                                 33

<210> SEQ ID NO 28
<211> LENGTH: 26
<212> TYPE: DNA
<213> ORGANISM: Artificial Sequence
<220> FEATURE:
<223> OTHER INFORMATION: Gene mutation of P63 in P53-TKO-DAH-2

<400> SEQUENCE: 28
ttccctccaa cacccgggcc cacaca                                         26

<210> SEQ ID NO 29
<211> LENGTH: 33
<212> TYPE: DNA
<213> ORGANISM: Artificial Sequence
<220> FEATURE:
<223> OTHER INFORMATION: P73 wild-type sequence

<400> SEQUENCE: 29
gtgccccagc ctttggttga ctcctatcga cag                                 33

<210> SEQ ID NO 30
<211> LENGTH: 29
<212> TYPE: DNA
<213> ORGANISM: Artificial Sequence
<220> FEATURE:
<223> OTHER INFORMATION: Gene mutation of P73 in P53-TKO-DAH-2

<400> SEQUENCE: 30
```

```
gtgcccagc ctttgactcc tatcgacag                                          29

<210> SEQ ID NO 31
<211> LENGTH: 59
<212> TYPE: DNA
<213> ORGANISM: Artificial Sequence
<220> FEATURE:
<223> OTHER INFORMATION: H19!wDMR-IG!wDMR-AGH-OG3-1(IG KO)

<400> SEQUENCE: 31
gtttgcggtt ttcaggatgg tatgtaccct acccatggag ctctgtacgg gcgacatga     59

<210> SEQ ID NO 32
<211> LENGTH: 59
<212> TYPE: DNA
<213> ORGANISM: Artificial Sequence
<220> FEATURE:
<223> OTHER INFORMATION: H19!wDMR-IG!wDMR-AGH-OG3-1 (H19 KO)

<400> SEQUENCE: 32
tcaagggctg accagtcatg accactcatc atggccaaga cttatgtcct aaactcaca     59

<210> SEQ ID NO 33
<211> LENGTH: 59
<212> TYPE: DNA
<213> ORGANISM: Artificial Sequence
<220> FEATURE:
<223> OTHER INFORMATION: H19!wDMR-IG!wDMR-AGH-OG3-2(IG KO)

<400> SEQUENCE: 33
tgtgtgtgtg tgtacataca agcctacatg tatctctgta cgggcgacat gagcatgac    59

<210> SEQ ID NO 34
<211> LENGTH: 58
<212> TYPE: DNA
<213> ORGANISM: Artificial Sequence
<220> FEATURE:
<223> OTHER INFORMATION: H19!wDMR-IG!wDMR-AGH-OG3-2 (H19 KO)

<400> SEQUENCE: 34
ggaggactca agggctgacc agtcatgacc acttctgagt tcatggccaa gacttatg     58

<210> SEQ ID NO 35
<211> LENGTH: 38
<212> TYPE: DNA
<213> ORGANISM: Artificial Sequence
<220> FEATURE:
<223> OTHER INFORMATION: Iqcf5 wild-type sequence

<400> SEQUENCE: 35
acgttgctgc atgctgccct cagcgcgtgg atcattca                             38

<210> SEQ ID NO 36
<211> LENGTH: 33
<212> TYPE: DNA
<213> ORGANISM: Artificial Sequence
<220> FEATURE:
<223> OTHER INFORMATION: Iqcf5 mutant gene sequence

<400> SEQUENCE: 36
acgttgctgc atgctgcccg cgtggatcat tca                                  33

<210> SEQ ID NO 37
<211> LENGTH: 38
<212> TYPE: DNA
<213> ORGANISM: Artificial Sequence
```

```
<220> FEATURE:
<223> OTHER INFORMATION: Olfr1247 wild-type sequence

<400> SEQUENCE: 37
gtttgtatct cacttttggt ggtagcctgg gttggggg                              38

<210> SEQ ID NO 38
<211> LENGTH: 37
<212> TYPE: DNA
<213> ORGANISM: Artificial Sequence
<220> FEATURE:
<223> OTHER INFORMATION: Olfr1247 mutant gene sequence

<400> SEQUENCE: 38
gtttgtatct cacttttggt ggtacctggg ttggggg                               37

<210> SEQ ID NO 39
<211> LENGTH: 38
<212> TYPE: DNA
<213> ORGANISM: Artificial Sequence
<220> FEATURE:
<223> OTHER INFORMATION: Kbtbd2 wild-type sequence

<400> SEQUENCE: 39
taatagctta cgcgtacaca gggaacttgg cagtaaac                              38

<210> SEQ ID NO 40
<211> LENGTH: 27
<212> TYPE: DNA
<213> ORGANISM: Artificial Sequence
<220> FEATURE:
<223> OTHER INFORMATION: Kbtbd2 mutant gene sequence

<400> SEQUENCE: 40
taatagctta cgcgtacggc agtaaac                                          27

<210> SEQ ID NO 41
<211> LENGTH: 38
<212> TYPE: DNA
<213> ORGANISM: Artificial Sequence
<220> FEATURE:
<223> OTHER INFORMATION: Hmox1 wild-type sequence

<400> SEQUENCE: 41
ccctgagctg ctggtggccc acgcatatac ccgctacc                              38

<210> SEQ ID NO 42
<211> LENGTH: 33
<212> TYPE: DNA
<213> ORGANISM: Artificial Sequence
<220> FEATURE:
<223> OTHER INFORMATION: Hmox1 mutant gene sequence

<400> SEQUENCE: 42
ccctgagctg ctggtggccc acgacccgct acc                                   33

<210> SEQ ID NO 43
<211> LENGTH: 38
<212> TYPE: DNA
<213> ORGANISM: Artificial Sequence
<220> FEATURE:
<223> OTHER INFORMATION: Fibp wild-type sequence

<400> SEQUENCE: 43
tgcgagtacg ctccggaatc ttggagcaga cgggagcc                              38
```

<210> SEQ ID NO 44
<211> LENGTH: 36
<212> TYPE: DNA
<213> ORGANISM: Artificial Sequence
<220> FEATURE:
<223> OTHER INFORMATION: Fibp mutant gene sequence

<400> SEQUENCE: 44
tgcgagtacg ctccggactt ggagcagacg ggagcc                          36

<210> SEQ ID NO 45
<211> LENGTH: 38
<212> TYPE: DNA
<213> ORGANISM: Artificial Sequence
<220> FEATURE:
<223> OTHER INFORMATION: Csf2 wild-type sequence

<400> SEQUENCE: 45
gagttctcct tcaaggtaag ctgcttctct tttgctct                        38

<210> SEQ ID NO 46
<211> LENGTH: 30
<212> TYPE: DNA
<213> ORGANISM: Artificial Sequence
<220> FEATURE:
<223> OTHER INFORMATION: Csf2 mutant gene sequence

<400> SEQUENCE: 46
gagttctcct tcaagcttct cttttgctct                                 30

<210> SEQ ID NO 47
<211> LENGTH: 38
<212> TYPE: DNA
<213> ORGANISM: Artificial Sequence
<220> FEATURE:
<223> OTHER INFORMATION: Vav3 wild-type sequence

<400> SEQUENCE: 47
ttgaagaaca tccggacatt cctggccgcc tgctgcga                        38

<210> SEQ ID NO 48
<211> LENGTH: 37
<212> TYPE: DNA
<213> ORGANISM: Artificial Sequence
<220> FEATURE:
<223> OTHER INFORMATION: Vav3 mutant gene sequence

<400> SEQUENCE: 48
ttgaagaaca tccggacatc ctggccgcct gctgcga                         37

<210> SEQ ID NO 49
<211> LENGTH: 38
<212> TYPE: DNA
<213> ORGANISM: Artificial Sequence
<220> FEATURE:
<223> OTHER INFORMATION: Lrrc61 wild-type sequence

<400> SEQUENCE: 49
gtcccactca ggagaatttg ccctggattc catcctgt                        38

<210> SEQ ID NO 50
<211> LENGTH: 19
<212> TYPE: DNA
<213> ORGANISM: Artificial Sequence
<220> FEATURE:
<223> OTHER INFORMATION: Lrrc61 mutant gene sequence

```
<400> SEQUENCE: 50
gtcccactca ggagaattt                                                 19

<210> SEQ ID NO 51
<211> LENGTH: 30
<212> TYPE: DNA
<213> ORGANISM: Artificial Sequence
<220> FEATURE:
<223> OTHER INFORMATION: Tet1 wild-type sequence

<400> SEQUENCE: 51
ctgctgtcag ggagctcatg gagactaggt                                     30

<210> SEQ ID NO 52
<211> LENGTH: 31
<212> TYPE: DNA
<213> ORGANISM: Artificial Sequence
<220> FEATURE:
<223> OTHER INFORMATION: Gene mutation of Tet1 in Tet-TKO-DAH-3

<400> SEQUENCE: 52
ctgctgtcag ggagcctcat ggagactagg t                                   31

<210> SEQ ID NO 53
<211> LENGTH: 32
<212> TYPE: DNA
<213> ORGANISM: Artificial Sequence
<220> FEATURE:
<223> OTHER INFORMATION: Tet2 wild-type sequence

<400> SEQUENCE: 53
aagtgccaac agatatccag gctgcagaat cg                                  32

<210> SEQ ID NO 54
<211> LENGTH: 30
<212> TYPE: DNA
<213> ORGANISM: Artificial Sequence
<220> FEATURE:
<223> OTHER INFORMATION: Gene mutation of Tet2 in Tet-TKO-DAH-3

<400> SEQUENCE: 54
aagtgccaac agatacaggc tgcagaatcg                                     30

<210> SEQ ID NO 55
<211> LENGTH: 32
<212> TYPE: DNA
<213> ORGANISM: Artificial Sequence
<220> FEATURE:
<223> OTHER INFORMATION: Tet3 wild-type sequence

<400> SEQUENCE: 55
ggaagagttc tcgaggctgt cccatcgcca ag                                  32

<210> SEQ ID NO 56
<211> LENGTH: 33
<212> TYPE: DNA
<213> ORGANISM: Artificial Sequence
<220> FEATURE:
<223> OTHER INFORMATION: Gene mutation of Tet3 in Tet-TKO-DAH-3

<400> SEQUENCE: 56
ggaagagttc ttcgaggctg tcccatcgcc aag                                 33

<210> SEQ ID NO 57
```

```
<211> LENGTH: 32
<212> TYPE: DNA
<213> ORGANISM: Artificial Sequence
<220> FEATURE:
<223> OTHER INFORMATION: P53 wild-type sequence

<400> SEQUENCE: 57
acctgggctt cctgcagtct gggacagcca ag                                   32

<210> SEQ ID NO 58
<211> LENGTH: 33
<212> TYPE: DNA
<213> ORGANISM: Artificial Sequence
<220> FEATURE:
<223> OTHER INFORMATION: Gene mutation of P53 in P53-TKO-DAH-1

<400> SEQUENCE: 58
acctgggctt cctgcaagtc tgggacagcc aag                                  33

<210> SEQ ID NO 59
<211> LENGTH: 33
<212> TYPE: DNA
<213> ORGANISM: Artificial Sequence
<220> FEATURE:
<223> OTHER INFORMATION: P63 wild-type sequence

<400> SEQUENCE: 59
ccattccctc caacacagat tacccgggcc cac                                  33

<210> SEQ ID NO 60
<211> LENGTH: 29
<212> TYPE: DNA
<213> ORGANISM: Artificial Sequence
<220> FEATURE:
<223> OTHER INFORMATION: Gene mutation of P63 in P53-TKO-DAH-1

<400> SEQUENCE: 60
ccattccctc caacattacc cgggcccac                                       29

<210> SEQ ID NO 61
<211> LENGTH: 82
<212> TYPE: DNA
<213> ORGANISM: Artificial Sequence
<220> FEATURE:
<223> OTHER INFORMATION: P73 wild-type sequence

<400> SEQUENCE: 61
ctttgagatc ttgatgaaag tcaaggagag cctagaactg atggagcttg tgccccagcc     60
tttggttgac tcctatcgac ag                                              82

<210> SEQ ID NO 62
<211> LENGTH: 20
<212> TYPE: DNA
<213> ORGANISM: Artificial Sequence
<220> FEATURE:
<223> OTHER INFORMATION: Gene mutation of P73 in P53-TKO-DAH-1

<400> SEQUENCE: 62
ctttgagatc ctatcgacag                                                 20

<210> SEQ ID NO 63
<211> LENGTH: 30
<212> TYPE: DNA
<213> ORGANISM: Artificial Sequence
<220> FEATURE:
<223> OTHER INFORMATION: polm gene mutation in the mouse tail by TA
``` cloning and sequencing

<400> SEQUENCE: 63
ccttcctcac ccgcgcggtc caaaggcttc                                     30

<210> SEQ ID NO 64
<211> LENGTH: 34
<212> TYPE: DNA
<213> ORGANISM: Artificial Sequence
<220> FEATURE:
<223> OTHER INFORMATION: polm gene mutation in the mouse tail by TA
      cloning and sequencing

<400> SEQUENCE: 64
ttcctcaccc gcctgggcgc ggtccaaagg cttc                                34

<210> SEQ ID NO 65
<211> LENGTH: 28
<212> TYPE: DNA
<213> ORGANISM: Artificial Sequence
<220> FEATURE:
<223> OTHER INFORMATION: polm gene mutation in the mouse tail by TA
      cloning and sequencing

<400> SEQUENCE: 65
ccttcctcac ccgcggtcca aaggcttc                                       28

<210> SEQ ID NO 66
<211> LENGTH: 35
<212> TYPE: DNA
<213> ORGANISM: Artificial Sequence
<220> FEATURE:
<223> OTHER INFORMATION: polm gene mutation in the mouse tail by TA
      cloning and sequencing

<400> SEQUENCE: 66
cttcctcacc cgcctcaccc gcgcggtcca aaggc                               35

<210> SEQ ID NO 67
<211> LENGTH: 35
<212> TYPE: DNA
<213> ORGANISM: Artificial Sequence
<220> FEATURE:
<223> OTHER INFORMATION: polm gene mutation in the mouse tail by TA
      cloning and sequencing

<400> SEQUENCE: 67
ccttcctcac ccgcctggcg cggtccaaag gcttc                               35

<210> SEQ ID NO 68
<211> LENGTH: 807
<212> TYPE: DNA
<213> ORGANISM: Artificial Sequence
<220> FEATURE:
<223> OTHER INFORMATION: Sequencing of Tet1-EGFP

<400> SEQUENCE: 68
tgtgtctatg aactaccagt gagatagttt tttgtttttt gttttttgt tttgtttttc     60 aaggttcaca caacactaag agcttttcat cagcctcatc tacttctcac ctagtgaagc   120
atcaacctta acccgagaca atgttgttac cgtgtcccca tactctctca ctcatgttgc   180
gggaccctac aatcgttggg tcgcgtcgac gattgccacg aagcaagcag gagatgttga   240
agaaaacccc gggcctgtga gcaagggcga ggagctgttc accggggtgg tgcccatcct   300
ggtcgagctg gacggcgacg taaacggcca caagttcagc gtccgacaac cactacctga   360

```
gcacccagtc cgccctgagc aaagacccca acgagaagcg cgatcacatg gtcctgctgg    420
agttcgtgac cgccgccggg atcactctcg gcatggacga gctgtacaag aatctctaga    480
gctaaaggct tctctcatgt aatgcctttg ctaatgtggt gtagtgggta tttttgtttg    540
tttgtttgtt ttcttttgtt ttttttttt tccggtgctg ttaaaagaa agtcattctg      600 ttgtttactg tagctttgtt tcgcccattg ttcttgctct gtagagtccc atcccgttaa    660
cctcagcctg tactcaaata acacacggct tctgttcttt acttatagaa tagagggtct    720
ctaaaaaaaa aaatttaaat acaagatgct accaatatca attttccctc tttaactaga    780
aaaaatattg tcttctgaag tcacctc                                        807

<210> SEQ ID NO 69
<211> LENGTH: 671
<212> TYPE: DNA
<213> ORGANISM: Artificial Sequence
<220> FEATURE:
<223> OTHER INFORMATION: Sequencing of Tet3-ECFP

<400> SEQUENCE: 69
gcttcgaggc aagccatgga gccctgcaa gtttgggaac ggcacctctg ccttgactgg      60
tcccagccta actgagaagc catgggggat gggaaccggg gatttcaacc ccgcaggcgc    120
tggccatgcc cacagactcc gcggtcaccg tgtcctctta cgcctacaca aaggtcactg    180
gcccctacag ccgctggatc gcgtcgacga ttgccacgaa gcaagcagga gatgttgaag    240
aaaaccccgg gcctgtgagc aagggcgagg agctgttcac cggggtggtg cccatcctgg    300
tcgagctgga cggcgacgta acggccaca agttgagaag cgcgatcaca tggtcctgct    360
ggagttcgtg accgccgccg ggatcactct cggcatggac gagctgtaca agaatctcta    420
gagctaggtg ccaggagcca cgtacctcg ggcccggccc gagctgctct gtggtgcttt     480
tgccctcatg cccgggggcg gtggttcgct aggcagcacc tcaagctgga gcaggagtcg    540
agaggctccg aggagctctt ctcgtcccgt tgataaagcc ggtgagtact gggccgaaag    600
gaagcttagt ggcagttttc ttaaaaatcg ccccaaagtt tgtcgatact gaaaaggggc    660
tactgtatct a                                                         671

<210> SEQ ID NO 70
<211> LENGTH: 728
<212> TYPE: DNA
<213> ORGANISM: Artificial Sequence
<220> FEATURE:
<223> OTHER INFORMATION: Sequencing of Tet2-mCherry

<400> SEQUENCE: 70
agatgccttc actactaact ccaccctaaa accaaatgta caccacctag caacgttttc     60
tccttacccc acccccaaga tggatagtca tttcatggga gctgcctcca gatcaacagg    120
gtctgtgact acggattcta ccgtgactac atcaccatat gctttcactc aggtcacagg    180
gccttacaac acatttgtag cgtcgacgat tgccacgaag caagcaggag atgttgaaga    240
aaaccccggg cctgtgagca agggcgagga ggataacatg gccatcatca aggagttcat    300
gcgcttcaag gtgcacatgg agggctccgt gaacggccac gcgcctacaa cgtcaacatc    360
aagttggaca tcacctccca caacgaggac tacaccatcg tggaacagta cgaacgcgcc    420
gagggccgcc actccaccgg cggcatggac gagctgtaca agaatctcta gagctgacgc    480
tggccattag gccagaccac caaggacgac ctgtgagcag tatgtctttc atggcatggg    540
```

```
ccgtagggac aggtcacagc atctatctta attattcagc ttagttttta aaatgtggac    600
atttcaaagg cctctggatt gtagttatcc accgatgtcc ttgtaggact ataatgtata    660
gatatgcaca cttacacatg tgtactgaaa tattttaagt tgtgtcttag aaaagcactt    720
tgcctacc                                                            728

<210> SEQ ID NO 71
<211> LENGTH: 39
<212> TYPE: DNA
<213> ORGANISM: Artificial Sequence
<220> FEATURE:
<223> OTHER INFORMATION: Genetic modification in Slco5a1

<400> SEQUENCE: 71
ctgactttca tccaggccat taatggtctc tgggtacct                           39

<210> SEQ ID NO 72
<211> LENGTH: 30
<212> TYPE: DNA
<213> ORGANISM: Artificial Sequence
<220> FEATURE:
<223> OTHER INFORMATION: Genetic modification in Slco5a1

<400> SEQUENCE: 72
ctgactttca ttaatggtct ctgggtacct                                     30

<210> SEQ ID NO 73
<211> LENGTH: 35
<212> TYPE: DNA
<213> ORGANISM: Artificial Sequence
<220> FEATURE:
<223> OTHER INFORMATION: Genetic modification in Slco5a1

<400> SEQUENCE: 73
ctgactttca tccatttaat ggtctctggg tacct                               35

<210> SEQ ID NO 74
<211> LENGTH: 38
<212> TYPE: DNA
<213> ORGANISM: Artificial Sequence
<220> FEATURE:
<223> OTHER INFORMATION: Slco5a1 wild type

<400> SEQUENCE: 74
ctgactttca tccaggcgtt aatggtctct gggtacct                            38

<210> SEQ ID NO 75
<211> LENGTH: 30
<212> TYPE: DNA
<213> ORGANISM: Artificial Sequence
<220> FEATURE:
<223> OTHER INFORMATION: mCherry-F

<400> SEQUENCE: 75
atttgcggcc gcatagtaat caattacggg                                     30

<210> SEQ ID NO 76
<211> LENGTH: 30
<212> TYPE: DNA
<213> ORGANISM: Artificial Sequence
<220> FEATURE:
<223> OTHER INFORMATION: mCherry-R

<400> SEQUENCE: 76
atttgcggcc gcatgcagtg aaaaaaatgc                                     30
```

<210> SEQ ID NO 77
<211> LENGTH: 20
<212> TYPE: DNA
<213> ORGANISM: Artificial Sequence
<220> FEATURE:
<223> OTHER INFORMATION: Gtl2-F

<400> SEQUENCE: 77
ttgcacattt cctgtgggac                                               20

<210> SEQ ID NO 78
<211> LENGTH: 20
<212> TYPE: DNA
<213> ORGANISM: Artificial Sequence
<220> FEATURE:
<223> OTHER INFORMATION: Gtl2-R

<400> SEQUENCE: 78
aagcaccatg agccactagg                                               20

<210> SEQ ID NO 79
<211> LENGTH: 35
<212> TYPE: DNA
<213> ORGANISM: Artificial Sequence
<220> FEATURE:
<223> OTHER INFORMATION: IG DMR-BS-OF

<400> SEQUENCE: 79
ttaaggtatt ttttattgat aaaataatgt agttt                              35

<210> SEQ ID NO 80
<211> LENGTH: 35
<212> TYPE: DNA
<213> ORGANISM: Artificial Sequence
<220> FEATURE:
<223> OTHER INFORMATION: IGD MR-BS-OR

<400> SEQUENCE: 80
cctactctat aataccctat ataattatac cataa                              35

<210> SEQ ID NO 81
<211> LENGTH: 34
<212> TYPE: DNA
<213> ORGANISM: Artificial Sequence
<220> FEATURE:
<223> OTHER INFORMATION: IG DMR-BS-IF

<400> SEQUENCE: 81
ttaggagtta aggaaaagaa agaaatagta tagt                               34

<210> SEQ ID NO 82
<211> LENGTH: 35
<212> TYPE: DNA
<213> ORGANISM: Artificial Sequence
<220> FEATURE:
<223> OTHER INFORMATION: IG DMR-BS-IR

<400> SEQUENCE: 82
tatacacaaa aatatatcta tataacacca tacaa                              35

<210> SEQ ID NO 83
<211> LENGTH: 20
<212> TYPE: DNA
<213> ORGANISM: Artificial Sequence
<220> FEATURE:

<223> OTHER INFORMATION: IG-DMR deletion check-F

<400> SEQUENCE: 83
tgtgcagcag caaagctaag                                              20

<210> SEQ ID NO 84
<211> LENGTH: 20
<212> TYPE: DNA
<213> ORGANISM: Artificial Sequence
<220> FEATURE:
<223> OTHER INFORMATION: IG-DMR deletion check-R

<400> SEQUENCE: 84
atacgatacg gcaaccaacg                                              20

<210> SEQ ID NO 85
<211> LENGTH: 24
<212> TYPE: DNA
<213> ORGANISM: Artificial Sequence
<220> FEATURE:
<223> OTHER INFORMATION: H19 DMR-BS-OF

<400> SEQUENCE: 85
gagtatttag gaggtataag aatt                                         24

<210> SEQ ID NO 86
<211> LENGTH: 23
<212> TYPE: DNA
<213> ORGANISM: Artificial Sequence
<220> FEATURE:
<223> OTHER INFORMATION: H19 DMR-BS-OR

<400> SEQUENCE: 86
atcaaaaact aacataaacc cct                                          23

<210> SEQ ID NO 87
<211> LENGTH: 25
<212> TYPE: DNA
<213> ORGANISM: Artificial Sequence
<220> FEATURE:
<223> OTHER INFORMATION: H19 DMR-BS-IF

<400> SEQUENCE: 87
gtaaggagat tatgtttatt tttgg                                        25

<210> SEQ ID NO 88
<211> LENGTH: 21
<212> TYPE: DNA
<213> ORGANISM: Artificial Sequence
<220> FEATURE:
<223> OTHER INFORMATION: H19 DMR-BS-IR

<400> SEQUENCE: 88
cctcattaat cccataacta t                                            21

<210> SEQ ID NO 89
<211> LENGTH: 20
<212> TYPE: DNA
<213> ORGANISM: Artificial Sequence
<220> FEATURE:
<223> OTHER INFORMATION: H19-DMR deletion check-F2

<400> SEQUENCE: 89
gtggttagtt ctatatgggg                                              20

```
<210> SEQ ID NO 90
<211> LENGTH: 20
<212> TYPE: DNA
<213> ORGANISM: Artificial Sequence
<220> FEATURE:
<223> OTHER INFORMATION: H19-DMR deletion check-R2

<400> SEQUENCE: 90
tcttacagtc tggtcttggt                                               20

<210> SEQ ID NO 91
<211> LENGTH: 20
<212> TYPE: DNA
<213> ORGANISM: Artificial Sequence
<220> FEATURE:
<223> OTHER INFORMATION: IG-DMR deletion check-F

<400> SEQUENCE: 91
tgtgcagcag caaagctaag                                               20

<210> SEQ ID NO 92
<211> LENGTH: 20
<212> TYPE: DNA
<213> ORGANISM: Artificial Sequence
<220> FEATURE:
<223> OTHER INFORMATION: IG-DMR deletion check-R

<400> SEQUENCE: 92
atacgatacg gcaaccaacg                                               20

<210> SEQ ID NO 93
<211> LENGTH: 20
<212> TYPE: DNA
<213> ORGANISM: Artificial Sequence
<220> FEATURE:
<223> OTHER INFORMATION: Gapdh-F

<400> SEQUENCE: 93
cactcttcca ccttcgatgc                                               20

<210> SEQ ID NO 94
<211> LENGTH: 20
<212> TYPE: DNA
<213> ORGANISM: Artificial Sequence
<220> FEATURE:
<223> OTHER INFORMATION: Gapdh-R

<400> SEQUENCE: 94
ctcttgctca gtgtccttgc                                               20

<210> SEQ ID NO 95
<211> LENGTH: 22
<212> TYPE: DNA
<213> ORGANISM: Artificial Sequence
<220> FEATURE:
<223> OTHER INFORMATION: Igf2-F

<400> SEQUENCE: 95
ctaagacttg gatcccagaa cc                                            22

<210> SEQ ID NO 96
<211> LENGTH: 22
<212> TYPE: DNA
<213> ORGANISM: Artificial Sequence
<220> FEATURE:
<223> OTHER INFORMATION: Igf2-R
```

```
<400> SEQUENCE: 96
gttcttctcc ttgggttctt tc                                            22

<210> SEQ ID NO 97
<211> LENGTH: 20
<212> TYPE: DNA
<213> ORGANISM: Artificial Sequence
<220> FEATURE:
<223> OTHER INFORMATION: Gtl2-F

<400> SEQUENCE: 97
ttgcacattt cctgtgggac                                               20

<210> SEQ ID NO 98
<211> LENGTH: 20
<212> TYPE: DNA
<213> ORGANISM: Artificial Sequence
<220> FEATURE:
<223> OTHER INFORMATION: Gtl2-R

<400> SEQUENCE: 98
aagcaccatg agccactagg                                               20

<210> SEQ ID NO 99
<211> LENGTH: 20
<212> TYPE: DNA
<213> ORGANISM: Artificial Sequence
<220> FEATURE:
<223> OTHER INFORMATION: Dlk-F

<400> SEQUENCE: 99
acttgcgtgg acctggagaa                                               20

<210> SEQ ID NO 100
<211> LENGTH: 20
<212> TYPE: DNA
<213> ORGANISM: Artificial Sequence
<220> FEATURE:
<223> OTHER INFORMATION: Dlk-R

<400> SEQUENCE: 100
ctgttggttg cggctacgat                                               20

<210> SEQ ID NO 101
<211> LENGTH: 18
<212> TYPE: DNA
<213> ORGANISM: Artificial Sequence
<220> FEATURE:
<223> OTHER INFORMATION: H19-F

<400> SEQUENCE: 101
catgtctggg cctttgaa                                                 18

<210> SEQ ID NO 102
<211> LENGTH: 18
<212> TYPE: DNA
<213> ORGANISM: Artificial Sequence
<220> FEATURE:
<223> OTHER INFORMATION: H19-R

<400> SEQUENCE: 102
ttggctccag gatgatgt                                                 18

<210> SEQ ID NO 103
<211> LENGTH: 21
```

```
<212> TYPE: DNA
<213> ORGANISM: Artificial Sequence
<220> FEATURE:
<223> OTHER INFORMATION: Tet1 check-F

<400> SEQUENCE: 103 gccccctgttg tcttatacgt t                                           21

<210> SEQ ID NO 104
<211> LENGTH: 18
<212> TYPE: DNA
<213> ORGANISM: Artificial Sequence
<220> FEATURE:
<223> OTHER INFORMATION: Tet1 check- R

<400> SEQUENCE: 104
cattcgcctc aggaccac                                                18

<210> SEQ ID NO 105
<211> LENGTH: 21
<212> TYPE: DNA
<213> ORGANISM: Artificial Sequence
<220> FEATURE:
<223> OTHER INFORMATION: Tet2 check- F

<400> SEQUENCE: 105
ccgccacaag aaaatatgtc c                                            21

<210> SEQ ID NO 106
<211> LENGTH: 20
<212> TYPE: DNA
<213> ORGANISM: Artificial Sequence
<220> FEATURE:
<223> OTHER INFORMATION: Tet2 check- R

<400> SEQUENCE: 106
agctaactct ggcaaacacc                                              20

<210> SEQ ID NO 107
<211> LENGTH: 20
<212> TYPE: DNA
<213> ORGANISM: Artificial Sequence
<220> FEATURE:
<223> OTHER INFORMATION: Tet3 check- F

<400> SEQUENCE: 107
cagagtggcc tcagtttccc                                              20

<210> SEQ ID NO 108
<211> LENGTH: 24
<212> TYPE: DNA
<213> ORGANISM: Artificial Sequence
<220> FEATURE:
<223> OTHER INFORMATION: Tet3 check- R

<400> SEQUENCE: 108 acaacttttta cccaggagtc acac                                        24

<210> SEQ ID NO 109
<211> LENGTH: 21
<212> TYPE: DNA
<213> ORGANISM: Artificial Sequence
<220> FEATURE:
<223> OTHER INFORMATION: P53 check- F

<400> SEQUENCE: 109
```
cccctgtcat cttttgtccc t                                          21

<210> SEQ ID NO 110
<211> LENGTH: 21
<212> TYPE: DNA
<213> ORGANISM: Artificial Sequence
<220> FEATURE:
<223> OTHER INFORMATION: P53 check- R

<400> SEQUENCE: 110
aagagagttc cacgtcccct g                                          21

<210> SEQ ID NO 111
<211> LENGTH: 20
<212> TYPE: DNA
<213> ORGANISM: Artificial Sequence
<220> FEATURE:
<223> OTHER INFORMATION: P63 check- F

<400> SEQUENCE: 111
cacaccaaat aatgccaatt                                            20

<210> SEQ ID NO 112
<211> LENGTH: 20
<212> TYPE: DNA
<213> ORGANISM: Artificial Sequence
<220> FEATURE:
<223> OTHER INFORMATION: P63 check- R

<400> SEQUENCE: 112
cagactctct taccgtccag                                            20

<210> SEQ ID NO 113
<211> LENGTH: 20
<212> TYPE: DNA
<213> ORGANISM: Artificial Sequence
<220> FEATURE:
<223> OTHER INFORMATION: P73 check- F

<400> SEQUENCE: 113
gacccacttc taaacctgcc                                            20

<210> SEQ ID NO 114
<211> LENGTH: 20
<212> TYPE: DNA
<213> ORGANISM: Artificial Sequence
<220> FEATURE:
<223> OTHER INFORMATION: P73 check- R

<400> SEQUENCE: 114
ccatacctcc tgtgctcctg                                            20

<210> SEQ ID NO 115
<211> LENGTH: 60
<212> TYPE: DNA
<213> ORGANISM: Artificial Sequence
<220> FEATURE:
<223> OTHER INFORMATION: P2A-fluorescence F

<400> SEQUENCE: 115
gccacgaagc aagcaggaga tgttgaagaa aaccccgggc ctgtgagcaa gggcgaggag    60

<210> SEQ ID NO 116
<211> LENGTH: 19
<212> TYPE: DNA
<213> ORGANISM: Artificial Sequence

```
<220> FEATURE:
<223> OTHER INFORMATION: P2A-fluorescence R

<400> SEQUENCE: 116
cttgtacagc tcgtccatg                                                19

<210> SEQ ID NO 117
<211> LENGTH: 25
<212> TYPE: DNA
<213> ORGANISM: Artificial Sequence
<220> FEATURE:
<223> OTHER INFORMATION: Tet1 LA-F

<400> SEQUENCE: 117
tttgtgtcta tgaactacca gtgag                                         25

<210> SEQ ID NO 118
<211> LENGTH: 19
<212> TYPE: DNA
<213> ORGANISM: Artificial Sequence
<220> FEATURE:
<223> OTHER INFORMATION: Tet1 LA-F

<400> SEQUENCE: 118
caggcccggg gttttcttc                                                19

<210> SEQ ID NO 119
<211> LENGTH: 20
<212> TYPE: DNA
<213> ORGANISM: Artificial Sequence
<220> FEATURE:
<223> OTHER INFORMATION: Tet1 RA-F

<400> SEQUENCE: 119
caacgagaag cgcgatcaca                                               20

<210> SEQ ID NO 120
<211> LENGTH: 23
<212> TYPE: DNA
<213> ORGANISM: Artificial Sequence
<220> FEATURE:
<223> OTHER INFORMATION: Tet1 RA-F

<400> SEQUENCE: 120
ttttgactga tcccaatttg cct                                           23

<210> SEQ ID NO 121
<211> LENGTH: 20
<212> TYPE: DNA
<213> ORGANISM: Artificial Sequence
<220> FEATURE:
<223> OTHER INFORMATION: Tet3 LA-F

<400> SEQUENCE: 121
tgttcactgg tgaaggccag                                               20

<210> SEQ ID NO 122
<211> LENGTH: 19
<212> TYPE: DNA
<213> ORGANISM: Artificial Sequence
<220> FEATURE:
<223> OTHER INFORMATION: Tet3 LA-F

<400> SEQUENCE: 122
gaacagctcc tcgcccttg                                                19
```

<210> SEQ ID NO 123
<211> LENGTH: 20
<212> TYPE: DNA
<213> ORGANISM: Artificial Sequence
<220> FEATURE:
<223> OTHER INFORMATION: Tet3 LA-F

<400> SEQUENCE: 123
tgagcaaaga ccccaacgag					20

<210> SEQ ID NO 124
<211> LENGTH: 20
<212> TYPE: DNA
<213> ORGANISM: Artificial Sequence
<220> FEATURE:
<223> OTHER INFORMATION: Tet3 RA-R

<400> SEQUENCE: 124
atcgacaaac tttggggcga					20

<210> SEQ ID NO 125
<211> LENGTH: 60
<212> TYPE: DNA
<213> ORGANISM: Artificial Sequence
<220> FEATURE:
<223> OTHER INFORMATION: P2A-fluorescence F

<400> SEQUENCE: 125
gccacgaagc aagcaggaga tgttgaagaa aaccccgggc ctgtgagcaa gggcgaggag					60

<210> SEQ ID NO 126
<211> LENGTH: 19
<212> TYPE: DNA
<213> ORGANISM: Artificial Sequence
<220> FEATURE:
<223> OTHER INFORMATION: P2A-fluorescence R

<400> SEQUENCE: 126
cttgtacagc tcgtccatg					19

<210> SEQ ID NO 127
<211> LENGTH: 21
<212> TYPE: DNA
<213> ORGANISM: Artificial Sequence
<220> FEATURE:
<223> OTHER INFORMATION: Tet2 LA-F

<400> SEQUENCE: 127
cacacccttc accaacagac g					21

<210> SEQ ID NO 128
<211> LENGTH: 20
<212> TYPE: DNA
<213> ORGANISM: Artificial Sequence
<220> FEATURE:
<223> OTHER INFORMATION: Tet2 LA-R

<400> SEQUENCE: 128
atctcgaact cgtggccgtt					20

<210> SEQ ID NO 129
<211> LENGTH: 21
<212> TYPE: DNA
<213> ORGANISM: Artificial Sequence
<220> FEATURE:
<223> OTHER INFORMATION: Tet2 RA-F

<400> SEQUENCE: 129
aagaccacct acaaggccaa g                                               21

<210> SEQ ID NO 130
<211> LENGTH: 25
<212> TYPE: DNA
<213> ORGANISM: Artificial Sequence
<220> FEATURE:
<223> OTHER INFORMATION: Tet2 RA-R

<400> SEQUENCE: 130
ggtaggcaaa gtgcttttct aagac                                           25

<210> SEQ ID NO 131
<211> LENGTH: 20
<212> TYPE: DNA
<213> ORGANISM: Artificial Sequence
<220> FEATURE:
<223> OTHER INFORMATION: Lenti-sg-F

<400> SEQUENCE: 131
gttactcgag ccaaggtcgg                                                 20

<210> SEQ ID NO 132
<211> LENGTH: 20
<212> TYPE: DNA
<213> ORGANISM: Artificial Sequence
<220> FEATURE:
<223> OTHER INFORMATION: Lenti-sg-R

<400> SEQUENCE: 132
gactcggtgc cactttttca                                                 20

<210> SEQ ID NO 133
<211> LENGTH: 20
<212> TYPE: DNA
<213> ORGANISM: Artificial Sequence
<220> FEATURE:
<223> OTHER INFORMATION: Polm check-F

<400> SEQUENCE: 133
tccgatggga agccaaaagc                                                 20

<210> SEQ ID NO 134
<211> LENGTH: 20
<212> TYPE: DNA
<213> ORGANISM: Artificial Sequence
<220> FEATURE:
<223> OTHER INFORMATION: Polm check-R

<400> SEQUENCE: 134
cgtaccgcaa ccgcgaagta                                                 20

<210> SEQ ID NO 135
<211> LENGTH: 20
<212> TYPE: DNA
<213> ORGANISM: Artificial Sequence
<220> FEATURE:
<223> OTHER INFORMATION: Scube1 check-F

<400> SEQUENCE: 135
ccataataat ccacttccat                                                 20

<210> SEQ ID NO 136

```
<211> LENGTH: 20
<212> TYPE: DNA
<213> ORGANISM: Artificial Sequence
<220> FEATURE:
<223> OTHER INFORMATION: Scubelcheck-R

<400> SEQUENCE: 136
ccaacccctg tccactacct                                              20
```

ANDROGENETIC HAPLOID EMBRYONIC STEM CELL (AG-HAESC), AND PREPARATION METHOD AND USE THEREOF

BACKGROUND OF THE PRESENT INVENTION

Field of Invention

The present invention relates to biotechnologies, and specifically to an androgenetic haploid embryonic stem cell (AG-haESC), and a preparation method and use thereof.

Description of Related Arts

Genome-wide recessive genetic screening is an extremely effective and powerful method of identifying the functions of a gene involved in a given biological process. This strategy has been successfully used in lower organisms such as Saccharomyces cerevisiae and nematodes. In mammals, this functional screening is exceptionally difficult due to the diploidy of the genome (Shi, L., Yang, H., and Li, J. (2012). Haploid embryonic stem cells: an ideal tool for mammalian genetic analyses. Protein & cell 3, 806-810). The means of targeting RNA interference (RNAi) at mRNA level has now become an optimal solution for genome-wide loss-of-function genetic screening in mammalian cells. However, this method often cannot effectively inhibit the gene expression, while there is an off-target effect (Kaelin, W. G., Jr. (2012). Molecular biology. Use and abuse of RNAi to study mammalian gene function. Science 337, 421-422). Recently, the bacterial-derived CRISPR-Cas9 system has been successfully used in the screening of genetic defects of the mouse and human at cellular levels. However, CRISPR-Cas9-mediated genome-wide screening is only used at cellular level, which limits the study exclusively to phenotyping at cellular level. In this regard, as currently done with lower organisms such as yeast and nematodes, it is important to achieve efficient, large-scale loss-of-function screening of a broader range of biological processes in mammalian systems.

The obtaining of mammalian haploid embryonic stem cells (haESCs) (Elling, U., Taubenschmid, J., Wirnsberger, G., O'Malley, R., Demers, S. P., Vanhaelen, Q., Shukalyuk, A. I., Schmauss, G., Schramek, D., Schnuetgen, F., et al. (2011). Forward and reverse genetics through derivation of haploid mouse embryonic stem cells. Cell Stem Cell 9, 563-574; and Leeb, M., and Wutz, A. (2011). Derivation of haploid embryonic stem cells from mouse embryos. Nature 479, 131-134) provides a desirable tool for genetic analysis. The androgenetic haploid embryonic stem cells (AG-haESCs) have a whole genome derived from spermatid, with which the full development of a reconstructed embryo can be achieved by intracytoplasmic AG-haESCs injection (ICAHCI) into mature MII oocytes, thereby obtaining a viable animal subject that is referred to as semi-cloned animal. It is inferred that if semi-cloned mice can be produced with AG-haESCs efficiently and stably by ICAHCI, important genes involved in a particular developmental process can be screened out by using AG-haESCs as fertilizing vectors to carry genome-wide CRISPR-Cas9 knockout library.

However, previous studies have shown that the birth rate of viable, semi-cloned mice is very low (where the birth rate is 4.5% for half-cloned mice and 1% for semi-cloned rats), while approximately 50% of the semi-cloned mice exhibit a phenotype of retarded developmental, and are died shortly after birth. Furthermore, with the long-term culture of AG-haESCs, the overall birth rate of semi-cloned mice declines rapidly, especially for the additional culture resulting from genetic manipulation.

One of the possible reasons is the abnormal expression of imprinted genes. These imprinted genes that are expressed in a parent-of-origin-specific manner are considered as an important barrier to the development of uniparental embryos, so that the normal growth and development of embryos require both the maternal and paternal genomes. At present, about 150 imprinted genes have been identified in mice, most of which are located in a large cluster of genes and are regulated by differentially methylated regions (DMRs) (Bartolomei, M. S. (2009). Genomic imprinting: employing and avoiding epigenetic processes. Genes & development 23, 2124-2133). Consistent with this hypothesis, studies have shown that the imprinting of differentially methylated region (DMR) in which the imprinted gene H19 with inhibited paternal expression located is consistently abnormally erased in both AG-haESCs and growth-arrested, semi-cloned mice (Yang, H., Shi, L., Wang, B. A., Liang, D., Zhong, C., Liu, W., Nie, Y., Liu, J., Zhao, J., Gao, X., et al. (2012). Generation of genetically modified mice by oocyte injection of androgenetic haploid embryonic stem cells. Cell 149, 605-617). The maternally expressed H19 gene is adjacent to the paternally expressed Igf2, and both of them are regulated by the same DMR. This DMR is amenable to DNA methylation in the paternal allele, and as a CTCF-dependent insulator, permits the expression of the maternal allele only. The methylation state of this DMR determines whether H19 (where H19 is expressed, DMR is demethylated, and the insulator is activated) or Igf2 (where Igf2 is expressed, DMR is methylated, and the insulator is deactivated) is expressed. Interestingly, knockout of the H19 gene or its DMR does not lead to any severe phenotype in mice (Leighton, P. A., Ingram, R. S., Eggenschwiler, J., Efstratiadis, A., and Tilghman, S. M. (1995). Disruption of imprinting caused by deletion of the H19 gene region in mice. Nature 375, 34-39; and Thorvaldsen, J. L., Mann, M. R., Nwoko, O., Duran, K. L., and Bartolomei, M. S. (2002). Analysis of sequence upstream of the endogenous H19 gene reveals elements both essential and dispensable for imprinting. Molecular and cellular biology 22, 2450-2462). At present, there are related researches on reconstructed embryos obtained by using fully mature oocytes and genetically modified immature oocytes (Kono, T., Obata, Y., Wu, Q., Niwa, K., Ono, Y., Yamamoto, Y., Park, E. S., Seo, J. S., and Ogawa, H. (2004). Birth of parthenogenetic mice that can develop to adulthood. Nature 428, 860-864; and Kawahara, M., Wu, Q., Takahashi, N., Morita, S., Yamada, K., Ito, M., Ferguson-Smith, A C., and Kono, T. (2007). High-frequency generation of viable mice from engineered bi-maternal embryos. Nature biotechnology 25, 1045-1050). However, the immature oocytes cannot be cultured and expanded in vitro, so the in-vitro genetic modification cannot be realized; and the technique of obtaining reconstructed embryos from fully-matured oocytes and genetically modified immature oocytes is difficult in operation, so the application value is not high.

SUMMARY OF THE PRESENT INVENTION

In view of the disadvantage of low birth rate of semi-cloned animals in the prior art, an object of the present invention is to provide an androgenetic haploid embryonic stem cell (AG-haESC) that can enhance the birth rate of semi-cloned animals and use thereof.

The most possible cause of low birth rate is the occurrence of abnormal imprinting status of the androgenetic haploid. It is surprisingly found through experiments that characteristics of the AG-haESCs resembling those of a round spermatid can be established by knocking out the differentially methylated regions (DMRs) of two imprinted clusters H19-Igf2 and Dlk1-Dio3. Such AG-haESCs with two DMRs knocked out is designated as DKO-AG-haESCs. With the DKO-AG-haESCs, semi-cloned mice can be obtained effectively (with a birth rate of SC mice of about 20%), and semi-cloned animals with multiple genetic modifications can still be produced stably after in-vitro genetic manipulation of the AG-haESCs. Unexpectedly, a large number of mutant animals can be effectively obtained in one step simply by transfecting the DKO-AG-haESCs with stable expression of sgRNA library and Cas9 in vitro at the cellular level. These experimental results show that DKO-AG-haESCs can be used as an intermediate to achieve gene mutation at the individual level by carrying the sgRNA library and therefore can be further used in gene mutation-based large-scale screening at individual animal level.

A first aspect of the present invention provides an AG-haESC, in which H19 DMR and IG-DMR genes are knocked out.

A second aspect of the present invention provides a method for preparing the AG-haESC, which comprises knocking out H19 DMR and IG-DMR from an AG-haESC, to obtain the above mentioned AG-haESC.

A third aspect of the present invention provides use of the AG-haESC in constructing a genetically modified semi-cloned animal.

A fourth aspect of the present invention provides a method for constructing a genetically modified semi-cloned animal, which comprises combining an AG-haESC in which H19 DMR and IG-DMR genes are both knocked out with an oocyte to obtain a semi-cloned embryo, and incubating the semi-cloned embryo, to obtain a semi-cloned animal.

A fifth aspect of the present invention provides a genetically modified animal, which is constructed according to the above method, or is a sexually reproduced offspring of a semi-cloned animal constructed according to the above method.

A sixth aspect of the present invention provides a method for constructing a genetically modified semi-cloned animal library with the AG-haESCs according to the present invention and a lentiviral sgRNA library.

A seventh aspect of the present invention provides a genetically modified semi-cloned animal library constructed by using the above method.

The present invention has the following beneficial effects.

(1) Existing studies show that semi-cloned animals can be obtained from AG-haESCs established with haploid blastocyst by ICAHCI. However, AG-haESCs cannot produce viable SC animals after long-term subculture, especially after in vitro genetic manipulation, probably due to the loss of male imprinted genes. It is found in the present invention that the AG-haESCs is capable of obtaining characteristics resembling a round spermatid by knocking out H19 and IG-DMR. Upon injection into an oocyte, a viable SC mouse is stably obtained with AG-haESCs at a rate of about 20%, which is about 10 times of the rate obtained with earlier generation of WT AG-haESCs (Yang et al., 2012). Importantly, it is also found in the present invention that DKO-AG-haESCs can be effectively used for multi-gene genetic manipulation, and SC mice with multiple genetic modifications can be further obtained by ICAHCI. More importantly, by incorporating with a sgRNA library, DKO-AG-haESCs can be effectively used in one-step generation of heterozygous and homozygous mutant mice, providing further evidence for gene knockout-based screening at animal individual level.

(2) DKO-AG-haESCs are advantageous over the existing methods for obtaining genetically modified animals in the following aspects. Firstly, existing studies report the one-step production of transgenic mice or mice with endogenous genetic mutations by direct injection of Cas9 mRNA and sgRNA into fertilized eggs. This method demonstrates the strong potential of CRISPR-Cas9 technique in the production of genetically modified animals. However, there is an extremely high rate of chimerism observed in the genetically manipulated animals so far, which greatly increases the difficulty of phenotyping in F1 generation of animals. In contrast, DKO-AG-haESCs-mediated gene editing technology provides a unique set of system for well phenotyping and screening genetically modified DKO-AG-haESCs, to ensure that the resulting SC animals exhibit the expected genetic traits, so the occurrence of chimerism can be largely avoided. Secondly, genetically modified mice obtained by conventionally injecting diploid embryonic stem cells into the blastocysts need to experience the germline transmission of chimeric mice. However, the step of germline transmission is often very time-consuming. More seriously, the diploid embryonic stem cells with multiple genetic modifications may exhibit trait segregation in their offspring during germline transmission. Only a small percentage of offspring may contain all the desired genetic modifications. In contrast, F0 mice with multiple genetic modifications can be obtained with DKO-AG-haESCs in one step. Thirdly, fully ESC-derived mice can be obtained in one step by injecting diploid embryonic stem cells into the tetraploid blastocysts (also known as tetraploid complementation technique). This method is also widely used and is the most stringent standard for testing the pluripotency of reprogrammed cells such as induced pluripotent stem cells (iPSCs) and nuclear transfer embryonic stem cells (ntESCs). However, the birth rate of the embryonic stem cell (ESC)- or iPSC-derived animals is very low, probably due to the epigenetic instability of diploid embryonic stem cells. In contrast, animals can still be stably and efficiently obtained with DKO-AG-haESCs after long-term in vitro culture, especially genetic manipulation. Fourthly, the ICAHCI technology is similar to ROSI that is a sophisticated technology for various mammals, including non-human primates and human. Cynomolgus monkey-derived haploid embryonic stem cell line has now been successfully established and the ICAHCI technology may be used in the near future to efficiently and rapidly obtain genetically modified non-human primates. Lastly, a large number of genetically mutated animals can be obtained with DKO-AG-haESCs by incorporating with a sgRNA library. Obviously, this method is simpler and less labor-intensive than direct injection of plasmids or mRNAs into embryos for the large-scale production of mutant animals, since the DKO-AG-haESC line, which carries constantly expressed Cas9 and sgRNA library, can repeatedly serve as a donor for injection, to produce various genetically mutated animals continuously and effectively. These various mutant animals can be easily and quickly identified for the sgRNA insertion (which is exactly a barcode for a mutant animal) by PCR using a universal pair of primers. In contrast, the method of injecting plasmids or mRNAs directly into embryos requires separate preparation of sgRNAs for each individual injection. The mutant animals obtained need to be housed separately, and the subsequent identification requires the use of corresponding primers for a particular gene. It is conceivable that some of the differentially expressed genes obtained from an appropriate sgRNA library, such as those obtained by high-throughput analysis at the cellular level, can be classified into a sub-library of sgRNAs that may be involved in a particular stage of development. By using the DKO-AG-haESC solution, important genes related to this development process can be rapidly and effectively screened out at the individual level.

(3) Production of DKO-AG-haESC-mediated SC animals is an effective and simple way to generate animal models that carry genetic modifications such as multiple genetic mutations or multiple gene knockins in a gene family. Moreover, by incorporating with a sgRNA library, a large number of genetically mutated animals can be obtained in one step with DKO-AG-haESCs. Although the underlying mechanism that DKO-AG-haESCs is so effective in the production of SC animals is still unknown, this approach may be able to facilitate the deeper exploration for the developmental process and complex diseases.

BRIEF DESCRIPTION OF THE DRAWINGS

FIG. 1G shows production of $H19^{\Delta DMR}$-$IG^{\Delta DMR}$-AGH-1 cell line. Left panel: collected mCherry positive cells plated in a Petri dish. Right panel: established $H19^{\Delta DMR}$-$IG^{\Delta DMR}$-AGH cell line ($H19^{\Delta DMR}$-$IG^{\Delta DMR}$-AGH-4).

FIG. 1H shows SC mice produced with $H19^{\Delta DMR}$-$IG^{\Delta DMR}$-AGU-4 (p29) by ICAHCI.

FIG. 1I shows genotyping of $H19^{\Delta DMR}$-AGH cell line.

FIG. 1J shows that 80% of the embryos reconstructed with $H19^{\Delta DMR}$-AGH cells reach 2-cell embryos, which is similar to the developmental rate obtained upon round spermatid injection (ROSI).

FIG. 1K shows SC mice produced with $H19^{\Delta DMR}$-AGH-1, 2, 3 cell lines by ICAHCI, in which asterisk represents growth-arrested SC mice.

FIG. 2I shows genotyping of $H19^{\Delta DMR}$-$IG^{\Delta DMR}$-AGH cell line obtained by knocking out IG-DMR from $H19^{\Delta DMR}$-AGH cells.

FIG. 2J shows the sequencing result of a DKO-AG-haESC cell line ($H19^{\Delta DMR}$-$IG^{\Delta DMR}$-AGH-4, SEQ ID NO. 17).

FIG. 2K shows 2-cell embryos obtained with $H19^{\Delta DMR}$-$IG^{\Delta DMR}$-AGR cells by ICAHCI.

FIG. 2L shows genotyping of SC mice, where $H19^{\Delta DMR}$-$IG^{\Delta DMR}$-AGH-4-derived SC mice all have H19 and IG DMR knockouts.

FIG. 2M shows SC mice produced with $IG^{\Delta DMR}$-AGH-2 (p8).

FIG. 2N shows the methylation state of H19 DMR in $IG^{\Delta DMR}$-AGH cells.

FIG. 2O shows the methylation state of H19 DM in $IG^{\Delta DMR}$-AGH-2-derived normal and growth-arrested SC mice.

FIG. 2P shows sequencing of a DKO-AG-haESC cell line ($IG^{\Delta DMR}$-$H19^{\Delta DMR}$-AGH-2 SEQ ID NO. 18).

FIG. 2Q shows SC mice produced with $IG^{\Delta DMR}$-$H19^{\Delta DMR}$-AGH-2 cells (p24) by ICAHCI.

FIG. 2R shows genotyping of $IG^{\Delta DMR}$-$H19^{\Delta DMR}$-AGR-2-derived SC mice.

FIG. 3A is a view schematically showing Tet1, Tet2 and Tet3 sgRNAs (SEQ ID NO. 5-7).

FIG. 3G shows sequencing of p53, p63 and p73 in p53-TKO-DAH-2 cell line (P53 wild-type: SEQ ID NO. 25;

Gene mutation of P53 in P53-TKO-DAH-2: SEQ ID NO. 26; P63 wild-type: SEQ ID NO. 27; Gene mutation of P63 in P53-TKO-DAH-2: SEQ ID NO. 28; P73 wild-type: SEQ ID NO. 29; Gene mutation of P73 in P53-TKO-DAH-2: SEQ ID NO. 30). FIG. 3H is a view schematically showing Tet1-EGFP, Tet2-mCherry, and Tet1 ECFP double-stranded DNA vectors, in which EGFP, mCherry, and ECFP are respectively fused to a stop codon of Tet1, Tet2, and Tet3.

FIG. 3I shows genotyping of Tet-TKO-DAH-1 cell line.

FIG. 3K shows SC mice produced with $H19^{\Delta DMR}$-$IG^{\Delta DMR}$-AGU-OG3-1 (p26) by ICAHCI.

FIG. 4A is a view schematically showing a large number of heterozygous mutant SC mice produced with DKO-AG-haESCs carrying sgRNA library by ICAHCI.

FIG. 4B represents mCherry-positive haploid cells successfully transfected with Cas9 enriched by FACS for subsequent ICAHCI.

FIG. 4C shows PCR identification of sgRNAs in single cell derived haploid clones, where the tested cell clones all carry sgRNAs.

FIG. 4D shows sequencing of different mutant genes in cell clones, where the tested cell clones all have modifications of the genes of interest (Iqcf5 wild-type: SEQ ID NO. 35; Iqcf5 mutant gene: SEQ ID NO. 36; Olfr1247 wild-type: SEQ ID NO. 37; Olfr1247 mutant gene: SEQ ID NO. 38; Kbtbd2 wild-type: SEQ ID NO. 39; Kbtbd2 mutant gene: SEQ ID NO. 40; Hmox1 wild-type: SEQ ID NO. 41; Hmox1 mutant gene: SEQ ID NO. 42).

FIG. 4E shows SC mice derived from DKO-AG-haESCs carrying sgRNA library.

FIG. 4F shows PCR identification of sgRNAs in SC mice.

FIG. 4G shows sequencing of different mutant genes of interest in SC mice, where all the tested SC mice have modifications of the genes of interest (Fibp wild-type: SEQ ID NO. 43; Fibp mutant gene: SEQ ID NO. 44; Csf2 wild-type: SEQ ID NO. 45; Csf2 mutant gene: SEQ ID NO. 46; Vav3 wild-type: SEQ ID NO. 47; Vav3 mutant gene: SEQ ID NO. 48; Lrrc61 wild-type: SEQ ID NO. 49; Lrrc61 mutant gene: SEQ ID NO. 50).

FIG. 4H shows sequencing of Tet1, Tet2 and Tet3 in Tet-TKO-DAH-3 cell line (Tet1 wild-type: SEQ ID NO. 51; Gene mutation of Tet1 in Tet-TKO-DAH-3: SEQ ID NO. 52; Tet2 wild-type: SEQ ID NO. 53; Gene mutation of Tet2 in Tet-TKO-DAH-3: SEQ ID NO. 54; Tet3 wild-type: SEQ ID NO. 55; Gene mutation of Tet3 in Tet-TKO-DAH-3: SEQ ID NO. 56).

FIG. 4I shows SC mice produced with Tet-TKO-DAH-3 (p36) by ICAHCI.

FIG. 4J shows sequencing of p53, p63 and p73 in p53-TKO-DAH-1 cell line (P53 wild-type: SEQ ID NO. 57; Gene mutation of P53 in P53-TKO-DAH-1: SEQ ID NO. 58; P63 wild-type: SEQ ID NO. 59; Gene mutation of P63 in P53-TKO-DAH-1: SEQ ID NO. 60; P73 wild-type: SEQ ID NO. 61; Gene mutation of P73 in P53-TKO-DAH-1: SEQ ID NO. 62).

FIG. 4K shows SC mice produced with p53-TKO-DAH-1 cell line (p44) by ICAHCI.

FIG. 4L shows sequencing of p53, p63 and p73 in SC mice produced with p53-TKO-DAH-1 and p53-TKO-DAH-2 cell line.

FIG. 5A is schematic representation of a large number of bi-allelic mutant SC mice produced by ICAHCI with DKO-AG-haESCs that carry consistently expressed Cas9 and sgRNA library.

FIG. 5B shows PCR analysis of Cas9 in single cell-derived cell clone, where all tested cell clones comprises the Cas9 transgene.

FIG. 5C shows quantitative PCR analysis of Cas9 in single cell-derived cell clones.

FIG. 5D shows PCR identification of sgRNAs in single cell-derived cell clones.

FIG. 5E shows SC mice derived from DKO-AG-haESCs that carry constantly expressed Cas9 and sgRNA library.

FIG. 5F shows PCR identification of sgRNAs in SC mice.

FIG. 5G shows bi-allelic mutant SC mice produced by ICAHCI with DKO-AG-haESCs that carry constantly expressed Cas9 and sgRNA Library, in which the Polm bi-allelic mutant SC mice are taken as an example.

FIG. 5H shows analysis of the polm gene mutation in the mouse tail by TA cloning and sequencing, where 24 out of 26 tested clones have a frameshift mutation (SEQ ID NO. 63-67).

FIG. 5I shows summary of TA cloning and sequencing results of 7 bi-allelic mutant SC mice, in which more than 80% of the clones have insertion or deletion mutations.

FIG. 5J shows TA cloning and sequencing of different organs in Scube1 bi-allelic mutant SC mice.

FIG. 5K is a view schematically showing Tet1-EGFP, Tet2-mCherry, and Tet3-ECFP exogenous double-stranded vectors.

FIG. 5L shows genotyping of Tet1-EGFP knock-in DKO-AG-haESCs.

FIG. 5M shows genotyping of Tet3-ECFP knock-in DKO-AG-haESCs.

FIG. 5N shows genotyping of Tet1&3-KI-DAH-1 cell line.

FIG. 5O shows sequencing of Tet1-EGFP and Tet-ECFP in Tet1&3-KI-DAH-1 cell line (SEQ ID NO. 68-69).

FIG. 5P shows 3-week-old SC mice produced with Tet1&3-KI-DAH-1 cell line (p40) by ICAHCI.

FIG. 5Q shows genotyping of SC mice produced with Tet1&3-KI-DAH-1 cell line.

FIG. 5R shows sequencing of Tet2-mCherry in Tet-TKI-DAH-1 cell line (SEQ ID NO. 70).

FIG. 5S shows SC mice produced with Tet-TKI-DAH-2 cell line (p50).

FIG. 5T shows genotyping of SC mice produced with Tet-TKI-DAH-1 cell line.

FIG. 6A shows bi-allelic mutant mice produced by injecting haploid cells transiently treansfected with pX330-mCheny plasmid and carrying sgRNAs into mature oocytes and then injecting Cas9 mRNA to the reconstructed oocytes (where the protocol is known as Lenti-sgRNA+pX330+ Cas9 injection).

Fig. 6B shows PCR identification of sgRNA insertion into single cell-derived haploid ES clones.

Fig. 6C shows SC mice produced with DKO-AG-haESCs carrying sgRNA library.

Fig. 6D shows PCR identification of sgRNAs in SC mice.

Fig. 6E shows bi-allelic mutant mice produced by injecting DKO-AG-haESCs carrying sgRNA library into oocytes, and then injecting Cas9 mRNA to SC embryos, in which bi-allelic mutant mice carrying Slco5al gene are taken as an example.

Fig. 6F shows TA cloning and sequencing of tails of mice carrying Slco5al gene, where 18 out of the 20 tested clones have insertion or deletion mutations (SEQ ID NO. 71-74).

DETAILED DESCRIPTION OF THE PREFERRED EMBODIMENTS

Figure 1A:
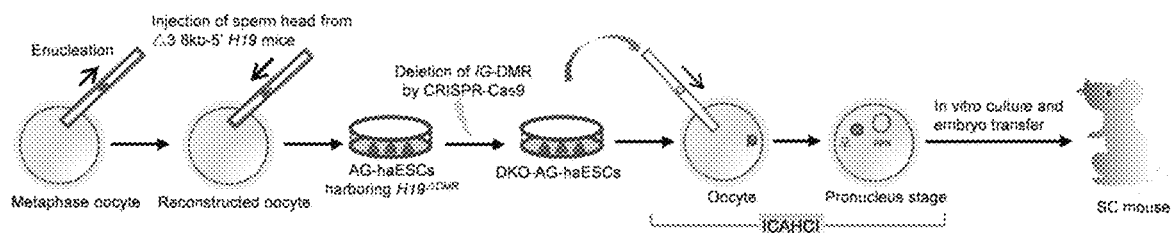
FIG. 1A is a view schematically showing the production of SC mice by intracytoplasmic AG-haESCs injection (ICAHCI) of AG-haESCs bearing 2 DMR knockouts.

The present invention provides an androgenetic haploid embryonic stem cell (AG-haESC), in which H19DMR and IG-DMR are knocked out.

The AG-haESCs have a whole genome derived from spermatid, has the self-replication ability and pluripotency of stem cells, and can replace the spermatid to combine with oocytes to support the full development of embryos.

H19 DMR refers to a differentially methylated region (DMR) within the H19-Igf2 imprinted cluster. The specific location and sequence of H19 DMR can be determined according to the existing methods such as methylation sequencing or homologous sequence analysis and prediction. Human H19DMR is known to be located in the 1p15.5 region of the chromosome 1 and the mouse H19 DMR is located at the distal end of chromosome 7 between the two genes H19 and Igf2, a position from 2 kb to 4 kb upstream of the H19 gene. H19 DMR is methylated on the paternal allele, resulting in the inability of CTCF protein to bind to this methylated region so that the enhancer downstream of H19 does not need to cross over the obstacle CTCF, thereby increasing the expression of upstream Igf2 and decreasing the H19 expression. H19 DMR is demethylated on the maternal allele, and the CTCF protein is able to bind to this unmethylated region, so the enhancer downstream of H19 can only increase the H19 expression, and cannot regulate the upstream Igf2. If the paternal H19 DMR is knocked out, the enhancer downstream of H19 can upregulate the expression of Igf2. Since the androgenetic haploid is of paternal origin, theoretically it should be in a completely methylated state. However, studies show that the H19 DMR in the androgenetic haploid cultured in vitro suffers from abnormally erased methylation, and becomes demethylated, so that the expression of H19 is abnormally up-regulated and the expression of Igf2 is down-regulated. In the present invention, H19 DMR is knocked out and the abnormal state in which H19 expression is up-regulated and the Igf2 expression is down-regulated is corrected.

IG-DMR refers to a differentially methylated region (DMR) within the Dlk-Dio3 imprinted cluster. The specific location and sequence of IG DMR can be determined according to the existing methods such as methylation sequencing or homologous sequence analysis and prediction. The mouse IG-DMR is known to be located on the chromosome 12 in a 4.15 kb repeat between the genes Dlk1 and Gtl2 in the imprinted cluster, and the human IG-DMR is located on the chromosome 14 (14q32.2). IG-DMR is DNA methylated on the paternal allele, so the gene Gtl2 and some micromRNAs in this imprinted cluster are not expressed while the gene Rtl1, Dlk1 and Dio3 are expressed. IG-DMR is un-DNA methylated (in demethylated state) on the maternal allele, so Gtl2 and some micromRNAs are expressed while the gene Rtl1, Dlk1 and Dio3 are not expressed. In the androgenetic haploid (of paternal origin) and SC animals born abnormal, studies show that the normally methylated IG-DMR suffers from abnormally erased methylation, causing the silencing of the genes Rtl1, Dlk1, and Dio3, and the abnormal activation of Gtl2 and some microRNAs.

Further, the AG-haESCs undergo other genetic modifications in addition to H19 DMR and IG-DMR knockouts.

Specifically, genetic modification refers to the structural change of a gene made by a biological, chemical or physical means compared with that before modification, and this change mainly refers to the change in base pair composition, comprising, but not limited to, changes caused by the replacement, insertion, and deletion of one or more base pairs.

In a preferred embodiment, the genetic modifications of Tet1, Tet2, Tet3 and p53 family of genes are exemplified.

The AG-haESCs are derived from mammals, comprising human or non-human mammals. Preferably, the AG-haESCs are derived from a rodent, such as rabbit and murine that may be a mouse or a rat. In a preferred embodiment, the AG-haESCs are derived from mice.

Compared with AG-haESCs in which H19 DMR and IG-DMR are not both knocked out, the birth rate of semi-cloned animals constructed with the AG-haESCs of the present invention is higher.

The present invention also provides a method for preparing the AG-haESCs, which comprises knocking out the H19 DMR and IG-DMR from AG-haESCs, to obtain the AG-haESCs.

The H19 DMR and IG-DMR can be knocked out by using an existing gene editing method. In a preferred embodiment, the H19 DMR and IG-DMR are knocked out using CRISPR/Cas9-mediated gene manipulation. Gene knockouts may also be performed by other methods, and the present invention is not limited to the methods listed in the examples.

Due to the H19 DMR knockout, the complete sequence of H19 DMR is removed from the chromosome DNA; and due to the IG DMR knockout, the complete sequence of IG-DMR is removed from the chromosome DNA.

In an embodiment, H19 DMR knockout AG-haESCs are constructed firstly, and then IG-DMR is further knocked out. In another embodiment, IG-DMR knockout AG-haESCs are constructed firstly and then H19 DMR is further knocked out. In another example, AG-haESCs in which H19 DMR and IG-DMR are both knocked out are directly constructed.

Further, the AG-haESCs also undergo other genetic modifications.

Such other genetic modifications refer to genetic modifications other than H19 DMR and IG-DMR knockouts. Such other genetic modifications may be the modification of a single target gene or the modifications of multiple target genes of interest. The target gene of interest is not specific and can be set and modified as desired in the research. For example, such other genetic modifications may be the modifications of one, two or more target genes. The AG-haESCs of the present invention in which H19 DMR and IG-DMR are both knocked out can be passaged in vitro, and thus they can theoretically be genetically modified constantly. The number of modifications made to the target gene can be set as needed without particular limitation.

The genetic modifications comprise, but are not limited to, knock-in and knock-out of a target gene, and the like. The knock-in and knock-out of a target gene may be accomplished by techniques such as gene targeting and homologous recombination, comprising, but not limited to, genetic manipulation based on ZFN (zinc finger nuclease), TALEN (transcriptional activator-like effector nuclease) and CRISPR/Cas9 (clustered regularly interspaced short palindromic repeats).

In an embodiment, the AG-haESCs in which the H19 DMR and IG-DMR are both knocked out undergo one or more genetic modifications to obtain the AG-haESCs with H19 DMR and IG-DMR knockouts and with other genetic modifications. Alternatively, AG-haESCs can be genetically modified first, followed by knocking out H19DMR and IG-DMR from the genetically mutated AG-haESCs. In addition to the above, other biotechnological means that can achieve the H19 DMR and IG-DMR knockouts and other genetic mutations can also be used to construct the AG-haESCs with H19 DMR and IG-DMR knockouts and with other genetic modifications.

The present invention also provides the use of the AG-haESCs in constructing genetically modified semi-cloned animals. Further, the AG-haESCs are used as a fertilizing vector in place of spermatid in the construction of genetically modified animals.

The present invention also provides a method for constructing a genetically modified semi-cloned animal, which comprises: combining an AG-haESC in which H19 DMR and IG-DMR are both knocked out with an oocyte to obtain a semi-cloned embryo, and incubating the semi-cloned embryo to obtain a semi-clone animal.

In general, the oocytes and the AG-haESCs are derived from the same kind of animal, preferably the same species of animal.

The semi-cloned embryo may specifically be an semi-cloned embryo obtained by ICAHCI using the AG-haESCs in which H19 DMR and IG-DMR are both knocked out as a donor for ICAHCI.

Further, the semi-cloned animal can be obtained by incubating the semi-cloned embryo in a suitable female organism by embryo transfer. In a preferred embodiment, the suitable maternal is a pseudopregnant ICR female rat.

Further, the AG-haESCs undergoes other genetic modifications.

The present invention further provides a genetically modified animal, which is constructed according to the above method, or is a sexually reproduced offspring of a semi-cloned animal constructed according to the above method.

The semi-cloned animal according to the present invention may be a non-human mammal. Preferably, the semi-cloned animal is a rodent, such as rabbit or murine. In a preferred embodiment, the semi-cloned animal is a mouse.

The present invention also provides a method for constructing a genetically modified semi-cloned animal library, which comprises the steps of:
1) infecting the AG-haESCs according to the present invention with virus particles prepared with the lentiviral sgRNA library plasmids, to obtain an AG-haESC library carrying the sgRNA library;
2) obtaining a semi-cloned embryo library by ICAHCI using a vector expressing Cas9 and/or Cas9 mRNA, with AG-haESCs in the AG-haESC library carrying the sgRNA library as a donor for ICAHCI; and 3) incubating the embryos in the semi-cloned embryo library to obtain a semi-cloned animal library.

The sgRNA lentiviral library plasmids comprise several lentiviral vectors that express different sgRNAs. The lentiviral sgRNA library can be constructed by current technologies, or existing lentiviral sgRNA library plasmids may be used. Specifically, sgRNAs designed for different genes can be cloned into lentiviral vectors. The sgRNA can be designed according to the gene of interest.

In a preferred embodiment, a commercially available lentiviral sgRNA library of whole genomes of mice is employed.

Specifically, Step 2) may be selected from any one of:

Method A:
The AG-haESC library carrying the sgRNA library is further transfected with a plasmid expressing Cas9, and the semi-cloned embryos are obtained by ICAHCI using the resultant AG-haESCs as a donor for ICAHCI.

Method B:
AG-haESCs in the AG-haESC library carrying the sgRNA library, as a donor for ICAHCI, are injected into mature oocytes by ICAHCI, and then Cas9 mRNA is injected into the reconstructed oocytes, to obtain the semi-cloned embryos.

Method C:
The AG-haESC library carrying the sgRNA library is further transfected with a plasmid expressing Cas9, the resultant AG-haESCs, as a donor for ICAHCI, are injected into mature oocytes by ICAHCI, and then Cas9 mRNA is injected into the reconstructed oocytes, to obtain the semi-cloned embryo, from which a semi-cloned animal is obtained after embryo transfer.

In the methods A and C, the plasmid expressing Cas9 can be constructed by cloning the Cas9 expressing gene into an expression plasmid. In a preferred embodiment, the plasmid expressing Cas9 is pX330-mCherry plasmid. The plasmid that is constructed to express Cas9 is not limited to the pX330 plasmid. The expression plasmid only needs to be suitable for expression of exogenous genes in mammalian cells.

The present invention further provides another method for constructing a genetically modified semi-cloned animal library, which comprises the steps of:
1) infecting the AG-haESCs according to the present invention with lentiviral particles expressing Cas9 and lentiviral particles prepared with the lentiviral sgRNA library, to obtain an AG-haESC library with constant expression of the sgRNA library and Cas9;
2) obtaining a semi-cloned embryo library by ICAHCI with AG-haESCs in the AG-haESC library with constant expression of the sgRNA library and Cas9 as a donor for ICAHCI; and
3) incubating the embryos in the semi-cloned embryo library to obtain a semi-cloned animal library.

The virus particles expressing Cas9 can be obtained by cloning the encoding gene expressing Cas9 into a lentiviral vector and then packaging the lentivirus in the prior art. The lentiviral vector expressing Cas9 is commercially available.

The semi-cloned animal library comprises several genetically mutated semi-cloned animals. The animals may be heterozygous or biallelic mutant animals.

Further, semi-cloned animals can be obtained by culturing the semi-cloned embryos in a suitable female organism by embryo transfer. In a preferred embodiment, the suitable female organism may be a pseudopregnant ICR female rat.

The present invention also provides a genetically modified semi-cloned animal library, which is constructed according to the method as described above.

The genetically modified semi-cloned animal library of the present invention can be used in genetic screening of genes at subordinate individual level.

The semi-cloned animal library of the present invention may be a non-human mammalian library. Preferably, the semi-cloned animal library is a rodent library, such as a rabbit library, and a murine library. In a preferred embodiment, the semi-cloned animal library is a mouse library.

The embodiments of the present invention are described below with reference to specific examples, and other advantages and effects of the present invention can be easily understood by those skilled in the art from the disclosure of the present invention. The present invention can also be implemented or practiced through additional different specific embodiments. The details in this specification may also be based on different perspectives and applications, and various modifications or changes can be made without departing from the spirit of the present invention.

When a numerical range is given in an example, it is to be understood that both endpoints of each numerical range and any numerical value between the two endpoints are encompassed, unless the context otherwise indicates. Unless defined otherwise, all technical and scientific terms as used herein have the same meanings as those commonly understood by those skilled in the art. In addition to the specific methods, equipment and materials used in the examples, the present invention may be implemented using any of the methods, devices, and materials in the prior art that are similar or equivalent to the methods, devices, and materials described in the examples of the present invention, based on the knowledge of those skilled in the art the prior art and the disclosure of the present invention, Unless otherwise specified, in the experimental methods, detection methods, and preparation methods disclosed in the present invention, the conventional molecular biology, biochemistry, chromatin structure and analysis, analytical chemistry, cell culture, recombinant DNA technology and conventional techniques in related fields are adopted. These techniques are well documented in the literature.

Abbreviations

AG-haESCs: androgenetic haploid embryonic stem cells
DKO-AG-haESCs: H19 DMR and IG-DMR double knockout androgenetic haploid embryonic stem cell 1. Experimental Materials and Methods 1.1. Materials and Reagents The cell culture medium (DMEM), fetal bovine serum (FBS), serum replacement (KSR), trypsin, Opti-MEM, DPBS, and Lipofectamine 2000 were purchased from Life Technologies Inc.; the restriction endonucleases and T4 ligase were purchased from NEB; the Taq enzyme and dNTPs were purchased from TaKaRa; the CDNA reverse transcription kit, and fluorescent quantification reagent SYBR-Green were purchased from TOYOBO; and the oligonucleotides were synthesized by Shanghai Generay Company.

HEPES-CZB Culture Medium

H-CZB Stock 98.5 ml, Hepes.2Na (sigma, CAT #H0763) or ICN 520 mg or Hepes (sigma, CAT #H4034) 476 mg, NHCO$_3$ 42 mg, CaCl$_2$.2H$_2$O 100× stock 1 ml, Pyruvate 3.0 mg, and Glutamin 200× stock 0.5 ml, adjusted to pH 7.4, and filtered well.

H-CZB Stock:

CZB stock 500 ml, PVA (sigma, P8136) 50 mg, CZB stock: H$_2$O 985 ml, NaCl (sigma, CAT #55886) 4760 mg, KCL (sigma, CAT #P5405) 360 mg, MgSO$_4$.7H$_2$O (sigma, CAT #M1880) 290 mg, EDTA-2Na (sigma, CAT #E6635) 40 mg, Na-Lactate (sigma, CAT #L7900) 5.3 ml, D-Glucose (sigma, CAT #G6152) 1000 mg, and KH$_2$PO$_4$ (sigma, CAT #P5655) 160 mg Activation solution: 10 mM Sr2+, 5 ng/ml Trichostatin A (TSA)

KSOM culture medium (KSOM+AA with glucose): millipore, CAT #MR-106-D

ESC medium:

DMEM (millipore, CAT #SLM-220-M) 75%, 20% serum replacement KSR (Gibco, CAT #10828-028), 1,500 U/ml LIF (Millopre, CAT #ESG1107), 3M CHIR99021 (Stemgent, CAT #04-0004), and 1M PD0325901 (Stemgent, CAT #04-0006)

Acid Tyrode solution: sigma, CAT #T1788
CZB culture medium:

CZB stock 99ML, CaCl$_2$.2H$_2$O 100× stock 1 ml, Pyruvate 3.0 mg, Glutamin 200× stock 0.5 ml, BSA 500 mg pX330-mCherry:

enzymatically cleaving px330 (addgene) plasmid with NotI, and then inserting a CMV-mcherry-pA fragment amplified from pmCherry-C1 (Clontech) into the enzymatically cleaved px330 plasmid.

```
Primers for amplification:
mCherry-F:
                                  (SEQ ID NO. 75)
ATTTGCGGCCGCATAGTAATCAATTACGGG mCherry-R:
                                  (SEQ ID NO. 76)
ATTTGCGGCCGCATGCAGTGAAAAAAATGC
```

Lentiviral sgRNA library of mice: supplied by Addgene viral plasmid expressing Cas9: supplied by Addgene Cas9 mRNA:
obtained as described in Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas-mediated genome engineering. Cell 153, 910-918.

Round Spermatid:

The mouse testis was digested with collagenase IV for 20 minutes and then with trypsin for 10 minutes, and then sorted by FACS, to obtain round spermatid of mice.

1.2. Test Animals

All animals were used in accordance with the procedures in the animal operation manual of Institute of Biochemistry and Cells, Shanghai Institutes for Biological Sciences, Chinese Academy of Sciences.

H19 Δ3.8 kb KO mice (C57/B6 background, homozygous): constructed as described in (Thorvaldsen, J. L., Mann, M R., Nwoko, O., Duran, K. L., and Bartolomei, M. S. (2002). Analysis of sequence upstream of the endogenous H19 gene reveals elements both essential and dispensable for imprinting. Molecular and cellular biology 22, 2450-2462.)

IG-DMRKO mice (C57/B6 background, heterozygous): constructed as described in (Lin, S. P., Youngson, N., Takada, S., Seitz, H., Reik, W., Paulsen, M., Cavaille, J., and Ferguson-Smith, A C. (2003). Asymmetric regulation of imprinting on the maternal and paternal chromosomes at the Dlk1-Gt12 imprinted cluster on mouse chromosome 12. Nature genetics 35, 97-102,)

B6D2F1 (C57BL/6×DBA2) female mice: female offspring obtained after mating with female mice of C57BL/6 strain with male mice of DBA2 strain.

Pseudopregnant ICR female mice: ICR adult female mice purchased from SLAC Laboratory Animal Co., Ltd were mated with ligated adult ICR male mice, to obtain pseudopregnant ICR female rats.

1.3. Establishment of AG-haESC Line

The AG-haESC line was constructed according a reported method (Yang, H., Shi, L., Wang, B. A., Liang, D., Zhong, C., Liu, W., Nie, Y., Liu, J., Zhao, J., Gao, X., et al. (2012). Generation of genetically modified mice by oocyte injection of androgenetic haploid embryonic stem cells. Cell 149, 605-617).

Method:

The MII oocytes were enucleated, into which the corresponding sperm heads were injected. Mouse MII oocytes were harvested 14 hours after treatment with human chorionic gonadotropin (HCG) and then enucleated using a Piezo needle in HEPES-CZB medium containing 5 µg/ml cytochalasin B (CB). After enucleation, single sperm heads were injected into the cytoplasm of the oocytes. The reconstructed embryos were cultured in CZB medium for 1 hour and then transferred to the activation solution containing 1 mM $Sr^{2+}$ for activation. After activation, all reconstructed embryos were transferred to KSOM medium containing amino acids and incubated at 37° C., and 5% $CO_2$. The reconstructed embryos reaching the morula or blastula stage 3.5 days later were seeded in ESC medium.

The zona pellucid of the reconstructed embryos was removed by digestion with the acid Tyrode solution. Each embryo was transferred to a 96-well plate plated with a mouse fibroblast feeder layer and cultured with ESC medium containing 20% serum replacement (KSR), 1,500 U/ml LIF, 3M CHIR99021 and 1 M PD0325901. After 4-5 days of culture, the cell clones were trypsinized and transferred to a 96-well plate plated with a fresh feeder layer. The cells were further expanded, and passaged into a 48-well plate and further into a 6-well plate, and the cells were daily maintained in a 6-well plate. To sort the haploid cells, after the embryonic stem cells were trypsinized, they were washed once with PBS (GIBCO) and then in ESC medium containing 15 µg/ml Hoechst 33342. After being placed in a water bath for 30 min, haploid cells of 1N peak were sorted by the flow cytometer BD FACS AriaII and subsequently subcultured to obtain the AG-haESC line.

1.4 CRISPR-Cas9-Mediated Genetic Manipulation

Construction of CRISPR-Cas9 plasmid: The synthesized forward oligonucleotide strand and reverse oligonucleotide strand of sgRNA were annealed to obtain a double-stranded oligonucleotide strand (in the present invention, the sgRNA sequence refers to the sequence of the forward oligonucleotide strand of the sgRNA), which was then ligated to pX330-mCherry enzymatically cleaved with BbsI (New England Biolabs). The constructed corresponding plasmid was transfected into the AG-haESCs using Lipofectamine 2000 (Life Technologies) according to the instructions. 48 hours after transfection, the haploid cells with the red fluorescent protein were sorted by flow cytometry (FACSAriaII, BD Biosciences) and then plated at a low density. After 4-5 days of growth, monoclones were picked up for subsequent construction of cell lineages. Finally, cell lines with corresponding gene mutations were obtained by sequencing target genes by PCR.

If gene knock-in was involved, a double-stranded DNA donor needed to be constructed.

Preparation of Double-Stranded DNA Donor:

A sequence encoding EGFP, mCherry or ECFP was amplified and then ligated to the pMD19-T vector, to give pMD19-T-EGFP/mCherry/ECFP. Subsequently, the left and right homologous arms of the target gene were inserted into the pMD 19-T-EGFP/mCherry/ECFP vector.

1.5. Virus Production and Viral Infection of Double Knockout AG-haESCs (DKO-AG-haESCs)

The viral sgRNA library of mice and the Cas9 expressing viral plasmid have been reported mice (Cong., L, Ran, F. A., Cox, D., Lin, S., Barretto, R., Habib, N., Hsu, P. D., Wu, X., Jiang, W., Marraffini, L A., et al. (2013). Multiplex genome engineering using CRISPR/Cas systems. Science 339, 819-823; and Koike-Yusa, H., Li, Y., Tan, E. P., Velasco-Herrera Mdel, C., and Yusa, K. (2014). Genome-wide recessive genetic screening in mammalian cells with a lentiviral CRISPR-guide RNA library. Nature biotechnology 32, 267-273, 2014). The viral sgRNA library of mice and the Cas9 expressing viral plasmid used in the present invention were provided by Addgene. To prepare the virus, HEK293T was passaged in advance into a 10 cm petri dish, 3 µg of viral plasmid (lentiviral sgRNA library or lentiviral Cas9) and 9 µg of ViraPower Lentiviral Packaging Mix (Invitrogen) were transfected into HEK293T cells by using Lipofectamine® 2000 Reagent (Invitrogen, Life Technologies). The supernatant were collected 72 hours after transfection and concentrated with Lenti-Concentin virus precipitation solution (SBI) and then stored at −80° C.

Infection with lentiviral Cas9: A cell suspension of $10^8$ DKO-AG-haESCs was infected for 48 hours with 8 µg/ml polybrene (Sigma) and packaged lentiviral Cas9, and then screened for 3 days with 10 µg/ml blasticidin (Sigma). The remaining resistant clone was a cell line integrated with lentiviral Cas9.

Infection with lentiviral sgRNA library: A cell suspension of $10^8$ DKO-AG-haESCs was infected for 48 hrs with 8 µg/ml polybrene (Sigma) and packaged lentiviral CRISPR-sgRNA library, and then screened for 2 days in a medium comprising 1 µg/ml puromycin (Invitrogen), to obtain a positive clone that is a cell line carrying lentiviral sgRNA library.

Co-Infection with Lentiviral Cas9 and Lentiviral sgRNA Library:

A cell line integrated with lentiviral Cas9 was prepared first, then further infected with the lentiviral sgRNA library, and then screened for 2 days in a medium comprising 1 µg/ml puromycin (Invitrogen), to obtain a positive clone that is a cell line integrated with lentiviral Cas9 and lentiviral sgRNA library.

If the DKO-AG-haESC cell line was only infected with the lentiviral sgRNA library, then the cells did not express Cas9. At this time, transfection with the pX330-mCherry plasmid at the cellular level was needed to achieve the genome editing.

1.6. Bisulfite Sequencing for Methylation

1) Mouse DNA was packaged into beads with 15 µl of 2% LMP agarose (low melting point agarose), 460 µl of DNA digestion buffer, and then 40 µl of proteinase K were added to each sample and the sample was digested by incubation overnight at 50° C.

2) After 3 washes with TE, the beads were reacted with a bisulfite solution and incubated at 50° C. for 4-8 hours.

3) Nested PCR was performed using the beads as a template, and the PCR product was recovered and then ligated to the PMD19-T vector, followed by transformation and plating.

4) 10 colonies were picked from each sample for sequencing.

If the EZ DNA methylation Gold kit (ZYMO Research) was used, an appropriate amount of DNA was prepared, and the following procedures were operated according to the steps of use of the kit. The resulting product recovered with the kit was used as a template for PCR, the product was recovered and then ligated to the PMD19-T vector, followed by transformation and plating. 10 colonies were picked from the plate for sequencing.

1.7. Fluorescent Quantitative PCR

Total RNA was extracted from the cells or organs with Trizol reagent (Invitrogen) and then 1 μg of total RNA was reversely transcripted into cDNA using the First Strand cDNA Synthesis kit (TOYOBO). Real-time fluorescent quantitative PCR reactions were performed on a Bio-Rad CFX96 instrument using SYBR Green Realtime PCR Master Mix (TOYOBO), with 3 replicates for each set of samples. All the gene expression levels were detected with the expression level of housekeeping gene Gapdh as an internal reference.

1.8. Cobra Assay 1) 100 ng of sample DNA was taken and enzymatically cleaved with TaqI restriction endonuclease (Fementas) (T/CGA) for 15 min 2) Agarose gel electrophoresis was performed.

1.9. Construction of Semi-Cloned Mice by ICAHCI, ROSI and Embryo Transfer

Intracytoplasmic AG-haESCs Injection (ICAHCI):

To obtain semi-cloned (SC) embryos, AG-haESCs were treated for 8 hrs with a medium containing 0.05 μg/ml colchicine to synchronize the cells to M phase and then intracytoplasmically injected into the oocytes. The digested AG-haESCs were washed 3 times with HEPES-CZB medium and then re-suspended in 3% (w/v) polyvinylpyrrolidone (PVP) in HEPES-CZB medium. Nuclei of AG-haESCs in M phase were injected into MII oocytes under a Piezo microscope. The reconstructed embryos were cultured in CZB medium for 1 hour and then activated with a CB-free medium for 5-6 hours. After activation, all the reconstructed embryos were cultured in KSOM medium at 37° C., and 5% $CO_2$. ICAHCI embryos reached 2-cell embryo after being cultured in the KSOM medium for 24 hours.

ROSI (Round Spermatid Injection):

The operation followed a reported method (Kishigami, S., Wakayama, S., Nguyen, V. T., and Wakayama, T. (2004). Similar time restriction for intracytoplasmic sperm injection and round spermatid injection into activated oocytes for efficient offspring production. Biology of reproduction 70, 1863-1869).

Every 15-20 2-cell embryos obtained by ICAHCI or ROSI were transferred into each uterus of pseudopregnant ICR mice at 0.5 dpc (0.5 day post-mating). The female mice experienced caesarean section or natural birth after 19.5 days of pregnancy. Caesarean section was done for reconstructed embryos obtained with WT AG-haESCs or single DMR knockout AG-haESCs, and expired fetuses were quickly peeled off from the female's uterus. For embryos obtained by ROSI or with DKO-AG-haECs, females after 19.5 days of pregnancy experienced natural birth. After removing the fluid from the born mice, the mice were placed in an oxygen incubator, and survived mice were subsequently nourished by the surrogate females.

1.10. RNA-seq and Gene Expression Analysis

The RNA-seq library of total RNA was established according to Illumina's official TreSeq RNA Sample Prep v2 Guide. After establishment, deep sequencing was performed on the IlluminaHiSeq 2000 instrument available from the Computational Biology Center of the Institute of Computing Biology, Chinese Academy of Sciences-Max-Planck-Gesellschaft zur Förderung der Wissenschaften e.V. 6 samples, comprising 2 WT AG-haESCs $H19^{\Delta^{DMR}}$-$IG^{\Delta^{DMR}}$-AGH, $H19^{\Delta^{DMR}}$-$IG^{\Delta^{DMR}}$-AGH-OG3, $IG^{\Delta^{DMR}}$-$H19^{\Delta^{DMR}}$-AGH and round spermatid were subjected to subsequent analysis.

The algorithm for gene expression level was RPKM, specifically as described in (Yang, L., Duff, M. O., Graveley, B. R., Carmichael, G. G., and Chen, L. L. (2011). Genomewide characterization of non-polyadenylated RNAs. Genome biology 12, R16).

The p-value of differentially expressed genes was calculated using the waldscore method (Yang et al., Genome boil 2011) in which abs (waldscore) was set to be >1.96 (that is, p-value<0.05), and then the differentially expressed genes were screened.

1.11. RRBS (Reduced Representation Bisulfite Sequencing)

The RRBS library was established according to Illumina's official protocol, and then sequenced on the IlluminaHiSeq 2000 instrument (Gu, H., Smith, Z. D., Bock, C., Boyle, P., Gnirke, A., and Meissner, A. (2011). Preparation of reduced representation bisulfite sequencing libraries for genome-scale DNA methylation profiling. Nature protocols 6, 468-481.). All sequencing reads were aligned with the mouse genome.

1.12. Genotyping Methods

The extracted genomic DNA was amplified by PCR using corresponding primers, and the PCR product was further subjected to agarose gel electrophoresis.

Example 1

Construction of Semi-Cloned Mice Based on H19 DMR Single Knockout AG-haESC Line

A. Construction of AG-haESC Line:

Source of spermatids: H19 43.8 kb KO mice (C57/B6 background, homozygous);

Source of oocytes: B6D2F1 (C57BL/6 X DBA2) female mice

Figure 1B:
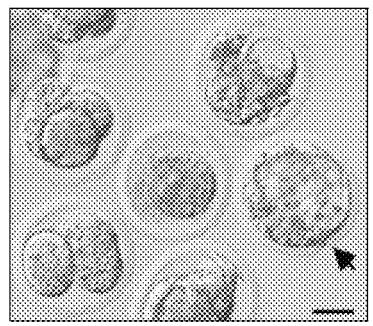
FIG. 1B shows androgenetic haploid embryos produced by injection of $H19^{\Delta DMR}$ spermatids into enucleated MII oocytes.
Figure 1C:
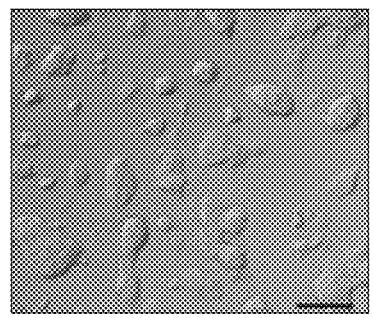
FIG. 1C shows one of the AG-haESC lines established with an androgenetic haploid blastocyst.
Figure 1D:
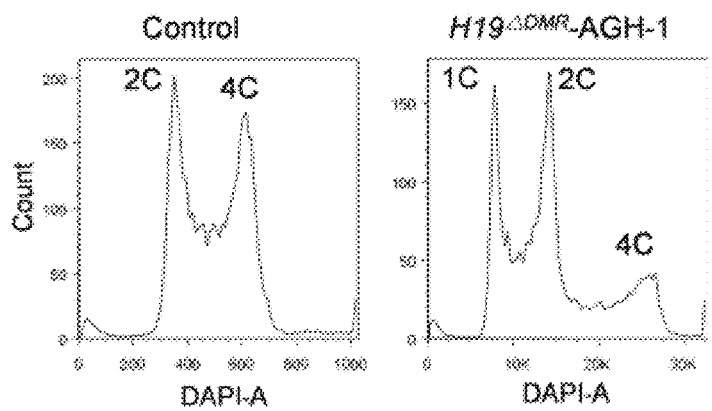
FIG. 1D shows $H19^{\Delta DMR}$ AG-haESCs ($H19^{\Delta DMR}$-AGH-1) established by multiple FACS enrichments of haploid cells.

The haploid sperm heads of H19 Δ3.8 kb mice were injected into enucleated oocytes (FIG. 1A) following the method as described in Section 1.3, to obtain reconstructed blastocysts, with which AG-haESC cell lines were constructed. Three haploid cell lines were established from 250 reconstructed blastocysts (which were designated as $H19^{\Delta^{DMR}}$-AGH-1, $H19^{\Delta^{DMR}}$-AGU-2, $H19^{\Delta^{DMR}}$-AGU-3) (FIGS. 1B-1D).

Figure 1E:
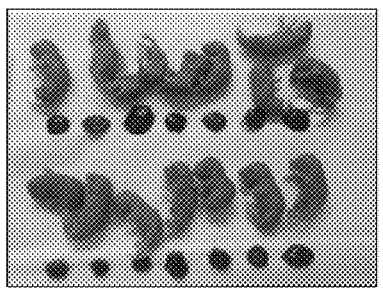
FIG. 1E shows SC mice produced with $H19^{\Delta DMR}$-AGH-1 (p8) by ICAHCI.

B. Construction of Semi-Cloned Mice:

Following the method as described in Section 1.9, $H19^{\Delta^{DMR}}$-AGH cells were used as a donor for ICAHCI, and 1443 2-cell embryos reconstructed with these 3 cell lines were transferred into the pseudopregnant female mice. Finally, 86 healthy, viable semi-cloned mice and 39 growth-arrested mice were obtained by caesarean section of the female mice on day 19.5 after pregnancy (FIG. 1E, Table 1). The birth rate in normal half-cloned mice is about 5.9%; however, about 2.7% of the semi-cloned mice developed from the embryos constructed with $H19^{\Delta^{DMR}}$-AGH still have abnormal growth.

Semi-cloned mice were constructed with wild-type AG-haESCs as a donor for ICAHCI. The birth rate of normal semi-cloned mice is about 0.7-1.8%.

C. Detection of Gtl2 Expression

Fluorescent quantitative PCR was used to detect whether aberrant high expression of Gtl2 was also present in the major organs of H19$^{\Delta DMR}$-AGH-derived growth-arrested mice, following the method as described in Section 1.7.

```
Primer sequences for fluorescent quantitative PCR:
Gtl2-F:
                                            (SEQ ID NO. 77)
TTGCACATTTCCTGTGGGAC Gtl2-R:
                                            (SEQ ID NO. 78)
AAGCACCATGAGCCACTAGG
```

The experimental results show that Gtl2 overexpression occurs in most of the organs tested in growth-arrested semi-cloned mice compared to normal mice (Fig. S1E).

D. Methylation Analysis

Experimental Methods: The analysis was carried out following the methods as described in Sections 1.6 and 1.8.

```
Primers used:
IG DMR-BS-OF:
                                            (SEQ ID NO. 79)
TTAAGGTATTTTTATTGATAAAATAATGTAGTTT IGD MR-BS-OR:
                                            (SEQ ID NO. 80)
CCTACTCTATAATACCCTATATAATTATACCATAA IG DMR-BS-IF:
                                            (SEQ ID NO. 81)
TTAGGAGTTAAGGAAAAGAAAGAAATAGTATAGT IG DMR-BS-IR:
                                            (SEQ ID NO. 82)
TATACACAAAAATATATCTATATAACACCATACAA
```

Figure 1F:
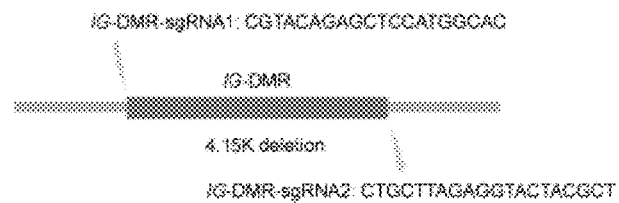
FIG. 1F is a view schematically showing an IG-DMR knockout sgRNA sequence (SEQ ID NO. 1-2).
Figure 1L:
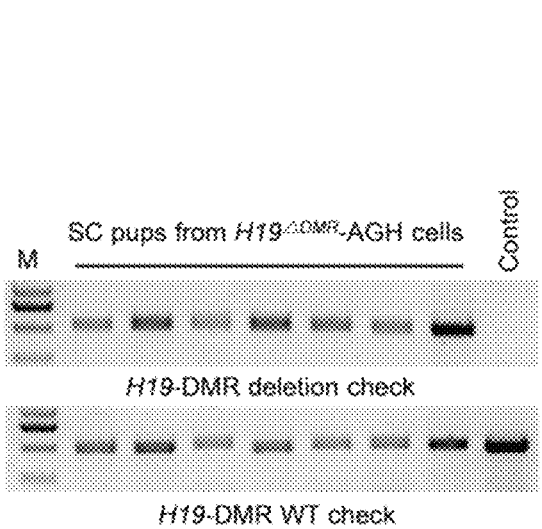
FIG. 1L shows genotyping of $H19^{\Delta DMR}$-AGH cell-derived SC mice.
Figure 1N:
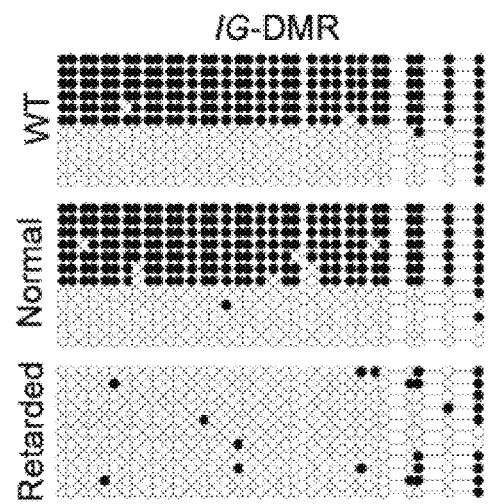
FIG. 1N shows severely erased methylation imprinting of IG-DMR in growth-arrested SC mice.
Figure 1M:
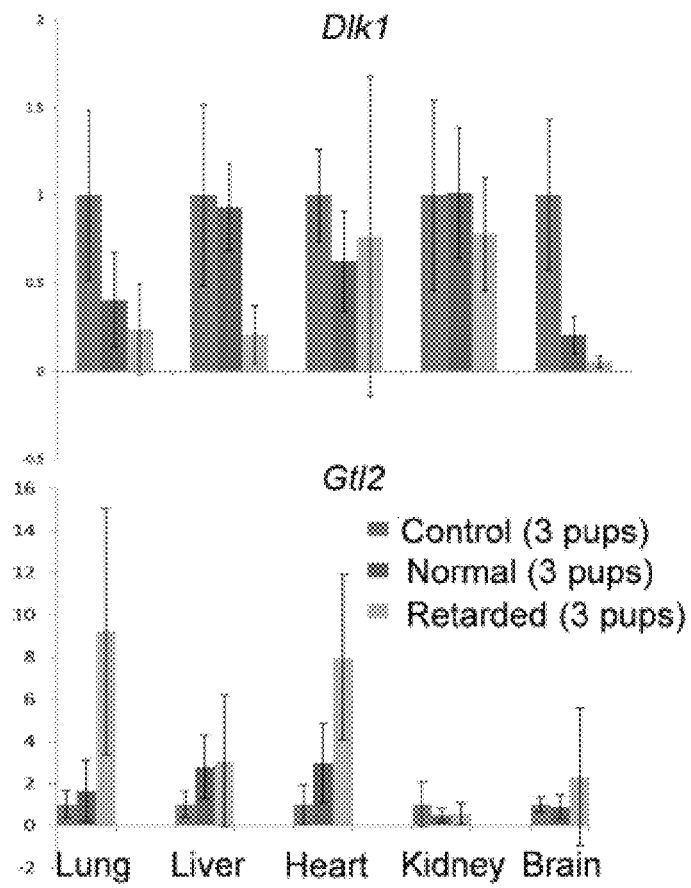
FIG. 1M shows expression analysis of imprinted gene (Gtl2 and Dlk1) in various organs of $H19^{\Delta DMR}$-AGH cell-derived normal and growth-arrested SC mice.
Figure 1O:
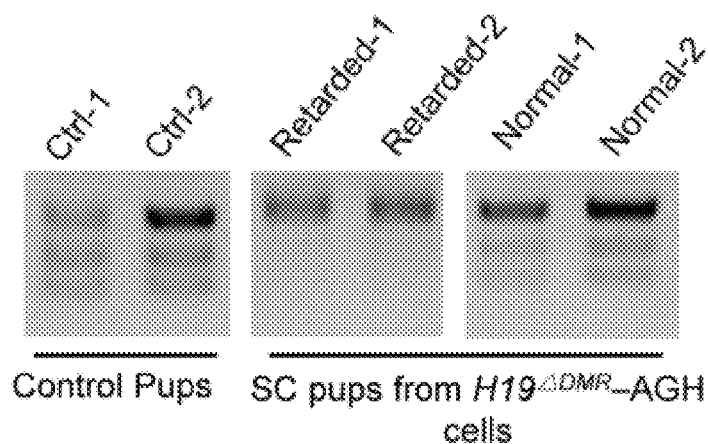
FIG. 1O shows Cobra assay of IG-DMR in growth-arrested and normal SC mice.
Figure 1P:
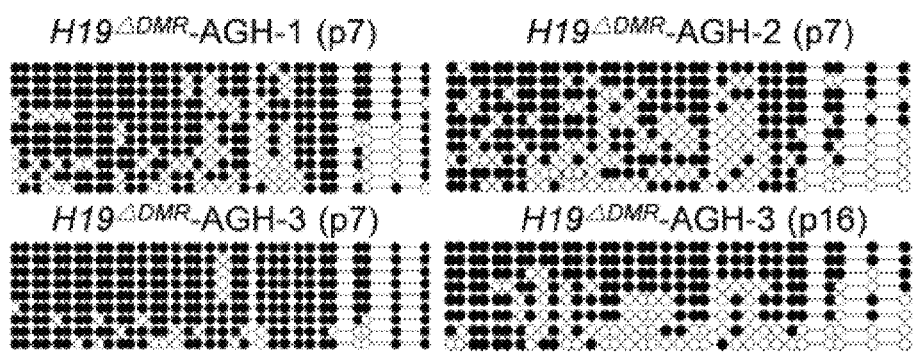
FIG. 1P shows methylation state of IG-DMR in $H19^{\Delta DMR}$-AGH cell line.

The results of methylation analysis show that the growth-arrested semi-cloned mice show obvious hypomethylation in the IG-DMR region of the differential methylation sites in the Dlk1-Gtl2 imprinted cluster (FIGS. 1N-1O). Interestingly, a more severe loss of IG-DMR methylation imprinting occurred in the later generation of H19$^{\Delta DMR}$-AGH (H19$^{\Delta DMR}$-AGU-1, p16) compared to with its earlier generation (H19$^{\Delta DMR}$-AGH-1, p7), resulting in a significantly increased rate of growth arrested mice (FIG. 1P, Table S1). This indicates that the abnormal expression of Gtl2 may be another important factor leading to the failure in development of the semi-cloned mice obtained with H19$^{\Delta DMR}$-AGH cells.

Example 2

Construction of Semi-Cloned Mice Based on H19 DMR and IG-DMR Double Knockout AG-haESC Line A. Construction of H19 DMR and IG-DMR Double Knockout AG-haESC Line:

The construction was carried out following the method as described in Section 1.4.

2 sgRNAs were designed according to the sequence between Dlk1 and Gtl2 which had a 4.15 kb IG-DMR knocked out (designated as IG-DMR-sgRNA1 and IG-DMR-sgRNA2) (FIG. 1F).

```
IG-DMR-sgRNA1 sequence:
                                            (SEQ ID NO: 1)
CGTACAGAGCTCCATGGCAC IG-DMR-sgRNA2 sequence:
                                            (SEQ ID NO: 2)
CTGCTTAGAGGTACTACGCT
```

The plasmids pX330-mCherry expressing Cas9 and IG-DMR-sgRNAs were constructed and transfected into the H19$^{\Delta DMR}$-AGH cells, to finally obtain 71 AG-haESC lines. The sequencing of the PCR product of the target gene (IG-DMR deletion check-F: TGTGCAGCAGCAAAGCTAAG (SEQ ID NO. 83); IG-DMR deletion check-R: ATACGATACGGCAACCAACG (SEQ ID NO. 84)) found that the IG-DMR were successfully knocked out in 58 cell lines (designated as H19$^{\Delta DMR}$-IG$^{\Delta DMR}$-AGH-1 through H19$^{\Delta DMR}$-IG$^{\Delta DMR}$-AGH-58) (FIGS. 1G, 2I and 2J). Off-target analysis of H19$^{\Delta DMR}$-IG$^{\Delta DMR}$-AGH-2 shows that no mutations occur to a total of 22 potential off-target sites (Table S2), where these sites are predicted by genome-wide searching by using software reported previously (Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nature biotechnology 31, 827-832).

B. Construction of Semi-Cloned Mice:

Following the method as described in Section 1.9, H19$^{\Delta DMR}$-IG$^{\Delta DMR}$-AGH cells were used as a donor for ICAHCI to construct semi-cloned mice. The results show that 22.3% of the semi-cloned embryos can well developed (FIG. 1H, FIG. 2K, Table 1, Table S1), which is similar to the ROSI birth rate reported by our laboratory (Table 1) or other laboratories (Kishigami, S., Wakayama, S., Nguyen, V. T., and Wakayama, T. (2004). Similar time restriction for intracytoplasmic sperm injection and round spermatid injection into activated oocytes for efficient offspring production. Biology of reproduction 70, 1863-1869.). Furthermore, compared with the semi-cloned mice obtained with wild type AG-haESCs and H19$^{\Delta DMR}$-IG$^{\Delta DMR}$-AGH by ICAHCI that require caesarean section, after the embryos reconstructed with H19$^{\Delta DMR}$-IG$^{\Delta DMR}$-AGH-2 is transferred to pseudopregnant female mice, the pseudopregnant female mice can carry out natural birth, and the born semi-cloned mice all survive healthy. The data suggests that H19$^{\Delta DMR}$-IG$^{\Delta DMR}$-AGH cells obtain characteristics resembling a round spermatid successfully by knocking out IG-DMR, from which semi-cloned mice can be produced efficiently.

Example 3

Construction of Semi-Cloned Mice Based on IG-DMR Single Knockout AG-haESC Line

A. Construction of AG-haESC Line:

Source of spermatids: IG-DMR KO mice;

Source of oocytes: B6D2F1 (C57BL/6 X DBA2) female mice

The haploid sperm heads of IG-DMR KO mice were injected into enucleated oocytes following the method as described in Section 1.3, to obtain reconstructed blastocysts, with which AG-haESC cell lines were constructed. Among the 8 haploid cell lines established, 2 cell lines carried IG-DMR knockout (designated as IG$^{\Delta DMR}$-AGH-1 and IG$^{\Delta DMR}$-AGH-2)

Figure 2A:
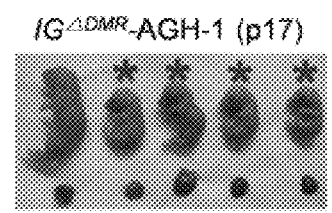
FIG. 2A shows semi-cloned mice produced with $IG^{\Delta DMR}$-AGH-1 cell line (P17), in which asterisk represents growth-arrested SC mice, which die shortly after birth.

B. Construction of Semi-Cloned Mice:

Following the method as described in Section 1.9, $IG^{\Delta DMR}$-AGH cells were used as a donor for ICAHC to construct semi-cloned mice. It is found that the $IG^{\Delta DMR}$-AGH cells are not donors effective in the production of semi-cloned mice (Table 1, Table S1), with which it is difficult to obtain healthy normal SC mice (where only 4 normal SC mice are obtained from 499 transferred embryos) (FIGS. 2A and 2M). Moreover, most of the mice are growth arrested.

C. Methylation Analysis

Experimental Methods: The analysis was carried out following the methods as described in Sections 1.6 and 1.8.

```
Primers used:
H19 DMR-BS-OF:
                                     (SEQ ID NO. 85)
5' GAGTATTTAGGAGGTATAAGAATT 3'

H19 DMR-BS-OR:
                                     (SEQ ID NO. 86)
5' ATCAAAAACTAACATAAACCCCT 3'

H19 DMR-BS-IF:
                                     (SEQ ID NO. 87)
5' GTAAGGAGATTATGTTTATTTTTGG 3'

H19 DMR-BS-IR:
                                     (SEQ ID NO. 88)
5' CCTCATTAATCCCATAACTAT 3'
```

Figure 2B:
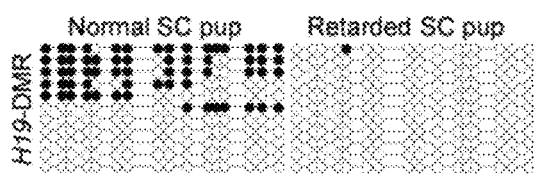
FIG. 2B shows methylation state of H19 DMR in normal and abnormal SC mice produced with $IG^{\Delta DMR}$-AGR-1 cell line.

The result show that the H19 DMR of $IG^{\Delta DMR}$-AGH cell line suffers erased methylation, and complete loss of methylation occurs in the growth-arrested mice (FIGS. 2B, 2N, and 2O).

Example 4

Construction of Semi-Cloned Mice Based on H19 DMR and IG-DMR Double Knockout AG-haESC Line A. Construction of H19 DMR and IG-DMR Double Knockout AG-haESC Line:

The construction was carried out following the method as described in Section 1.4.

```
H19 Δ3.8kb DMR KO sgRNA sequence:
H19-3.8K sgRNA-1:
                                     (SEQ ID NO: 3)
CATGAACTCAGAAGAGACTG H19-3.8K sgRNA-2:
                                     (SEQ ID NO: 4)
AGGTGAGAACCACTGCTGAG
```

Figure 2C:
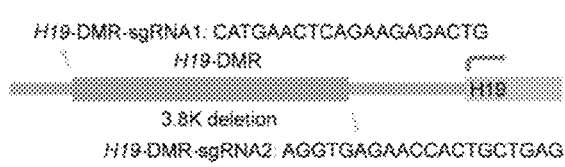
FIG. 2C schematically shows H19 DMR knockout sgRNAs designed (SEQ ID NO. 3-4).

The H19 43.8 kb DMR were knocked out from the $IG^{\Delta DMR}$-AGH cell line obtained in the above example by the CRISPR-Cas9 method (see Thorvaldsen, J. L., Mann, M. R., Nwoko, O., Duran, K. L., and Bartolomei, M. S. (2002). Analysis of sequence upstream of the endogenous H19 gene reveals elements both essential and dispensable for imprinting. Molecular and cellular biology 22, 2450-2462), and 13 DKO-AG-haESC cell lines were successfully obtained (designated as $IG^{\Delta DMR}$-$H19^{\Delta DMR}$-AGH-1 through $IG^{\Delta DMR}$-$H19^{\Delta DMR}$-AGH-13) (FIGS. 2C and 2P, and Table S2).

B. Construction of Semi-Cloned Mice:

Following the method as described in Section 1.9, 2 cell lines above were used as a donor for ICAHCI to construct semi-cloned mice. The results show that the 2 cell lines have the similar ability to produce health SC mice as the $H19^{\Delta DMR}$-$IG^{\Delta DMR}$-AGH cells (FIGS. 2Q and 2J, and Table 1, Table S1).

Example 5

Construction of Semi-Cloned Mice Based on H19-DMR and IG-DMR Double Knockout AG-haESC Line A. Construction of H19-DMR and IG-DMR Double Knockout AG-haESC Line:

Initial cells: 21st-generation AGH-OG-3 cells of WT-AG-haESC cell line AGH-OG-3

It has been reported that the $22^{nd}$ generation of this cell line has substantially lost the ability to produce healthy, semi-cloned mice (Yang, H., Shi, L., Wang, B. A., Liang, D., Zhong, C., Liu, W., Nie, Y., Liu, J., Zhao, J., Gao, X., et al. (2012). Generation of genetically modified mice by oocyte injection of androgenetic haploid embryonic stem cells. Cell 149, 605-617).

The oligo of sgRNA were annealed and then the sgRNAs of H19 and IG-DMR were respectively ligated to the BbsI digested px330-mCherry plasmid and transformed. Plasmid was extracted from the bacterial suspension sequenced to be correct for subsequent transfection.

The 21st generation of the AGH-OG-3 cell line was transformed with the plasmid obtained above.

Figure 2D:
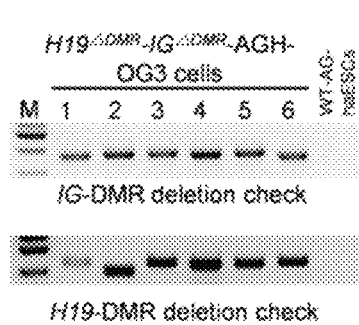
FIG. 2D shows genotyping of $H19^{\Delta DMR}$-AGH-OG3 cell lines, produced by knocking out H19 and IG-DMRs from AGH-OG3 cell line.
Figure 3B:
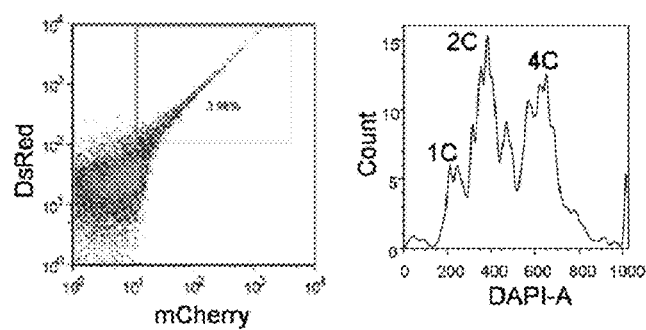
FIG. 3B shows mCherry positive cells collected by FACS, which are plated in a Petri dish, to obtain DKO-AG-haESCs with mutant Tet family of genes.
Figure 3C:
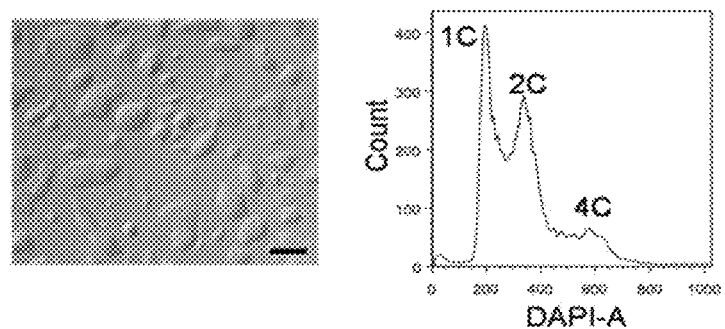
FIG. 3C shows a Tet-TKO-DAH cell line obtained.
Figure 3D:
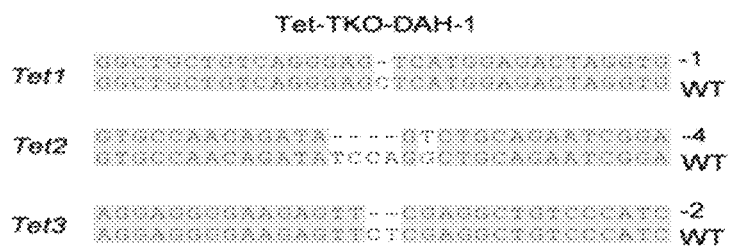
FIG. 3D shows sequencing of Tet1, Tet2 and Tet3 in the Tet-TKO-DAH cell line (Tet1 wild-type: SEQ ID NO. 19; Gene mutation of Tet1 in Tet-TKO-DAH-1: SEQ ID NO. 20; Tet2 wild-type: SEQ ID NO. 21; Gene mutation of Tet2 in Tet-TKO-DAH-1: SEQ ID NO. 22; Tet3 wild-type: SEQ ID NO. 23; Gene mutation of Tet3 in Tet-TKO-DAH-1: SEQ ID NO. 24).
Figure 3E:
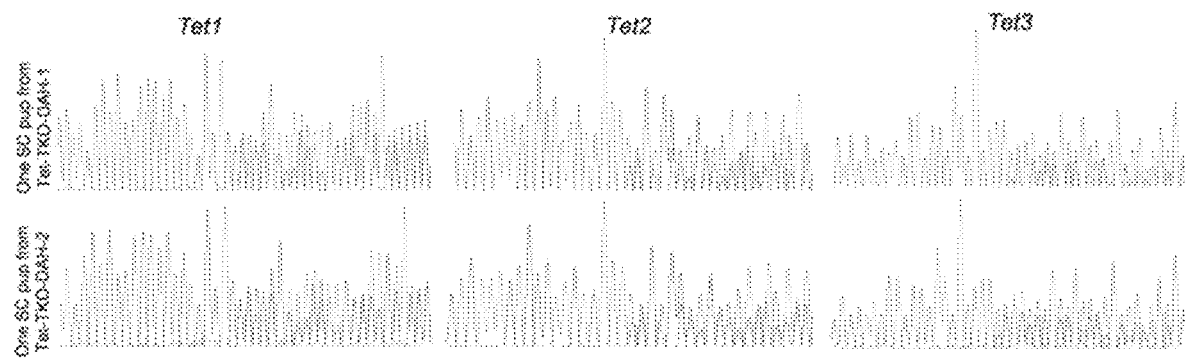
FIG. 3E shows sequencing of PCR products of Tet1, Tet2 and Tet3 genes in SC mice produced with Tet-TKO-DAH-1 and Tet-TKO-DAH-2 cell lines.
Figure 3F:
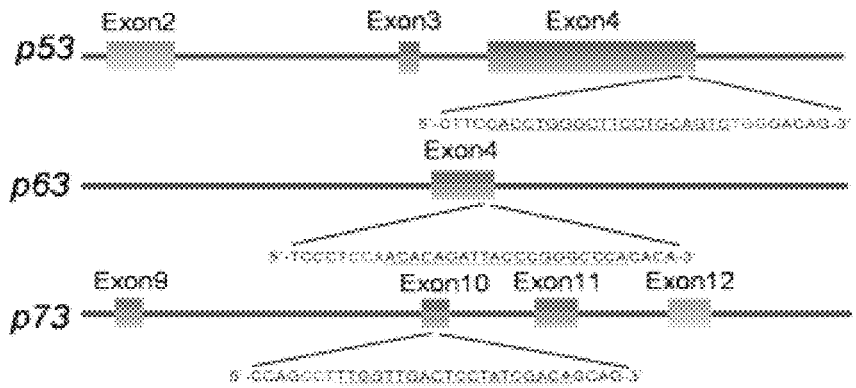
FIG. 3F is a view schematically showing p53, p63 and p73 sgRNAs (SEQ ID NO. 8-10).
Figure 3J:
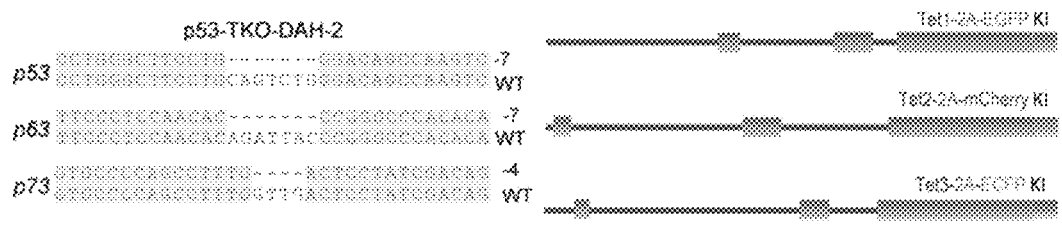
FIG. 3J shows sequencing of 2 DKO-AG-haESCs cell lines ($H19^{\Delta DMR}$-$IG^{\Delta DMR}$-AGH-OG3-1 and $H19^{\Delta DMR}$-$IG^{\Delta DMR}$-AGH-OG3-1) obtained by knocking out H19 and IG-DMR from WT-AG-haESCs (AGH-OG3) (SEQ ID NO. 31-34).
Figure 3J:
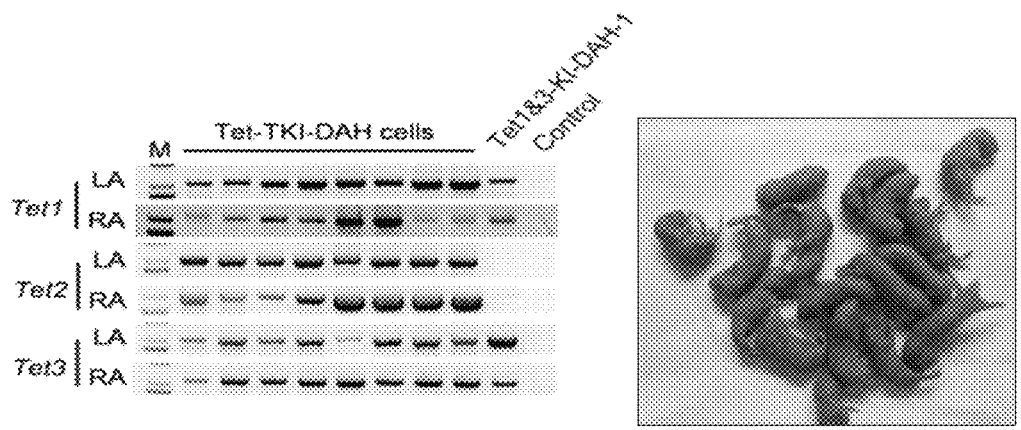

12 H19 and Gtl2 DMR double knockout AG-haESC cell lines (designated as $H19^{\Delta DMR}$-$IG^{\Delta DMR}$-AGH-OG3-1 through $H19^{\Delta DMR}$-$IG^{\Delta DMR}$-AGH-OG3-12) were finally obtained (FIGS. 2D and 3J and Table S2).

Figure 3L:
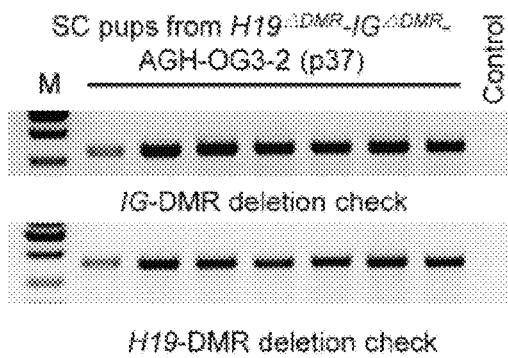
FIG. 3L shows genotyping of SC mice produced with $H19^{\Delta DMR}$-$IG^{\Delta DMR}$-AGH-OG3-2 cell line.

B. Construction of Semi-Cloned Mice:

Following the method as described in Section 1.9, $H19^{\Delta DMR}$-$IG^{\Delta DMR}$-AGH-OG3 cells were used as a donor for ICAHCI to construct semi-cloned mice. Surprisingly, by injecting 2 of these cell lines into MII oocytes, about 17% of semi-cloned embryos were able to develop fully (FIG. 3K, 3L, Table 1, and Table S1). This shows that WT-AG-haESCs, which had previously completely lost the ability to produce SC mice, were able to regain characteristics resembling a round spermatid after knockdown of H19-DMR and IG-DMR.

Example 6

Genotyping of SC Mice Obtained with 3 DKO-AG-haESC Lines

Genotyping method: The method as described in Section 1.12 was used.

```
H19-DMR deletion check-F2:
                                     (SEQ ID NO. 89)
GTGGTTAGTTCTATATGGGG H19-DMR deletion check-R2:
                                     (SEQ ID NO. 90)
TCTTACAGTCTGGTCTTGGT IG-DMR deletion check-F:
                                     (SEQ ID NO. 91)
TGTGCAGCAGCAAAGCTAAG IG-DMR deletion check-R:
                                     (SEQ ID NO. 92)
ATACGATACGGCAACCAACG
```

Figure 2E:
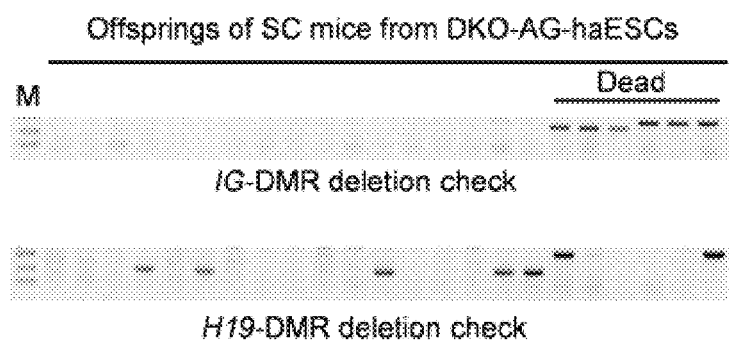
FIG. 2E shows genotyping of offspring obtained by mating SC mice produced with DKO-AG-haESCs, where the offspring carrying IG-DMR die before or shortly after birth.

Three H19-DMR and IG-DMR double-knockout AG-haESC cell lines were constructed by using the three methods described in the foregoing Examples 2, 4 and 5, and a total of 402 SC mice were obtained. A mouse birth rate of 20.2% was achieved with the transferred embryos. These DKO-AG-haESC derived SC mice are able to grow to adulthood and are capable of producing offspring. Genotyping of 33 neonatal mouse offspring in 7 litters find that 13 animals carry H19-DMR knockout and 11 animals are WT (FIG. 2E). 6 out of the other 9 mice have IG-DMR knockout and 3 have H19 and Gtl2 DMR double knockouts. The 9 mice died shortly after birth, consistent with the previously reported lethal phenotype of the maternally inherited IG-DMR before or after birth (Lin, S. P., Youngson, N., Takada, S., Seitz, H., Reik, W., Paulsen, M., Cavaille, J., and Ferguson-Smith, A C. (2003). Asymmetric regulation of imprinting on the maternal and paternal chromosomes at the Dlk1-Gtl2 imprinted cluster on mouse chromosome 12. Nature genetics 35, 97-102).

Example 7

Detection of Gene Expression and Methylation Analysis of AG-haESCs

RNA-seq and gene expression analysis were performed following the methods described previously in Sections 1.10 and 1.7.

Reagent: SYBR-Green (TOYOBO)

Primers for Q-PCR:

```
Primers for Q-PCR:
Gapdh-F:
                                     (SEQ ID NO. 93)
CACTCTTCCACCTTCGATGC Gapdh-R:
                                     (SEQ ID NO. 94)
CTCTTGCTCAGTGTCCTTGC Igf2-F:
                                     (SEQ ID NO. 95)
CTAAGACTTGGATCCCAGAACC Igf2-R:
                                     (SEQ ID NO. 96)
GTTCTTCTCCTTGGGTTCTTTC Gtl2-F:
                                     (SEQ ID NO. 97)
TTGCACATTTCCTGTGGGAC Gtl2-R:
                                     (SEQ ID NO. 98)
AAGCACCATGAGCCACTAGG Dlk-F
                                     (SEQ ID NO. 99)
ACTTGCGTGGACCTGGAGAA Dlk-R:
                                     (SEQ ID NO. 100)
CTGTTGGTTGCGGCTACGAT

H19-F:
                                     (SEQ ID NO. 101)
CATGTCTGGGCCTTTGAA

H19-R:
(SEQ ID NO. 102)
TTGGCTCCAGGATGATGT
```

Genome-wide methylation level analysis was performed following the method as described in Section 1.11.

Figure 2F:
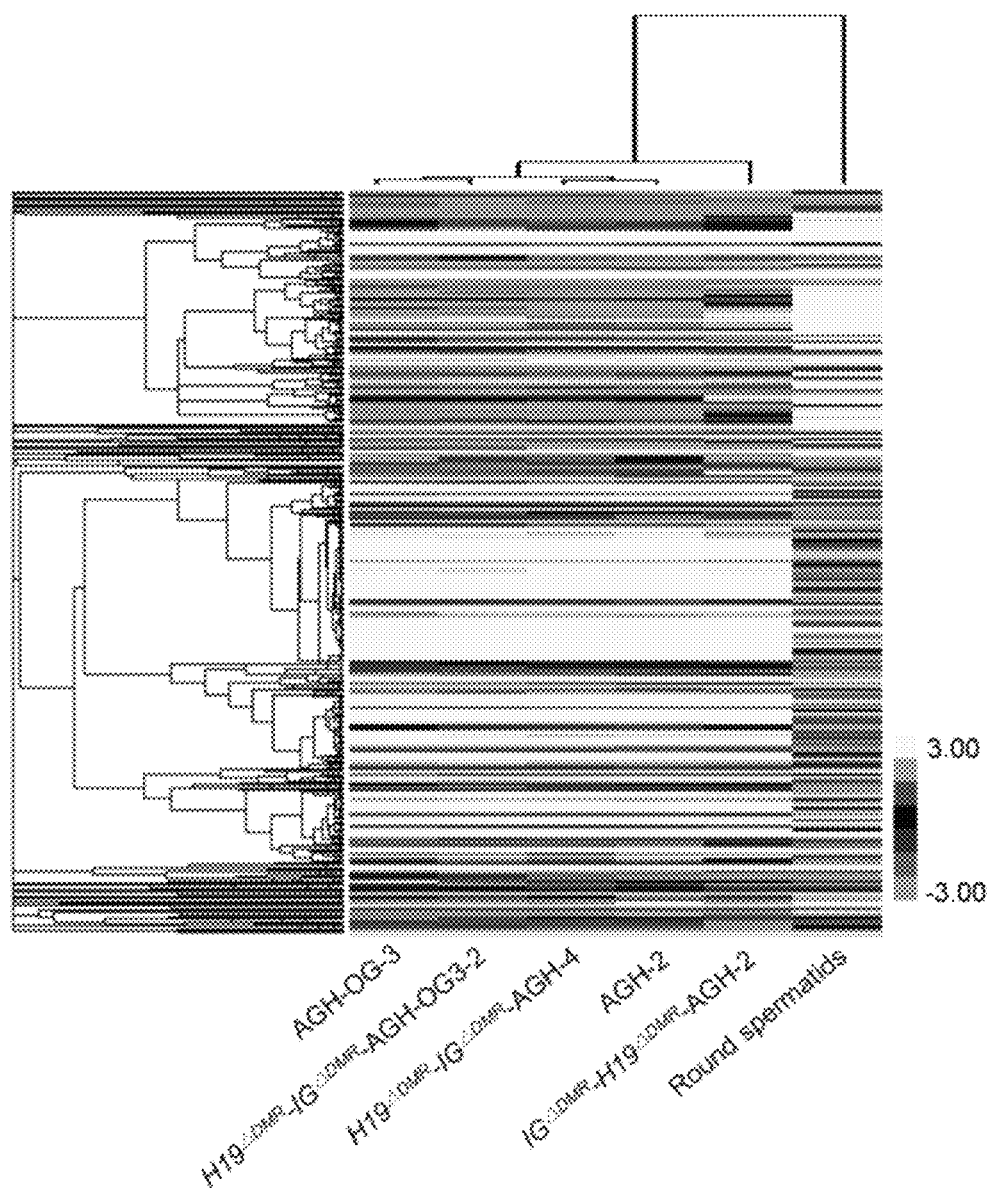
FIG. 2F shows analysis of gene expression profile of DKO-AG-haESCs by RNA-seq. The gene expression profile is clustering of the expression of all genes. The three DKO-AG-haESC cell lines show a gene expression profile that is similar to that of the AG-haESCs in the control group, but very different from that of the round spermatid. To avoid the effect of haploid diploidization on the expression profile, G0/G1 cells are collected by FACS for RNA-seq.
Figure 2G:
FIG. 2G shows imprinted gene expression profile of DKO-AG-haESCs. The expression profiles of three different DKO-AG-haESC lines are similar to that of the AG-haESCs in the control group, but different from that of the round spermatids in mice
Figure 2H:
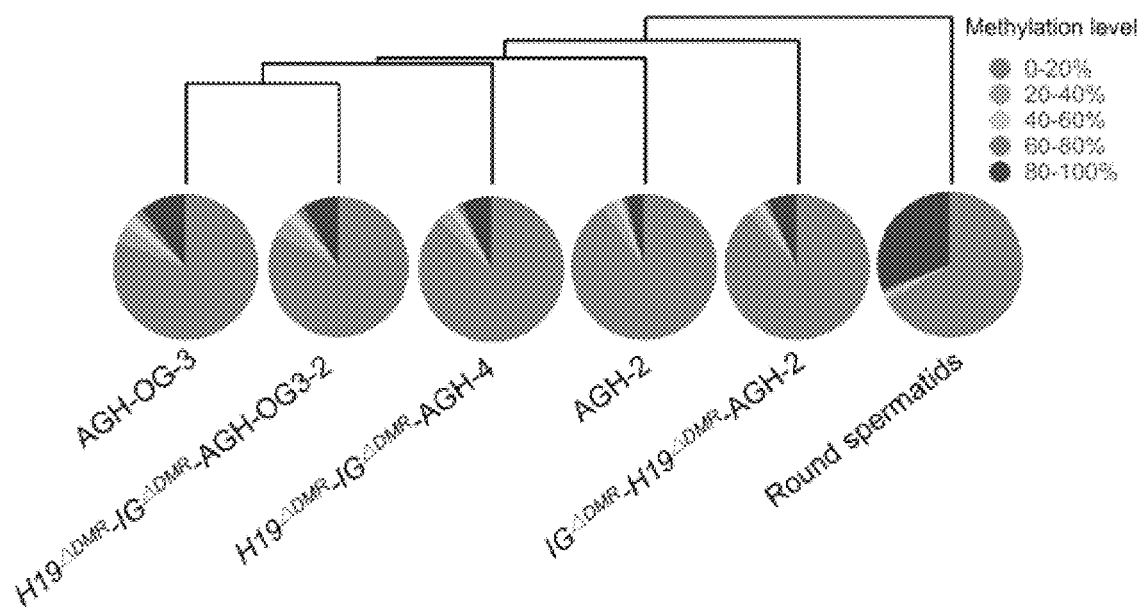
FIG. 2H shows analysis of methylation in DKO-AG-haESCs by RRBS.
Figure 3M:
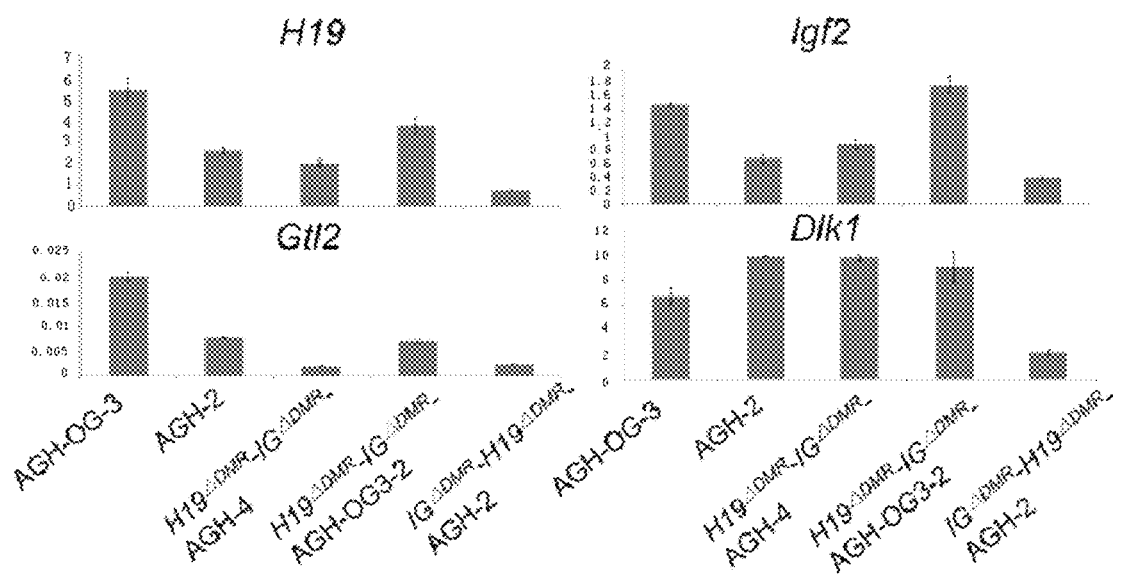
FIG. 3M shows expression analysis of imprinted gene (H19, Igf2, Gtl2 and Dlk1) in DKO-AG-haESCs and normal AG-haESCs, where after H19 and IG-DMR are knocked out, the expression of H19 and Gtl2 in AGH-OG-3 is down regulated, while the expression of Igf2 and Dlk1 is up regulated.
Figure 3N:
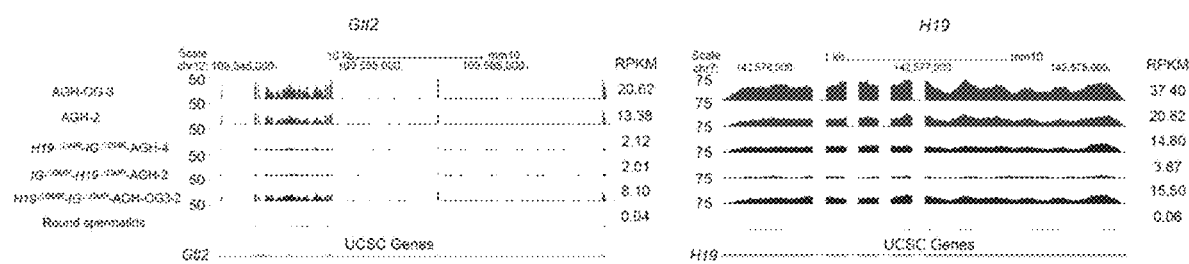
FIG. 3N shows bigwig track of H19 and Gtl2. The RNA-seq result shows that compared with WT-AG-haESCs, the expression level of H19 and Gtl2 in DKO-AG-haESCs is much lower.
Figure 3O:
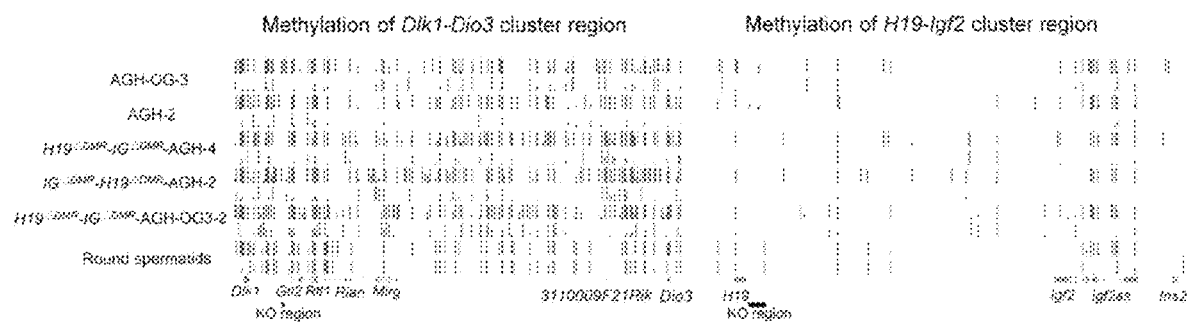
FIG. 3O shows the methylation levels in H19-Igf2 and Dlk1-Dio3 imprinted cluster regions.
Figure 3P:
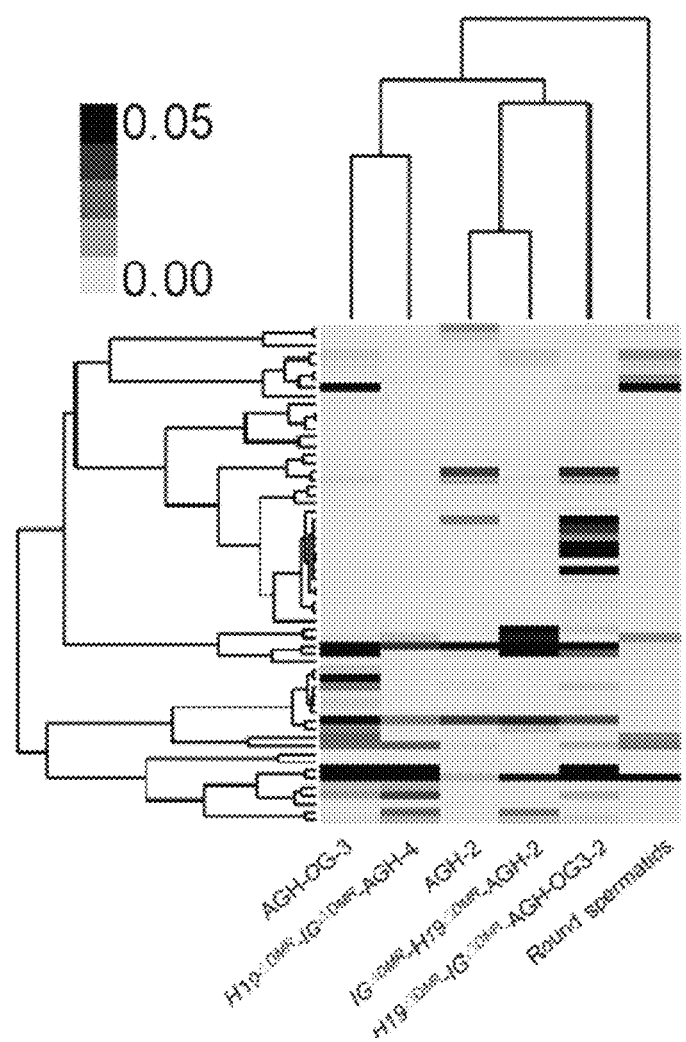
FIG. 3P shows the methylation state of imprinted genes in DKO-AG-haESCs, WT-AG-haESCs, and round spermatids.

The results of Q-PCR showed that the expression of H19 and Gtl2 is down-regulated while the expression of Igf2 and Dlk1 is up-regulated in DKO-AG-haESCs (Fig. 3M). The gene expression profiles of DKO-AG-haESCs, normal AG-haESCs and round spermatids were compared. Clustering data based on RNA-seq reveals that the expression profile of DKO-AG-haESCs is highly similar to that of WT-AG-haESCs, but greatly different from that of round spermatids (FIGS. 2F, 3N). Further analysis of the expression profiles of imprinted genes in DKO-AG-haESCs and WT-AG-haESCs revealed that all imprinted genes in DKO-AG-haESCs and WT-AG-haESCs have extremely similar expression levels (FIG. 2G). In order to further evaluate the epigenetics, reduced representation bisulfate sequencing (RRBS) was performed to detect the genome-wide methylation level. As shown in FIGS. 2H, 3O, and 3P, knockouts of H19 and Gtl2 DMRs do not alter the methylation levels in the promoter regions of all the genes and imprinted genes detected. Taken together, the results show that H19 and Gtl2 DMRs are two major impairments for AG-haESCs in obtaining characteristics resembling spherical spermatid.

Example 8

Production of Semi-Cloned Mice with DKO-AG-haESCs Carrying Multiple Genetic Modifications A. Construction of DKO-AG-haESCs Carrying Multiple Genetic Modifications:

The construction was carried out following the method as described in Section 1.4.

Initial cells: DKO-AG-haESCs. Knockouts of the TET family of genes employed the DKO-AG-haESCs prepared in Example 4, and knockouts of the p53 family of genes employed the DKO-AG-haESCs prepared in Example 2.

Target mutations: mutations of Tet1, Tet2, Tet3, and p53 family

Construction Procedure:

Construction procedure of Tet-TKO-DAH:

sgRNAs of Ted, Tet2, and Tet3 were annealed respectively, and ligated to a BbsI digested px330-mCherry plasmid respectively, and positive plasmids in which sgRNAs were ligated were picked up by sequencing.

```
Tet1 sgRNA sequence:
                                       (SEQ ID NO: 5)
GGCTGCTGTCAGGGAGCTCA Tet2 sgRNA sequence:
                                       (SEQ ID NO: 6)
GAAAGTGCCAACAGATATCC Tet3 sgRNA sequence:
                                       (SEQ ID NO: 7)
AAGGAGGGGAAGAGTTCTCG
```

The plasmids expressing the sgRNAs of Tet1, Tet2, and Tet3 were co-transformed into the DKO-AG-haESC cell line. mCherry positive cells were sorted, and plated in a Petri dish. After 5 days of growth, the clones were picked and passaged for amplification. The established cell line was identified for the Tet1, Tet2, and Tet3 mutations by sequencing the PCR product.

```
Primers for sequencing:
Tet1 check-F:
                                     (SEQ ID NO. 103)
GCCCCTGTTGTCTTATACGTT Tet1 check-R:
                                     (SEQ ID NO. 104)
CATTCGCCTCAGGACCAC Tet2 check-F:
                                     (SEQ ID NO. 105)
CCGCCACAAGAAAATATGTCC
```

-continued

Tet2 check-R:
(SEQ ID NO. 106)
AGCTAACTCTGGCAAACACC

Tet3 check-F:
(SEQ ID NO. 107)
CAGAGTGGCCTCAGTTTCCC

Tet3 check-R:
(SEQ ID NO. 108)
ACAACTTTTACCCAGGAGTCACAC

Construction Procedure of p53-TKO-DAH:

sgRNAs of p53, p63, and p73 were annealed respectively, and ligated to a BbsI digested px330-mCherry plasmid respectively, and positive plasmids in which sgRNAs were ligated were picked up by sequencing.

p53 sgRNA sequence:
(SEQ ID NO: 8)
CACCTGGGCTTCCTGCAGTC p63 sgRNA sequence:
(SEQ ID NO: 9)
TGGGCCCGGGTAATCTGTGT p73 sgRNA sequence:
(SEQ ID NO: 10)
TGTCGATAGGAGTCAACCAA The plasmids expressing the sgRNAs of p53, p63, and p73 were co-transfected into the DKO-AG-haESCs cell line. mCherry positive cells were sorted, and plated in a Petri dish. After 5 days of growth, the clones were picked and passaged for amplification. The established cell line was identified for the p53, p63, and p73 mutations by sequencing the PCR product.

P53 check-F:
(SEQ ID NO. 109)
CCCCTGTCATCTTTTGTCCCT

P53 check-R:
(SEQ ID NO. 110)
AAGAGAGTTCCACGTCCCTG

P63 check-F:
(SEQ ID NO. 111)
CACACCAAATAATGCCAATT

P63 check-R:
(SEQ ID NO. 112)
CAGACTCTCTTACCGTCCAG

P73 check-F:
(SEQ ID NO. 113)
GACCCACTTCTAAACCTGCC

P73 check-R:
(SEQ ID NO. 114)
CCATACCTCCTGTGCTCCTG

B. Construction of Semi-Cloned Mice:

Following the method as described in Section 1.9, the cells constructed above were used as a donor for ICAHCI to construct semi-cloned mice.

C. Results

In this example, Tet1, Tet2 and Tet3 were mutated in DKO-AG-haESCs by CRISPR-Cas9 method. The plasmids constructed to express Cas9 and 3 sgRNAs of Tet1, 2, and 3 (FIG. 3A) (see Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas-mediated genome engineering. Cell 153, 910-918) were transformed into DKO-AG-haESCs. 56 DKO-AG-haESC lines were finally established. The sequencing of the PCR products of the Tet1, 2, and 3 gene revealed that triple gene mutations occur in 18 cell lines (designated as Tet-TKO-DAH-1 through Tet-TKO-DAH-18) (FIGS. 3B-D and 4H). ICAHCI results of 4 of the cell lines indicated that SC mice with Tet1, 2 and 3 mutations can be obtained with corresponding rate (FIGS. 3E and 4I, Table 1 and Table S3). Corresponding SC mice can also be obtained with DKO-AG-haESCs with mutant p53 family of genes by ICAHCI (FIGS. 4K, 4L, Table 1 and Table S3). These results show that WT-AG-haESCs are failed to produce viable SC mice after in vitro genetic manipulation, but DKO-AG-haESCs are still able to efficiently and stably produce semi-cloned mice after gene editing.

Example 9

Gene Editing of DKO-AG-haESCs and Production of Semi-Cloned Mice Therewith

A. Construction of Genetically Edited DKO-AG-haESC Cell Line

Initial cells: DKO-AG-haESCs (prepared in Example 4)

Construction Procedure:

Construction Procedure of Tet1&3-KI-DAH:

sgRNAs of Tet1, and Tet3 were annealed and ligated to a BbsI digested px330-mCherry plasmid respectively, and positive plasmids in which sgRNAs were ligated were picked up by sequencing. For the preparation of Tet1-EGFP and Tet3-ECFP donors, pEGFP-N1 plasmid and pECFP-N1 plasmid were respectively used as a template (primers: P2A-fluorescence F: GCCACGAAGCAAGCAG-GAGATGTTGAAGAAAACCCCGGGCCTGT-GAGCAAGGGCG AGGAG (SEQ ID NO. 115); P2A-fluorescence R: CTTGTACAGCTCGTCCATG (SEQ ID NO. 116)), a sequence encoding EGFP or ECFP was amplified, and then correspondingly ligated to a multiclonal site on a pMD19-T vector, to obtain a pMD19-T-EGFP/ECFP vector. Subsequently, the left and right homologous arms of the gene of interest were respectively inserted into two sides of the EGFP or ECFP gene in the pMD19-T-EGFP/ECFP vector.

Sequences of Homologous Arms:
TET1LA (left homologous arm): (SEQ ID NO: 11)
TET1 RA (right homologous arm): (SEQ ID NO: 12)
TET3 LA (left homologous arm): (SEQ ID NO: 13)
TET3 RA (right homologous arm): (SEQ ID NO: 14)

The 4 plasmids, comprising plasmids carrying Tet1 and Tet3 sgRNA, and Tet1-EGFP and Tet3-ECFP donors were co-transfected into the DKO-AG-haESCs cell line. mCherry positive cells were sorted, and plated in a Petri dish. After 5 days of growth, the clones were picked and passaged for amplification. The established cell line was identified for the Tet1-EGFP and Tet3-ECFP knockins by PCR. The double knock-in cells were designated as Tet1&3-KI-DAH.

Primers for identification by PCR:
Tet1 LA-F:
(SEQ ID NO. 117)
TTTGTGTCTATGAACTACCAGTGAG Tet1 LA-F:
(SEQ ID NO. 118)
CAGGCCCGGGGTTTTCTTC

```
Tet1 RA-F:
                                             (SEQ ID NO. 119)
CAACGAGAAGCGCGATCACA

Tet1 RA-F:
                                             (SEQ ID NO. 120)
TTTTGACTGATCCCAATTTGCCT

Tet3 LA-F:
                                             (SEQ ID NO. 121)
TGTTCACTGGTGAAGGCCAG

Tet3 LA-F:
                                             (SEQ ID NO. 122)
GAACAGCTCCTCGCCCTTG

Tet3 LA-F:
                                             (SEQ ID NO. 123)
TGAGCAAAGACCCCAACGAG

Tet3 RA-R:
                                             (SEQ ID NO. 124)
ATCGACAAACTTTGGGGCGA
```

Construction Procedure of Tet-TKI-DAH:

sgRNA of Tet2 was annealed and ligated to a BbsI digested px330-mCherry plasmid, and a positive plasmid in which sgRNA was ligated was picked up by sequencing.

For the preparation of Tet2-mCherry donor, by using pmCherry-N1 as a template, and P2A-fluorescence F: GCCACGAAGCAAGCAGGAGATGTT-GAAGAAAACCCCGGGCCTGTGAGCAAGGGCG AGGAG (SEQ ID NO. 125) and P2A-fluorescence R: CTTGTACAGCTCGTCCATG (SEQ ID NO. 126) as primers, a sequence encoding mCherry was amplified and then ligated to a pMD19-T carrier. Subsequently, the left and right homologous arms of the gene of interest were respectively inserted into two sides of the mCherry sequence in the pMD19-T-mCherry vector.

TET2 LA (left homologous arm): (SEQ ID NO: 15)

TET2 RA (right homologous arm): (SEQ ID NO: 16)

The 2 plasmids, comprising the plasmid carrying Tet2 sgRNA and the Tet2-mCherry donor were co-transfected into the Tet1&3-KI-DAH cell line. mCherry positive cells were sorted, and plated in a Petri dish. After 5 days of growth, the clones were picked and passaged for amplification. The established cell line was identified for the Tet2-mCherry knock-in by PCR. The positive cell clone was the Tet-TKI-DAH cell line.

Primers for Identification:

```
Primers for identification:
Tet2 LA-F:
                                             (SEQ ID NO. 127)
CACACCCTTCACCAACAGACG Tet2 LA-R:
                                             (SEQ ID NO. 128)
ATCTCGAACTCGTGGCCGTT Tet2 RA-F:
                                             (SEQ ID NO. 129)
AAGACCACCTACAAGGCCAAG Tet2 RA-R:
                                             (SEQ ID NO. 130)
GGTAGGCAAAGTGCTTTTCTAAGAC
```

B. Construction of Semi-Cloned Mice:

Following the method as described in Section 1.9, the cells constructed above were used as a donor for ICAHCI to construct semi-cloned mice.

C. Results

In this example, DKO-AG-haESCs were obtained in which endogenous Tet1, Tet2 and Tet3 were knocked in different fluorescent reporter groups. First, DKO-AG-haESCs were transfected with a plasmid co-expressing Cas9 and Tet1 and Tet3 sgRNAs (FIG. 3A) and a double stranded DNA donor vector having EGFP and ECFP reporter groups fused respectively to the last terminator of Tet1 and Tet3 (FIGS. 3H and 5K). A total of 150 DKO-AG-haESC cell lines were obtained, with 10 Tet1-EGFP knock-in and 7 Tet3-ECFP knock-in cell lines (FIGS. 5L and 5M). One of the cell lines carrying both Tet1-EGFP and 7 Tet3-ECFP knock-ins was designated as Tet1 & 3-KI-DAH-1 (FIGS. 5N and 5O). ICAHCI results showed that DKO-AG-haESCs carrying Tet1-EGFP and Tet3-ECFP knock-ins have similar semi-cloned mice production capability to WT DKO-AG-haESCs (FIGS. 5P and 5Q, Table 1 and Table S3). Next, the plasmid expressing Cas9 and Tet2 sgRNA and the double-stranded DNA donor vector having the mCherry reporter group fused to the last terminator of the Tet2 gene were transfected into the Tet1 & 3-KI-DAH-1 cell line (FIGS. 3A and 3H). Out of the established 130 cell lines, 8 red-KFP knock-in haploid cell lines were identified (designated as Tet-TKI-DAH-1 through Tet-TKI-DAH-8) (FIGS. 3I and 5R). Finally, the developmental potential of the Tet-TKI-DAH cell line was verified by ICAHCI. Consistently, Tet-TKI-DAH was able to efficiently produce viable semi-cloned mice by injection into oocytes (Fig. 5T, Table 1, and Table S3). Taken together, these results indicate that it is a possible route to produce SC mice having corresponding genetic characteristics by ICAHCI after multi-gene genetic manipulation of DKO-AG-haESCs.

Example 10

Large-Scale Production of Heterozygous Mutant SC Mice with DKO-AG-haESCs Carrying sgRNA Library A. Construction of DKO-AG-haESCs Carrying sgRNA Library Initial cells: $IG^{\Delta DMR}$-$H19^{\Delta DMR}$-AGH-1

Following the method as described in Section 1.5, the virus was prepared and DKO-AG-haESCs were infected with a genome-wide lentiviral sgRNA library, and then transfected with a pX330-mCherry plasmid expressing Cas9, to finally construct DKO-AG-haESCs carrying the sgRNA library.

B. Construction of Semi-Cloned Mice:

Following the method as described in Section 1.9, semi-cloned mice were constructed using the previously constructed cells as a donor for ICAHCI.

Detection of sgRNAs carried in semi-cloned mice:

The sgRNAs were detected by PCR amplification using specific primers, and then the PCR product was subjected to agar gel electrophoresis to observe the presence of a strip.

```
Lenti-sg-F:
                                             (SEQ ID NO. 131)
GTTACTCGAGCCAAGGTCGG Lenti-sg-R:
                                             (SEQ ID NO. 132)
GACTCGGTGCCACTTTTTCA
```

Detection of Allelic Mutation:

According to the sgRNA sequencing, the corresponding gene inserted was identified, and then the upstream and downstream primers were designed by the conventional method in the vicinity of the target gene sgRNA, followed by PCR and sequencing.

C. Results

At present, the genome-wide sgRNA library has been successfully established and used in the loss-of-function genetic screening in human and mouse cells (Koike-Yusa, H., Li, Y., Tan, E. P., Velasco-Herrera Mdel, C., and Yusa, K. (2014). Genome-wide recessive genetic screening in mammalian cells with a lentiviral CRISPR-guide RNA library. Nature biotechnology 32, 267-273). This experiment demonstrates that DKO-AG-haESCs are capable of carrying the sgRNA library and that a large number of mutant mouse models can be obtained simply by a one-step method by ICAHCI (FIG. 4A) (this method is known as Lenti-sgRNA+ pX330). In this test, a newly established and more definite mouse lentiviral library was used. This library had 87,897 sgRNAs designed for the genes of 19,150 encoded proteins in mice. $1.0 \times 10^7$ haploid cell line $IG^{A^{DMR}}$-$H19^{A^{DMR}}$-AGH-1 enriched by FACS were infected with the genome-wide lentiviral sgRNA library. After 2 days, these infected cells were treated with puromycin for 7 days, followed by transfection with the pX330-mCherry plasmid expressing Cas9. Haploid cells expressing mCherry indicated the successful transfection and expression of Cas9, which were then used in ICAHCI experiments following FACS enrichment (FIG. 4B). To detect whether the haploid gene is induced to be mutated by CRISPR-Cas9, 7 haploid cell clones were randomly selected. All of the detected cell clones carried one sgRNA, which was also found to be mutated by DNA sequencing, indicating that gene mutations can be successfully induced in haploid cells by CRISPR-Cas9.

114 semi-cloned mice were obtained by three independent ICAHCI experiments (FIG. 4E and Table 2), of which 82 carried one sgRNA (FIG. 4F). Sequencing of the PCR products of sgRNA revealed that 43 SC mice harbored one allelic mutation of the gene of interest, 39 of which carried insertions or knockouts mutation (indel) that result in frameshift, leading to the loss of function of one allele (FIG. 4G). Interestingly, all the mutations were of the same genotype, indicating that gene mutations are realized in haploid cells after the transient expression of Cas9. Although the remaining 39 mice carried one sgRNA, no DNA cleavage was shown at the site needed to be mutated. This rate was consistent with that previously observed in human cells (Zhou, Y, Zhu, S., Cai, C., Yuan, P., Li, C., Huang, Y., and Wei, W. (2014). High-throughput screening of a CRISPR/Cas9 library for functional genomics in human cells. Nature 509, 487-491) or mouse embryos (Wu, Y., Liang, D., Wang, Y., Bai, M., Tang, W., Bao, S., Yan, Z., Li, D., and Li, J. (2013). Correction of a genetic disease in mouse via use of CRISPR-Cas9. Cell Stem Cell 13, 659-662). This data demonstrates that the introduction of genetic mutations into SC mice can be achieved by ICAHCI of DKO-AG-haESCs harboring the sgRNA library that are transiently transfected to express Cas9, to finally obtain a large number of heterozygous mutant mice in one step.

Example 11

Production of Mice Harboring sgRNA-Mediated Biallelic Mutations with DKO-AG-haESCs in One Step A. Construction of sgRNA-Bearing Haploid Cells Initial cells: $IG^{A^{DMR}}$-$H19^{A^{DMR}}$-AGH-1 DKO-AG-haESCs were infected with the lentiviral CRISPR-sgRNA library following the method as described in Section 1.5, to obtain a cell line carrying the lentiviral sgRNA library.

B. Construction of Semi-Cloned Mice:

The nuclei of the haploid cells carrying sgRNA were injected into mature oocytes by ICAHCI, followed by intracytoplasmic injection of Cas9 mRNA into the reconstructed oocyte (where this protocol was known as Lenti-sgRNA+Cas9 injection). Semi-cloned mice were then constructed by embryo transfer.

sgRNA detection in semi-cloned mice: The detection was carried out following the method as described in Example 9.

Detection of allelic mutation: The detection was carried out following the method as described in Example 9. In addition, the PCR product of the target gene was ligated into the pMD19-T vector, and then the clones were picked up and sequenced.

C. Results

In this experiment, haploid cells carrying sgRNA were injected into mature oocytes by ICAHCI and then Cas9 was injected into the reconstructed oocytes (where this protocol was known as Lenti-sgRNA+Cas9 injection). A total of 45 SC mice carrying one sgRNA were born, of which 22 had genetic mutations (Table 2). Sequencing of the PCR product of the gene of interest revealed that 10 mice had only a monoallelic modification, and other 12 mice were biallelic mutant (which is 23.5% of all born SC mice). Sequencing by TA cloning of the 7 biallelic mutant SC mice revealed that approximately 63% of the clones carried the insertion or deletion mutations (Table S4).

Example 12

Production of Mice Harboring sgRNA-Mediated Biallelic Mutations with DKO-AG-haESCs in One Step A. The sgRNA-bearing haploid cells were constructed following the method as described in Example 10A and the pX330-mCherry plasmid was then transiently transfected into the sgRNA-bearing haploid cells.

B. Construction of Semi-Cloned Mice:

The nuclei of the haploid cells obtained in A were injected into oocytes by ICAHCI, followed by intracytoplasmic injection of Cas9 mRNA. Semi-cloned mice were then constructed by embryo transfer.

sgRNA detection in semi-cloned mice: The detection was carried out following the method as described in Example 9.

Detection of allelic mutation: The detection was carried out following the method as described in Example 11.

C. Results

Figure 6G:
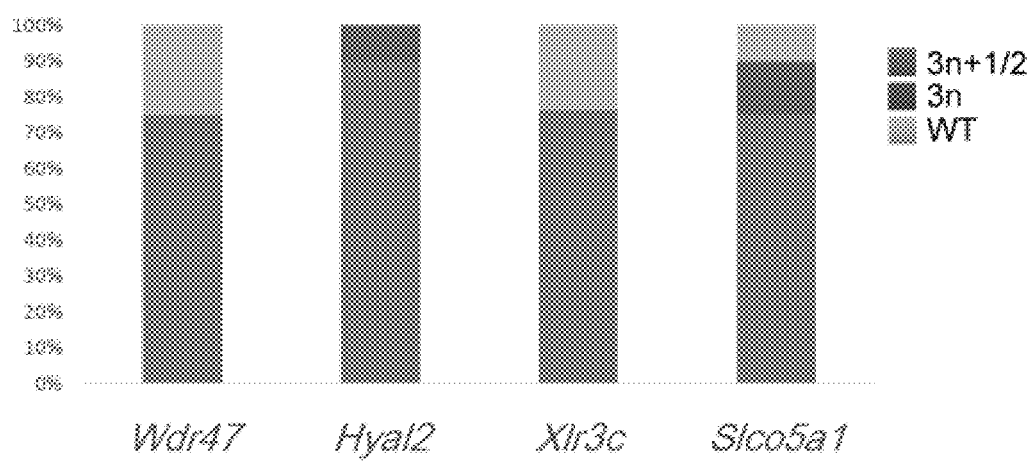
Fig. 6G shows summary of TA cloning and sequencing results of 4 bi-allelic mutant mice.

In this experiment, the pX330-mCheny plasmid was transiently transfected into the sgRNA-bearing haploid cells, and then the cells were injected into oocytes, followed by injection of Cas9 mRNA (FIG. 6A and 6B) (where this protocol was known as Lenti-sgRNA+pX330+Cas9 injection). A total of 27 SC mice carrying one sgRNA were obtained. 22 mice carried genetic mutations (FIGS. 6C and 6D and Table 2), in which 13 of the mutant mice carried biallelic mutations (FIG. 6E) (which was 41.9% of all the SC mice) and the other 9 mice were monoallelic mutant. TA cloning and sequencing results of 5 biallelic mutant mice revealed that about 79% of the clones have insertion or deletion mutations (FIGS. 6F and 6G and Table S4)

Example 13

Production of Mice Harboring sgRNA-Mediated Biallelic Mutations with DKO-AG-haESCs in One Step A. Construction of DKO-AG-haESCs with Constant Expression of Cas9 and sgRNA Library
Initial cells: IG$^{A^{DMR}}$-H19$^{A^{DMR}}$-AGH-1

Specific construction of cell lines by Lenti-Cas9+lenti-sgRNA method: The construction was carried out following the method "co-infection with lentiviral Cas9+lentiviral sgRNA library" as described in Section 1.5.

The cell line integrated with lentiviral Cas9 and lentiviral sgRNA library was further sorted by FACS to enrich the haploid cells for use in subsequent ICAHCI operation.

B. Construction of Semi-Cloned Mice:

Following the method as described in Section 1.9, semi-cloned mice were constructed by ICAHCI using DKO-AG-haESCs with constant expression of Cas9 and sgRNA library as a donor.

Detection of allelic mutation: The detection was carried out following the method as described in Example 11.

Exemplary Primers for Identifying the Mutations in Mice:

```
Polm check-F:
                              (SEQ ID NO. 133)
TCCGATGGGAAGCCAAAAGC Polm check-R:
                              (SEQ ID NO. 134)
CGTACCGCAACCGCGAAGTA Scube1 check-F:
                              (SEQ ID NO. 135)
CCATAATAATCCACTTCCAT Scube1 check-R:
                              (SEQ ID NO. 136)
CCAACCCCTGTCCACTACCT
```

C. Results

In this experiment, DKO-AG-haESCs with constant expression of Cas9 and sgRNA library were obtained by two rounds of screening with drugs. SC mice were then generated by ICAHCI (FIG. 5A-D) (where this protocol was known as Lenti-Cas9+lenti-sgRNA). 272 (18.7%) of the 1,453 embryos reconstructed by ICAHCI were developed fully (FIG. 5E) and the birth rate was basically similar to that obtained with WT DKO-AG-haESCs or DKO-AG-haESCs carrying different gene modifications (Table 2), indicating that after multiple genetic manipulations, the ability of DKO-AG-haESCs to produce SC mice is not affected. A total of 224 SC mice carried one sgRNA and were used for subsequent genotyping (FIG. 5F and Table 2). The results showed that 143 SC mice are genetically mutated, of which 83 are biallelic mutant mice (FIG. 5G). 60 monoallelic mutant SC mice were obtained. Although Cas9 in these mice was supposed to be constantly expressed, silencing of the viral vector led to transcriptional silencing of Cas9 at different development stages of the SC mice. TA cloning and sequencing of 26 biallelic mutant SC mice showed that about 66.3% of the clones have insertion or deletion mutations (FIGS. 5H and I). In order to further determine the mutation efficiency throughout the body of the SC mice, the genetic mutations in different organs (comprising the brain, heart, kidney, liver and lung) of 4 SC mice were analyzed and all of these organs were found to have biallelic mutations. Finally, TA cloning and sequencing of different organs in one SC mouse carrying Scube1 mutation was performed. The results showed that about 80% of the clones have insertion or deletion mutations (FIG. 5J). Interestingly, this SC mouse died within an hour after birth, consistent with previous reports that the Scube1 mutant mouse died shortly after birth (Tu, C. F., Yan, Y. T., Wu, S. Y., Djoko, B., Tsai, M. T., Cheng, C. J., and Yang, R. B. (2008). Domain and functional analysis of a novel platelet-endothelial cell surface protein, SCUBE1. The Journal of biological chemistry 283, 12478-12488). In conclusion, the above experimental results provide sufficient evidence for the possibility of obtaining a large number of mutant mice with DKO-AG-haESCs carrying the sgRNA library, thereby achieving the large-scale gene knockout-based screening at the mouse level, which greatly simplifies the DKO-AG-haESC-mediated gene knockout-based screening.

TABLE 1

Summary of in-vivo development of ICAHCI embryos

| Type of donor cells | Haploid ES cell line | Cell passage number | Number of embryos transferred | Number of growth-arrested mice (% of number of embryos transferred) | Number of normal mice (% of number of embryos transferred) |
|---|---|---|---|---|---|
| Single DMR KO AG-haESCs | H19$^{A^{DMR}}$-AGH Cells | p8-p17 | 1443 | 39 (2.7) | 86 (5.9)$^c$ |
|  | IG$^{A^{DMR}}$-AGU Cells | p8-p23 | 499 | 12 (2.4) | 4 (0.8)$^d$ |
| DKO-AG-haESCs | H19$^{A^{DMR}}$-IG$^{A^{DMR}}$-AGH Cells | p19-p33 | 939 | 4 (0.4) | 210 (22.4) |
|  | IG$^{A^{DMR}}$-H19$^{A^{DMR}}$-AGH Cells | p24-p28 | 544 | 5 (0.9) | 105 (19.3) |
|  | H19$^{A^{DMR}}$-IG$^{A^{DMR}}$-AGH-OG3 Cells | p26-p37 | 510 | 1 (0.2) | 87 (17.1) |
|  | Subtotal | p19-p37 | 1993 | 10 (0.5) | 402 (20.2)$^e$ |
| DKO-AG-ha ESCs carrying Tel 1, 2 and 3 triple mutations | Tet-TKO-DAH Cells | p35-p37 | 407 | 4 (1) | 59 (14.5) |

TABLE 1-continued

Summary of in-vivo development of ICAHCI embryos

| Type of donor cells | Haploid ES cell line | Cell passage number | Number of embryos transferred | Number of growth-arrested mice (% of number of embryos transferred) | Number of normal mice (% of number of embryos transferred) |
|---|---|---|---|---|---|
| DKO-AG-ha ESCs carrying p53, 63 and 73 triple mutations | p53-TKO-DAH Cells | p41-p46 | 660 | 2 (0.3) | 111 (16.7) |
| DKO-AG-ha ESCs carrying Tet1 and 3 knock-ins | Tet1&3-KI-DAH-1 | p40-p47 | 138 | 1 (0.7) | 21 (15.2) |
| DKO-AG-ha ESCs carrying Tet1, 2 and 3 knock-ins | Tet-TKI-DAH-1 | p47-p51 | 874 | 6 (0.7) | 151 (17.3) |
| WT AG-haESCs | AGH Cells[a] | p9-p20 | 294 | 3 (1.0) | 2 (0.7) |
|  | AGH-OG-3 Cells[b] | pl2-p26 | 379 | 6 (1.6) | 7 (1.8) |
|  | Round spermatid |  | 125 | 0 | 28 (22.4) |

[a]AG-haESCs: prepared according to the present invention. See Method 1.3.
[b]AG-haESCs: derived from the prior art, supplied by the author of (Yang, H., Shi, L., Wang, B. A., Liang, D., Zhong, C., Liu, W., Nie, Y., Liu, J., Zhao, J., Gao, X., et al. (2012). Generation of genetically modified mice by oocyte injection of AG-haESCss. Cell 149, 605-617).
[c]For H19$^{\Delta DMR}$-AGR Cells, p < 0.05, compared with WT AG-haESCs
[d]For IG$^{\Delta DMR}$-AGU Cells, p > 0.05, compared with WT AG-haESCs
[e]For DKO-AG-haESCs, p < 0.001, compared with WT AG-haESCs

TABLE SI

Summary of in-vivo development of ICAHCI embryos constructed with different AG-haESCs

| Type of donor cells | Haploid ES cell line | Cell passage number | Number of embryos transferred | Number of growth-arrested mice (% of number of embryos transferred) | Number of normal mice (% of number of embryos transferred) |
|---|---|---|---|---|---|
| H19-DMR KO AG-haESCs | H19$^{\Delta DMR}$-AGH-1 | p8 | 375 | 10 (2.7) | 10 (2.7) |
|  |  | p9 | 180 | 9 (5.0) | 13 (7.2) |
|  | H19$^{\Delta DMR}$-AGH-2 | p8 | 210 | 5 (2.4) | 6 (2.9) |
|  |  | p9 | 116 | 2 (1.7) | 4 (3.4) |
|  |  | p11 | 123 | 3 (2.4) | 3 (2.4) |
|  | H19$^{\Delta DMR}$-AGH-3 | p8 | 271 | 1 (0.4) | 29 (10.7) |
|  |  | p17 | 168 | 9 (5.4) | 21 (12.5) |
| IG-DMR KO AG-haESCs | IG$^{\Delta DMR}$-AGH-1 | p14 | 84 | 0 | 0 |
|  |  | p15 | 100 | 4 (4) | 0 |
|  |  | p17 | 54 | 4 (7.4) | 1 (1.9) |
|  |  | p23 | 81 | 1 (1.2) | 0 |
|  | IG$^{\Delta DMR}$-AGH-2 | p8 | 180 | 3 (1.7) | 3 (1.7) |
| H19$^{\Delta DMR}$-IG$^{\Delta DMR}$-AGH Cells | H19$^{\Delta DMR}$-IG$^{\Delta DMR}$-AGH-1 | pl9 | 175 | 1 (0.6) | 44 (25.1) |
|  | H19$^{\Delta DMR}$-IG$^{\Delta DMR}$-AGH-2 | pl9 | 245 | 2 (0.8) | 56 (22.9) |
|  |  | p29 | 204 | 0 | 46 (22.5) |
|  | H19$^{\Delta DMR}$-IG$^{\Delta DMR}$-AGH-3 | p29 | 165 | 1 (0.6) | 32 (19.4) |
|  | H19$^{\Delta DMR}$-IG$^{\Delta DMR}$-AGH-4 | p33 | 150 | 0 | 32 (21.3) |
| IG$^{\Delta DMR}$-H19$^{\Delta DMR}$-AGH Cells | IG$^{\Delta DMR}$-H19$^{\Delta DMR}$-AGH-1 | p24 | 120 | 1 (0.8) | 26 (21.7) |
|  | IG$^{\Delta DMR}$-H19$^{\Delta DMR}$-AGH-1 | p24 | 180 | 2 (1.1) | 47 (26.1) |
|  | IG$^{\Delta DMR}$-H19$^{\Delta DMR}$-AGH-2 | p28 | 244 | 2 (1.3) | 32 (22.2) |
| IG$^{\Delta DMR}$-H19$^{\Delta DMR}$-AGH-OG3 Cells | IG$^{\Delta DMR}$-H19$^{\Delta DMR}$-AGH-OG3-1 | p26 | 118 | 0 | 17 (14.4) |
|  | IG$^{\Delta DMR}$-H19$^{\Delta DMR}$-AGH-OG3-1 | p30 | 192 | 1 (0.5) | 36 (18.8) |
|  | AGH-OG3-2 | p37 | 200 | 0 | 34 (17) |

TABLE S1-continued

Summary of in-vivo development of ICAHCI embryos constructed with different AG-haESCs

| Type of donor cells | Haploid ES cell line | Cell passage number | Number of embryos transferred | Number of growth-arrested mice (% of number of embryos transferred) | Number of normal mice (% of number of embryos transferred) |
|---|---|---|---|---|---|
| WT AG-haESCs | AGH-OG-3[a] | p12 | 82 | 0 | 1 (1.2) |
| | | p20 | 93 | 4 (4.3) | 0 |
| | | p24 | 140 | 2 (1.4) | 5 (3.6) |
| | | p26 | 64 | 0 | 1 (0.9) |
| | AGH-2[b] | p19 | 114 | 0 | 1 (0.9) |
| | | p20 | 62 | 3 (4.8) | 0 |
| | AGH-3[c] | p9 | 118 | 0 | 1 (1.2) |

[a]AG-haESCs: made according to the prior art.
[b]AG-haESCs: derived from the prior art (Yang, H., Shi, L., Wang, B. A., Liang, D., Zhong, C., Liu, W., Nie, Y., Liu, J., Zhao, J., Gao, X., et al. (2012). Generation of genetically modified mice by oocyte injection of androgenetic haploid embryonic stem cells. Cell 149, 605-617)

TABLE S3

Summary of in-vivo development of ICAHCI embryos constructed with genetically modified DKO-AG-haESCs

| Type of donor cells | Haploid ES cell line | Cell passage number | Number of embryos transferred | Number of growth-arrested mice (% of number of embryos transferred) | Number of normal mice (% of number of embryos transferred) |
|---|---|---|---|---|---|
| DKO-AG-ha ESCs Carrying Tet1, 2 and 3 Mutations | Tet-TKO-DAH-1 | p37 | 131 | 2 (1.5) | 17 (13) |
| | Tet-TKO-DAH-2 | p37 | 54 | 0 | 9 (16.7) |
| | Tet-TKO-DAH-3 | p36 | 174 | 1 (0.6) | 27 (15.5) |
| | Tet-TKO-DAH-4 | p35 | 48 | 1 (2.1) | 6 (12.5) |
| DKO-AG-ha ESCs carrying p53, p63 and p73 mutations | p53-TKO-DAH-1 | p42 | 182 | 1 (0.5) | 34 (18.7) |
| | | p44 | 186 | 0 | 32 (17.2) |
| | p53-TKO-DAH-2 | p41 | 154 | 0 | 23 (14.9) |
| | | p42 | 48 | 1 (2.1) | 8 (16.7) |
| | p53-TKO-DAH-3 | p46 | 90 | 0 | 14 (15.6) |
| DKO-AG-haESCs carrying Tet1 and 3 knock-ins | Tet1&3-KI-DAH-1 | p40 | 58 | 1 (1.7) | 10 (17.2) |
| | | p47 | 80 | 0 | 11 (13.8) |
| DKO-AG-ha ESCs carrying Tet1, 2 and 3 knock-ins | Tet-TKI-D AH-1 | p47 | 48 | 1 (2.1) | 8 (16.7) |
| | | p49 | 174 | 0 | 32 (19) |
| | Tet-TKI-D AH-2 | p47 | 96 | 3 (3) | 10 (10.4) |
| | | p50 | 136 | 1 (0.7) | 22 (16.2) |
| | Tet-TKI-D AH-3 | p49 | 48 | 0 | 8 (16.7) |
| | Tet-TKI-D AH-4 | p50 | 102 | 1 (1.0) | 14 (13.7) |
| | Tet-TKI-D AH-5 | p51 | 174 | 0 | 39 (22.4) |
| | Tet-TKI-D AH-6 | p51 | 96 | 0 | 18 (18.8) |

TABLE 2

Summary of in-vivo development of ICAHCI embryos constructed with DKO-AG-haESCs carrying sgRNA library

| Strategy | Number of embryos transferred | Number of SC mice (% of number of embryos transferred) | Number of SC mice without sgRNA | Number of SC mice with sgRNA (n > 2) | Number of SC mice with one sgRNA | Number of SC mice with biallelic mutation | Number of SC mice with monoallelic mutation |
|---|---|---|---|---|---|---|---|
| Lenti-sgRNA+ pX330 | 580 | 114 (19.7) | 11 | 21 | 82 | 0 | 43 |

TABLE 2-continued

Summary of in-vivo development of ICAHCI embryos constructed with DKO-AG-haESCs carrying sgRNA library

| Strategy | Number of embryos transferred | Number of SC mice (% of number of embryos transferred) | Number of SC mice without sgRNA | Number of SC mice with sgRNA (n > 2) | Number of SC mice with one sgRNA | Number of SC mice with biallelic mutation | Number of SC mice with monoallelic mutation |
|---|---|---|---|---|---|---|---|
| Lenti-sgRNA+Cas9 injection | 306 | 51 (16.7) | 0 | 4 | 47 | 12 | 10 |
| Lenti-sgRNA+pX330+Cas9 injection | 238 | 31 (13.5) | 3 | 1 | 27 | 13 | 9 |
| Lenti-Cas9+lenti-sgRNA | 1453 | 272 (18.7) | 22 | 13 | 237 | 83 | 60 |

The above examples are provided for the purpose of illustrating the embodiments disclosed in the present invention and are not to be construed as limiting the present invention. In addition, various modifications and variations of the methods and compositions made without departing from the scope and spirit of the present invention are apparent to those skilled in the art. While the present invention has been specifically described in connection with various specific preferred embodiments thereof, it is to be understood that the present invention is not limited to these specific embodiments. In fact, various apparent modifications made to the present invention as described above are embraced in the scope of the present.

What is claimed is:

1. A method for constructing a genetically modified semi-cloned mouse, comprising: introducing a mouse androgenetic haploid embryonic stem cell (AG-haESC) into a mouse oocyte to obtain a semi-cloned mouse embryo, wherein the mouse AG-haESC comprises a disruption of H19 DMR and IG-DMR in its genome and the H19 DMR and IG-DMR are knocked out; and gestating the semi-cloned mouse embryo to obtain a semi-cloned mouse.

2. The method for constructing a genetically modified semi-cloned mouse according to claim 1, wherein the semi-cloned mouse embryo is obtained by ICAHCI with the mouse AG-haESC in which H19 DMR and IG-DMR are both knocked out as a donor for ICAHCI.

3. The method for constructing a genetically modified semi-cloned mouse according to claim 1, wherein one or more target genes of interest in the mouse AG-haESC in which H19 DMR and IG-DMR are both knocked out are modified.

4. The method for constructing a genetically modified semi-cloned mouse according to claim 1, wherein the semi-cloned mouse is a sexually reproduced offspring of the semi-cloned mouse constructed according to the method as set forth in claim 1.

5. The method for constructing a genetically modified semi-cloned mouse according to claim 1, wherein the method comprises the steps of:

1) introducing a first sgRNA that specifically targets the H19 DMR, a second sgRNA that specifically targets the IG-DMR, and a CRISPR/Cas9 protein into the mouse AG-haESC, thereby introducing a disruption of the H19 DMR and IG-DMR in a genome of the AG-haESC and obtaining a double knockout mouse AG-haESC in which H19 DMR and IG-DMR are both knocked out;

2) injecting the double knockout mouse AG-haESC into a cytosol of a mouse oocyte to obtain a semi-cloned mouse embryo; and 3) gestating the semi-cloned mouse embryo to obtain a semi-cloned mouse.

6. The method for constructing a genetically modified semi-cloned mouse according to claim 5, further comprising: modifying one or more target genes of interest in the mouse AG-haESC in which H19 DMR and IG-DMR are both knocked out.

* * * * *